United States Patent
Di Francesco et al.

(10) Patent No.: US 8,178,520 B2
(45) Date of Patent: May 15, 2012

(54) MACROCYCLIC COMPOUNDS AS ANTIVIRAL AGENTS

(75) Inventors: Maria Emilia Di Francesco, Pomezia (IT); Emanuela Nizi, Pomezia (IT); Paola Pace, Pomezia (IT); Vincenzo Summa, Pomezia (IT)

(73) Assignee: Istituto di Ricerche di Biologia Molecolare P. Angeletti SpA, Rome (IT)

( * ) Notice: Subject to any disclaimer, the term of this patent is extended or adjusted under 35 U.S.C. 154(b) by 420 days.

(21) Appl. No.: 12/300,887

(22) PCT Filed: May 11, 2007

(86) PCT No.: PCT/EP2007/054594
§ 371 (c)(1),
(2), (4) Date: Nov. 14, 2008

(87) PCT Pub. No.: WO2007/131966
PCT Pub. Date: Nov. 22, 2007

(65) Prior Publication Data
US 2009/0258891 A1 Oct. 15, 2009

(30) Foreign Application Priority Data

May 15, 2006 (GB) .................... 0609492.4

(51) Int. Cl.
*A61K 31/33* (2006.01)
*A61K 31/44* (2006.01)
*A61K 31/519* (2006.01)
*A61K 38/06* (2006.01)
*C07K 5/00* (2006.01)
*C07D 295/00* (2006.01)
*C07D 267/22* (2006.01)
*C07D 245/00* (2006.01)

(52) U.S. Cl. ............ 514/183; 514/306; 514/258.1; 514/21.9; 530/317; 540/450; 540/451; 540/454; 540/460

(58) Field of Classification Search .......... 514/306, 514/258.1, 183, 9; 530/317; 540/450, 451, 540/454, 455, 460
See application file for complete search history.

(56) References Cited

U.S. PATENT DOCUMENTS

| | | | |
|---|---|---|---|
| 3,480,613 A | 11/1969 | Walton | |
| 6,323,180 B1 | 11/2001 | Llinas-Brunet et al. | |
| 6,329,417 B1 * | 12/2001 | Llinas-Brunet et al. | 514/422 |
| 6,608,027 B1 | 8/2003 | Tsantrizos et al. | |
| 6,777,395 B2 | 8/2004 | Bhat et al. | |
| 6,955,174 B2 | 10/2005 | Friedrichs et al. | |
| 7,470,664 B2 | 12/2008 | Holloway et al. | |
| 2002/0019363 A1 | 2/2002 | Ismaili et al. | |
| 2002/0107138 A1 | 8/2002 | Hoveyda et al. | |
| 2002/0107181 A1 * | 8/2002 | Chen et al. | 514/9 |
| 2003/0181363 A1 * | 9/2003 | Llinas-Brunet et al. | 514/9 |
| 2003/0236216 A1 | 12/2003 | Devos et al. | |
| 2004/0006007 A1 | 1/2004 | Gosselin et al. | |
| 2004/0063658 A1 | 4/2004 | Roberts et al. | |
| 2004/0067901 A1 | 4/2004 | Bhat et al. | |
| 2004/0106559 A1 * | 6/2004 | Wang et al. | 514/18 |
| 2004/0229776 A1 | 11/2004 | Chen et al. | |
| 2004/0229818 A1 | 11/2004 | Llinas-Brunet et al. | |
| 2004/0254159 A1 | 12/2004 | Hasvold et al. | |
| 2004/0266668 A1 | 12/2004 | Nakajima et al. | |
| 2005/0020503 A1 | 1/2005 | Llinas-Brunet et al. | |
| 2005/0038240 A1 | 2/2005 | Connolly et al. | |
| 2006/0257980 A1 | 11/2006 | Li | |
| 2007/0027071 A1 | 2/2007 | Holloway et al. | |

FOREIGN PATENT DOCUMENTS

| | | |
|---|---|---|
| EP | 1719773 A1 | 11/2006 |
| GB | 2337262 A | 11/1999 |
| GB | 2430621 A | 4/2007 |
| WO | 97/41211 A1 | 11/1997 |
| WO | 98/22496 A2 | 5/1998 |
| WO | 98/46630 A1 | 10/1998 |
| WO | 99/07733 A2 | 2/1999 |

(Continued)

OTHER PUBLICATIONS

Brian W. Dymock et al., "Novel Approaches to the Treatment of Hepatitis C Virus Infection," 11 Antiviral Chemistry & Chemotherapy 79-96 (2000).

Hugo R. Rosen & David R. Gretch, "Hepatitis C virus: current understanding and prospects for future therapies," 5 Molec. Med. Today 393-99 (1999).

Darius Moradpour & Hubert E Blum, "Current and evolving therapies for hepatitis C," 11 Euro. J. Gastroenterol. Hepatol. 1189-1202 (1999).

(Continued)

*Primary Examiner* — Shengjun Wang
(74) *Attorney, Agent, or Firm* — Sheldon O. Heber; Julie M. Lake

(57) ABSTRACT

The present invention relates to macrocyclic compounds of formula (I): wherein W, n, $R^1$, $R^a$, $R^b$, $R^3$, $R^4$, M, Z, ring A and ring B are defined herein, and pharmaceutically acceptable salts thereof, pharmaceutical compositions comprising them, and their use for the treatment or prevention of infection by hepatitis C virus.

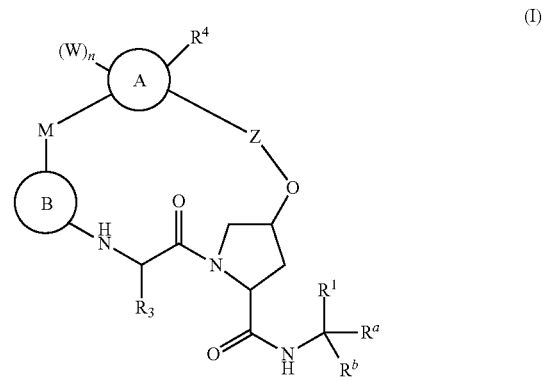

20 Claims, 1 Drawing Sheet

FOREIGN PATENT DOCUMENTS

| | | |
|---|---|---|
| WO | 99/07734 A2 | 2/1999 |
| WO | 99/38888 A1 | 8/1999 |
| WO | 99/43691 A1 | 9/1999 |
| WO | 99/50230 A1 | 10/1999 |
| WO | 99/64442 A1 | 12/1999 |
| WO | 00/09543 A2 | 2/2000 |
| WO | 00/09546 A2 | 2/2000 |
| WO | 00/25780 A1 | 5/2000 |
| WO | 00/59929 A1 | 10/2000 |
| WO | 01/00622 A1 | 1/2001 |
| WO | 01/47883 A1 | 7/2001 |
| WO | 01/60379 A1 | 8/2001 |
| WO | 01/68663 A1 | 9/2001 |
| WO | 01/77091 A2 | 10/2001 |
| WO | 01/77113 A2 | 10/2001 |
| WO | 01/79246 A2 | 10/2001 |
| WO | 01/90121 A2 | 11/2001 |
| WO | 01/92282 A2 | 12/2001 |
| WO | 02/04425 A1 | 1/2002 |
| WO | 02/06246 A1 | 1/2002 |
| WO | 02/18404 A2 | 3/2002 |
| WO | 02/20497 A1 | 3/2002 |
| WO | 02/32920 A2 | 4/2002 |
| WO | 02/48116 A2 | 6/2002 |
| WO | 02/48165 A2 | 6/2002 |
| WO | 02/48172 A2 | 6/2002 |
| WO | 02/051425 A1 | 7/2002 |
| WO | 02/057287 A2 | 7/2002 |
| WO | 02/057425 A2 | 7/2002 |
| WO | 02/100415 A2 | 12/2002 |
| WO | 03/015755 A1 | 2/2003 |
| WO | 03/026589 A2 | 4/2003 |
| WO | 03/026675 A1 | 4/2003 |
| WO | 03/062192 A1 | 7/2003 |
| WO | 03/062211 A1 | 7/2003 |
| WO | 03/064455 A2 | 8/2003 |
| WO | 03/068244 A1 | 8/2003 |
| WO | 03/093290 A2 | 11/2003 |
| WO | 03/099274 A1 | 12/2003 |
| WO | 2004/000858 A2 | 12/2003 |
| WO | 2004/002422 A2 | 1/2004 |
| WO | 2004/002999 A2 | 1/2004 |
| WO | 2004/003000 A2 | 1/2004 |
| WO | 2004/003138 A2 | 1/2004 |
| WO | 2004/007512 A2 | 1/2004 |
| WO | 2004/011478 A2 | 2/2004 |
| WO | 2004/013300 A2 | 2/2004 |
| WO | 2004/028481 A2 | 4/2004 |
| WO | 2004/041201 A2 | 5/2004 |
| WO | 2004/087714 A1 | 10/2004 |
| WO | 2004/093915 A1 | 11/2004 |
| WO | 2004/103996 A1 | 12/2004 |
| WO | 2004/110442 A1 | 12/2004 |
| WO | 2005/003147 A1 | 1/2005 |
| WO | 2005/016927 A1 | 2/2005 |
| WO | 2005/023819 A1 | 3/2005 |
| WO | 2005/034941 A1 | 4/2005 |
| WO | 2005/046712 A1 | 5/2005 |
| WO | 2005/070955 A1 | 8/2005 |
| WO | 2005/080399 A1 | 9/2005 |
| WO | 2006/008556 A1 | 1/2006 |
| WO | 2006/020082 A1 | 2/2006 |
| WO | 2006/021341 A1 | 3/2006 |
| WO | 2006/027628 A2 | 3/2006 |
| WO | 2006/029912 A1 | 3/2006 |
| WO | 2006/046030 A1 | 5/2006 |
| WO | 2006/046039 A2 | 5/2006 |
| WO | 2006/119061 A1 | 11/2006 |
| WO | 2006/119975 A1 | 11/2006 |
| WO | 2007/015787 A1 | 2/2007 |
| WO | 2007/015855 A1 | 2/2007 |
| WO | 2007/016441 A1 | 2/2007 |
| WO | 2007/028789 A1 | 3/2007 |
| WO | 2007/029029 A2 | 3/2007 |
| WO | 2007/131966 A1 | 11/2007 |
| WO | 2007/145894 A2 | 12/2007 |
| WO | 2007/148135 A1 | 12/2007 |
| WO | 2008/051475 A2 | 5/2008 |
| WO | 2008/051477 A2 | 5/2008 |
| WO | 2008/051514 A2 | 5/2008 |
| WO | 2008/057028 A1 | 5/2008 |
| WO | 2008/057208 A2 | 5/2008 |
| WO | 2008/057209 A1 | 5/2008 |
| WO | 2008/112108 A1 | 9/2008 |
| WO | 2009/005687 A1 | 1/2009 |
| WO | 2009/010804 A1 | 1/2009 |
| WO | 2009/064955 A1 | 5/2009 |
| WO | 2009/064975 A1 | 5/2009 |

OTHER PUBLICATIONS

Ralf Bartenschlager, "Candidate Targets for Hepatitis C Virus-Specific Antiviral Therapy," 40(5-6) Intervirology 378-93 (1997).

Georg M. Lauer & Bruce D. Walker, "Hepatitis C Virus Infection," 345(1) N. Engl. J. Med. 41-52 (2001); correction: 345 (19) N. Engl. J. Med. 1425-26 (2001).

Brain W. Dymock, "Emerging therapies for hepatitis C virus infection," 6 Emerging Drugs 13-42 (2001).

Charlene Crabb, Infectious Diseases. "Hard-Won Advances Spark Excitement about Hepatitis C," Science 506-507 (2001).

Rogers E. Harry-O'Kuru et al., "A Short, Flexible Route toward 2'-C-Branched Ribonucleosides," 62 J. Org. Chem. 1754-59 (1997).

Michael S. Wolfe & Rogers E. Harry-O'Kuru, "A Concise Synthesis of 2'-C-Methylribonucleosides," 36(42) Tetrahedron Letters 7611-14 (1995).

Scott J. Miller et al., "Application of Ring-Closing Metathesis to the Synthesis of Rigidified Amino Acids and Peptides," 118 J. Am. Chem. Soc. 9606-14 (1996).

Jason S. Kingsbury et al., "A Recyclable Ru-Based Metathesis Catalyst," 121 J. Am. Chem. Soc. 791-99 (1999).

Matthias Scholl et al., "Synthesis and Activity of a New Generation of Ruthenium-Based Olefin Metathesis Catalysts Coordinated with 1,3-Dimesityl-4,5-dihydroimidazol-2-ylidene Ligands," 1(6) Organic Letters 953-56 (1999).

Alois Furstner et al., "Total Synthesis and Structural Refinement of the Cyclic Tripyrrole Pigment Nonylprodigiosin," 64 J. Org. Chem. 8275-80 (1999).

Tina M. Trnka & Robert H. Grubbs, "The Development of L2X2R-CHR Olefin Metathesis Catalysts: An Organometallic Success Story," 34 Acc. Chem. Res. 18-29 (2001).

A. Srikrishna et al., "Enantiospecific Construction of the BC-ring System of Taxanes," 45 Tetrahedron Letters 2939-42 (2004).

Yung-Son Hon et al., "Dibromomethane as one-carbon source in organic synthesis: a versatile methodology to prepare the cyclic and acyclic alpha-methylene or alpha-keto acid derivatives from the corresponding terminal alkenes," 60 Tetrahedron 4837-60 (2004).

Eusebio Juaristi & Hugo A. Jimenez-Vazquez, "Single Electron Transfer Mechanism in the Reaction of 1,3-Dithianyllithium and Alkyl Iodides," 56 J. Org. Chem. 1623-30 (1991).

Paola Conti et al., "Chemoenzymatic Synthesis of the Enantiomers of Desoxymuscarine," 9 Tetrahedron: Asymmetry 657-65 (1998).

Robert M. Coates & Mark W. Johnson, "Stereoselective Synthesis of Moenocinol and Assignment of Its Carbon-13 Nuclear Magnetic Resonance Spectrum," 45 J. Org. Chem. 2685-97 (1980).

D. Becker & N. Haddad, "Steric Effects in Intramolecular [2+2] Photocycloaddition of C=C Double Bonds to Cyclohexenones," 49(4) Tetrahedron 947-64 (1993).

Richard A. Bunce et al., "Tandem SN2-Michael Reactions for the Preparation of Simple Five- and Six-Membered-Ring Nitrogen and Sulfur Heterocycles," 57 J. Org. Chem. 1727-33 (1992).

Masao Tokuda et al., "Aminyl Radical Cyclization by Means of Anodic Oxidation. Stereoselective Synthesis of cis-1-Methyl-2,5-Disubstituted Pyrrolidines," 26(49) Tetrahedron Letters 6085-88 (1985).

Robert Haner et al., "174. Generation and Reactions of Lithiated tert-Butyl and 2,6-Di(tert-butyl)-4-methylphenyl Cyclopropanecarboxylates," 69 Helvetica Chimica Acta 1655-65 (1986).

Herbert O. House et al., "Cyclization of Unsaturated Hydroxylamine Derivatives," 41(5) J. Org. Chem. 855-63 (1976).

Theophil Eicher et al., "Bryophyte Constituents; 7: New Synthesis of (+)-Rosmarinic Acid and Related Compounds," Synthesis 755-62 (Jun. 1996).

Michael C. Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," 31 J. Med. Chem. 2136-45 (1988).

Marc-Andre Poupart et al., "Solid-Phase Synthesis of Peptidomimetic Inhibitors for the Hepatitis C Virus NS3 Protease," 66(14) J. Org. Chem. 4743-51 (2001).

Nigel J. Liverton et al., Molecular Modeling Based Approach to Potent P2-P4 Macrocyclic Inhibitors of Hepatitis C NS3/NS4A Protease, 130 J. Am. Chem. Soc. 4607-09 (2008).

Anthony C. Allison & Elsie M. Eugui, "Immunosuppressive and other anti-rheumatic activities of mycophenolate mofetil," 44 Agents and Actions Supplements 165-88 (1993).

Joel Kirschbaum, "Amantadine," 12 Profiles of Drug Substances, Excipients and Related Methodology 1-36 (1983).

T. K. Chakaborty et al., "Alpha-Phenylglycinol as chiral auxilliary in diastereoselective Strecker synthesis of alpha-amino acids," 51(33) Tetrahedron 9179-90 (1995).

W. Clark Still et al., "Rapid Chromatographic Technique for Preparative Separations with Moderate Resolution," 43(14) J. Org. Chem. 2923-25 (1978).

Michael D. Cooke et al., :The occurrence of a hydride shift in the aromatization of 1,4-epoxy-1,2-dihydronaphthalenes, 11 J. Chem. Soc. Perkin Trans. I: Phys. Org. Chem. 1377 (1984).

Paul Aeberli et al., "Neuropharmacological investigation of N-benzylsulfamides," 10(4) J. Med. Chem. 636-42 (1967).

Nathalie Goudreau & Montse Llinas-Brunet, "The Therapeutic Potential of NS3 Protease Inhibitors in HCV Infection," 14(9) Expert Opinion 1129-44 (2005).

Volker Lohmann et al., "Selective Stimulation of Hepatitis C Virus and Pestivirus NS5B RNA Polymerase Activity by GTP," 274(16) J. Bio. Chem. 10807-15 (1999).

V. Lohmann et al., "Replication of Subgenomic Hepatitis C Virus RNAs in a Hepatoma Cell Line," 285 Science 110-13 (1999).

Kevin X. Chen et al. "Novel Potent Hepatitis C Virus NS3 Serine Protease Inhibitors Derived from Proline-Based Macrocycles," 49 J. Med. Chem. 995-1005 (2006).

Yuri Goldberg et al., "Highly regioselective bromination of 2,3-dimethylanisole with N-bromosuccinimide," 57 J. Org. Chem. 6374-76 (1992).

Manfred Schlosser et al., "8-Methoxyisoquinoline derivatives through ortho-selective metallation of 2-(3-methoxyphenyl)ethylamines," 32(17) Tetrahedron Letters 1965-66 (1991).

Angela Casini et al., "Carbonic Anhydrase inhibitors inhibition of cytosolic isozymes I and II with sulfamide derivatives," 13(5) Bioorg. Med. Chem. Lett. 837-40 (2003).

Kiyotaka Onisuka et al., "A novel route to 2,3-disubstituted indoles via palladium-catalyzed three-component coupling of aryl iodide, o-alkenylphenyl isocyanide and amine," 43 Tetrahedron Letters 6197-99 (2002).

Duane E. Rudisill & J. K. Stille, "Palladium-catalyzed synthesis of 2-substituted indoles," 54(25) J. Org. Chem. 5856-66 (2002).

Makoto Satoh et al., "Palladium-Catalyzed Cross-Coupling Reaction of (1-Ethoxy-1-alken-2-yl)boranes With ortho-Functionalized Iodoarenes. A Novel and Convenient Synthesis of Benzo-Fused Heteroaromatic Compounds," Synthesis Communications 373-377 (Apr. 1987).

Yuusaku Yokoyama et al., "Palladium-Catalyzed Reaction of 3-Bromoindole Derivative with Allyl Esters in the Presence of Hexa-n-butyldistannane," 31(8) Heterocycles 1505-11 (1990).

Steven W. Ludmerer et al., "A transient cell-based phenotype assay for hepatitis C NS3/4A protease: Application to potency determinations of a novel macrocyclic inhibitor against diverse protease sequences isolated from plasma infected with HCV," 151 Journal of Virological Methods 301-07 (2008).

John A. McCauley et al., "Bismacrocyclic Inhibitors of Hepatitis C NS3/4a Protease," 47 Angew. Chem. Int. Ed. 9104-07 (2008).

Ashok Arasappan et al., "P2-P4 Macrocyclic inhibitors of hepatitis C virus NS3-4A serine protease," 16 Bioorganic & Medicinal Chemistry Letters 3960-65 (2006).

Youwei Yan et al., Complex of NS3 protease and NS4A peptide of BK strain hepatitis C virus: A 2.2 Angstrom resolution structure in a hexagonal crystal form, 7 Protein Science 837 (1998).

Youla S. Tsantrizos, The Design of a Potent Inhibitor of the Hepatitis C Virus NS3 Protease: BILN 2061—From the NMR Tube to the Clinic, 76 Biopolymers (Peptide Science) 309-323 (2004).

* cited by examiner

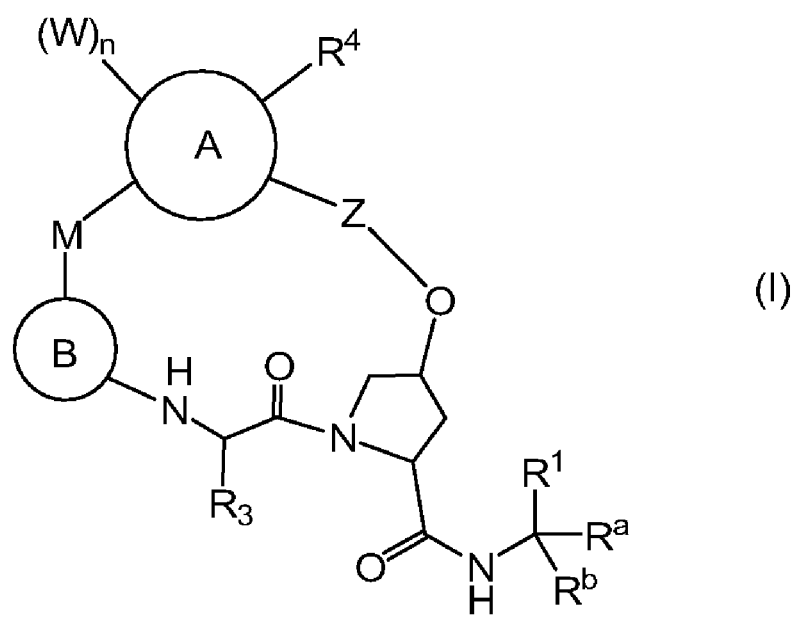
(I)

MACROCYCLIC COMPOUNDS AS ANTIVIRAL AGENTS

CROSS-REFERENCE TO RELATED APPLICATIONS

This application is a National Stage application of International application PCT/EP2007/054594, filed May 11, 2007. This application also claims priority to British Provisional application GB 0609492.4, filed May 15, 2006.

FIELD OF THE INVENTION

The present invention relates to macrocyclic compounds that are useful as inhibitors of the hepatitis C virus (HCV) NS3 protease, their synthesis, and their use for treating or preventing HCV infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. According to the World Health Organization, there are more than 170 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their offspring.

Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection.

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein, and is considered a prime drug target since it is responsible for an intramolecular cleavage at the NS3/4A site and for downstream intermolecular processing at the NS4A/4B, NS4B/5A and NS5A/5B junctions. Previous research has identified classes of peptides, such as hexapeptides as well as tripeptides discussed in U.S. patent applications US2005/0020503, US2004/0229818, and US2004/00229776, showing degrees of activity in inhibiting the NS3 protease. The aim of the present invention is to provide further compounds which exhibit activity against the HCV NS3 protease.

BRIEF DESCRIPTION OF THE DRAWINGS

The subject matter described herein may be understood with reference to the FIGURE.

SUMMARY OF THE INVENTION

Thus, in one aspect, there is provided the compound of formula (I):

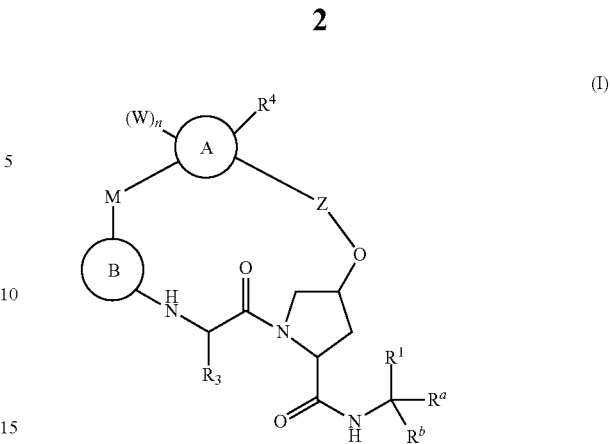

or a pharmaceutically acceptable salt thereof,
wherein:
n is 0, 1 or 2;
$R^1$ is $CO_2R^5$, $CONR^5SO_2R^5$, $CONR^5SO_2N(R^5)_2$ or tetrazolyl;
$R^a$ is $C_{2-6}$alkylene-$R^2$;
$R^b$ is hydrogen;
or $R^a$ and $R^b$, together with the carbon atom to which they are attached, form a $C_{3-6}$cycloalkyl group, optionally substituted by $R^2$;
$R^2$ is $C_{1-6}$alkyl, $C_{2-6}$alkenyl or $C_{3-8}$cycloalkyl, wherein said alkyl, alkenyl or cycloalkyl is optionally substituted with 1 to 3 halo;
$R^3$ is $C_{1-6}$alkyl, $(CH_2)_{0-3}C_{3-8}$cycloalkyl, $(CH_2)_{0-3}$aryl or $(CH_2)_{0-3}$Het, optionally substituted by halo, $OR^5$, $SR^5$, $N(R^5)_2$, $C_{1-6}$alkyl, $NO_2$, $CN$, $CF_3$, $NR^5SO_2R^5$, $SO_2N(R^5)_2$, $NHCO_2R^5$, $NHCOR^5$, $NHCONHR^5$, $CO_2R^5$, $C(O)R^5$ or $CON(R^5)_2$;
$R^4$ is hydrogen, halo, hydroxy, $C_{1-6}$alkyl, $C_{1-6}$alkoxy, CN, $NO_2$, $C_{3-8}$cycloalkyl, $N(R^5)_2$, aryl or heteroaryl, optionally substituted by 1 to 8 halo or $C_{1-4}$alkyl;
each $R^5$ is independently hydrogen, $C_{1-6}$alkyl or $C_{3-8}$cycloalkyl;
each W is independently halo, $OR^5$, $C_{1-6}$alkyl, CN, $NO_2$, $CF_3$, $CO_2R^5$, $CON(R^5)_2$, $COR^5$, $NR^5C(O)R^5$, aryl or heteroaryl;
Z is a bond or C=O;
M is $C_{2-12}$alkylene or $C_{2-12}$alkenylene, optionally substituted by $C_{1-6}$alkyl, $(CH_2)_{0-3}C_{3-8}$cycloalkyl or $(CH_2)_{0-3}$aryl, and optionally containing one O or S atom;
ring A is a 8- to 10-membered fused heterobicyclic ring system containing 1 to 4 heteroatoms selected from N, O and S; and
ring B is a C-linked 5- or 6-membered heteroaromatic ring containing 1 to 4 heteroatoms selected from N, O and S.

In one embodiment of the present invention, n is 0 or 1. Preferably, n is 0.

In another embodiment, $R^1$ is $CONR^5SO_2R^5$ or $CONR^5SO_2N(R^5)_2$ where $R^5$ is as hereinbefore defined. Preferably, $R^1$ is $CONR^5SO_2R^5$ where $R^5$ is as hereinbefore defined. More preferably, $R^1$ is $CONHSO_2R^5$ where $R^5$ is as hereinbefore defined. Especially, $R^1$ is $CONHSO_2$—$C_{3-8}$cycloalkyl. More especially, $R^1$ is $CONHSO_2$—$C_{3-6}$cycloalkyl. Most especially, $R^1$ is $CONHSO_2$-cyclopropyl.

In another embodiment, $R^a$ is $C_{2-5}$alkylene-$R^2$ where $R^2$ is as hereinbefore defined. Preferably, $R^a$ is $C_{2-4}$alkylene-$R^2$ where $R^2$ is $C_{1-6}$alkyl, optionally substituted with 1 to 3 halo. More preferably, $R^a$ is $C_{2-3}$alkylene-$R^2$ where $R^2$ is $C_{1-4}$alkyl, optionally substituted with 1 to 3 fluoro or chloro. Most preferably, $R^a$ is ethylene-$R^2$ where $R^2$ is $C_{1-2}$alkyl, optionally substituted by 1 to 3 fluoro. Especially, $R^a$ is ethylene-$R^2$ where $R^2$ is difluoromethyl or trifluoromethyl.

In another embodiment, $R^a$ and $R^b$, together with the carbon atom to which they are attached, form a $C_{3-5}$cycloalkyl group, optionally substituted by $R^2$, where $R^2$ is $C_{1-6}$alkyl or $C_{2-6}$alkenyl. Preferably, $R^a$ and $R^b$, together with the carbon atom to which they are attached form a $C_{3-4}$cycloalkyl group, substituted by $C_{1-4}$alkyl or $C_{2-4}$alkenyl. More preferably, $R^a$ and $R^b$, together with the carbon atom to which they are attached, form a cyclopropyl group, substituted by —CH=CH$_2$.

In another embodiment, $R^3$ is $C_{1-6}$alkyl, or $(CH_2)_{0-3}C_{3-8}$cycloalkyl, optionally substituted by halo, $OR^5$ or $C_{1-6}$alkyl, where $R^5$ is as hereinbefore defined. Preferably, $R^3$ is $C_{1-6}$alkyl or $(CH_2)_{0-3}C_{3-8}$cycloalkyl. More preferably, $R^3$ is $C_{1-4}$alkyl or $C_{3-6}$cycloalkyl. Most preferably, $R^3$ is $C_{3-4}$alkyl or $C_{5-6}$cycloalkyl. Especially, $R^3$ is $^i$propyl, $^s$butyl, $^t$butyl, cyclopentyl or cyclohexyl.

In another embodiment, $R^4$ is hydrogen, halo, hydroxy, $C_{1-6}$alkyl, $C_{1-6}$alkoxy, $C_{3-8}$cycloalkyl or aryl. Preferably, $R^4$ is hydrogen, iodo, $C_{1-4}$alkyl, $C_{1-4}$alkoxy or phenyl. Most preferably, $R^4$ is hydrogen, iodo, ethyl, methoxy or phenyl.

In another embodiment, each W is independently halo, $OR^5$, $C_{1-6}$alkyl, CN, $NO_2$, $CF_3$, $CO_2R^5$ or $CON(R^5)_2$, where $R^5$ is as hereinbefore defined. Preferably, each W is independently halo, $OC_{1-6}$alkyl, CN, $NO_2$ or $CF_3$. More preferably, each W is independently $OC_{1-4}$alkyl. Most preferably, W is methoxy.

DETAILED DESCRIPTION OF THE INVENTION

In another embodiment, Z is a bond when A is pyridinyl.

In another embodiment, Z is C=O when A is pyrrolidinyl. Preferably, Z is attached to the nitrogen atom of the pyrrolidinyl moiety.

In another embodiment, M is $C_{2-8}$alkylene or $C_{2-8}$alkenylene, optionally substituted by $C_{1-4}$alkyl or $C_{3-6}$cycloalkyl, and optionally containing one O atom. Preferably, M is $C_{3-6}$alkylene or $C_{3-6}$alkenylene, optionally substituted by $C_{1-4}$alkyl, and optionally containing one O atom. More preferably, M is $C_{4-5}$alkylene or $C_{4-5}$alkenylene, optionally substituted by $C_{1-2}$alkyl, and optionally containing one O atom. Examples of suitable M groups include butylene, pentylene,

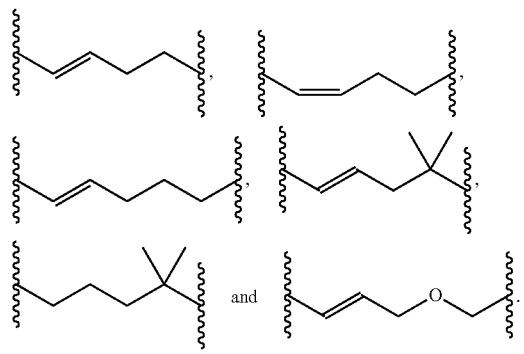

In another embodiment, A is a 9- or 10-membered fused heterobicyclic ring system containing 1 to 3 heteroatoms selected from N and O. Preferably, A is a 9- or 10-membered fused heterobicyclic ring system containing 1 or 2 N atoms. More preferably, A is quinolinyl, isoquinolinyl, isoindolyl or imidazo[1,2-a]-pyridinyl.

In another embodiment, B is a C-linked 5-membered heteroaromatic ring containing 2 or 3 heteroatoms selected from N, O and S. Preferably, B is oxazolyl, isoxazolyl, thiazolyl, isothiazolyl, furazyl or oxadiazolyl. More preferably, B is thiazolyl or 1,3,4-oxadiazolyl.

In another embodiment of the present invention, there is provided the compound of formula (Ia):

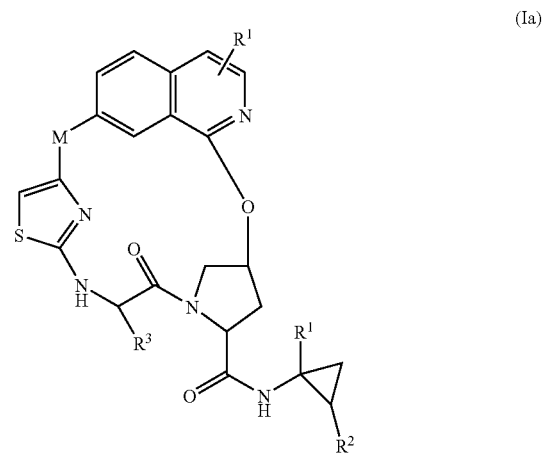

(Ia)

or a pharmaceutically acceptable salt thereof, wherein $R^1$, $R^2$, $R^3$, $R^4$ and M are as defined in relation to formula (I).

Preferably, $R^1$ is $C(O)NR^5SO_2R^5$ where $R^5$ is as defined in relation to formula (I). More preferably, $R^1$ is $C(O)NHSO_2R^5$ where $R^5$ is as defined in relation to formula (I). Most preferably, $R^1$ is $C(O)NHSO_2$—$C_{3-6}$cycloalkyl. Especially, $R^1$ is $C(O)NHSO_2$-cyclopropyl.

Preferably, $R^2$ is $C_{2-6}$alkenyl. More preferably, $R^2$ is —CH=CH$_2$.

Preferably, $R^3$ is $C_{1-6}$alkyl or $(CH_2)_{0-3}C_{3-8}$cycloalkyl. More preferably, $R^3$ is $C_{1-4}$alkyl or $C_{3-6}$cycloalkyl. Most preferably, $R^3$ is $C_{2-4}$alkyl or $C_{5-6}$cycloalkyl. Especially, $R^3$ is $^i$propyl, $^s$butyl, $^t$butyl, cyclopentyl or cyclohexyl.

Preferably, $R^4$ is hydrogen, halo, hydroxy, $C_{1-6}$alkyl, $C_{1-6}$alkoxy, $C_{3-8}$cycloalkyl or aryl. More preferably, $R^4$ is hydrogen, $C_{1-6}$alkyl or $C_{3-8}$cycloalkyl. Most preferably, $R^4$ is hydrogen.

Preferably, M is $C_{2-8}$alkylene or $C_{2-8}$alkenylene, optionally substituted by $C_{1-6}$alkyl. More preferably, M is $C_{3-6}$alkylene or $C_{3-6}$alkenylene, optionally substituted by $C_{1-4}$alkyl. Most preferably, M is $C_{4-5}$alkylene or $C_{4-5}$alkenylene, optionally substituted by $C_{1-2}$alkyl. Especially, M is butylene, pentylene,

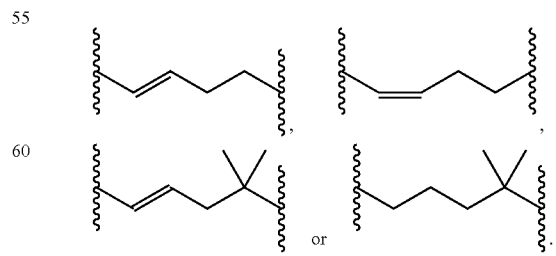

In another embodiment of the present invention, there is provided the compound of formula (Ib):

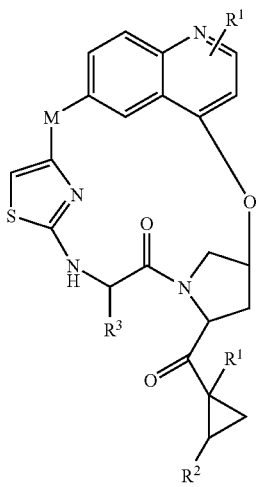

(Ib)

or a pharmaceutically acceptable salt thereof,
wherein $R^1$, $R^2$, $R^3$, $R^4$ and M are as defined in relation to formula (I).

Preferably, $R^1$ is $C(O)NR^5SO_2R^5$ where $R^5$ is as defined in relation to formula (I). More preferably, $R^1$ is $C(O)NHSO_2R^5$ where $R^5$ is as defined in relation to formula (I). Most preferably, $R^1$ is $C(O)NHSO_2$—$C_{3-6}$cycloalkyl. Especially, $R^1$ is $C(O)NHSO_2$-cyclopropyl.

Preferably, $R^2$ is $C_{2-6}$alkenyl. More preferably, $R^2$ is —CH=CH$_2$.

Preferably, $R^3$ is $C_{1-6}$alkyl. More preferably, $R^3$ is $C_{3-4}$alkyl. Most preferably, $R^3$ is $^i$propyl.

Preferably, $R^4$ is hydrogen, halo, hydroxy, $C_{1-6}$alkyl, $C_{1-6}$alkoxy, $C_{3-8}$cycloalkyl or aryl. More preferably, $R^4$ is hydrogen, $C_{1-6}$alkyl or aryl. Most preferably, $R^4$ is hydrogen or phenyl. Especially, $R^4$ is phenyl.

When $R^4$ is other than hydrogen, preferably it is attached to the 2-position of the pyridyl moiety.

Preferably, M is $C_{2-12}$alkylene or $C_{2-12}$alkenylene. More preferably, M is $C_{2-8}$alkylene or $C_{2-8}$alkenylene. Most preferably, M is $C_{2-8}$alkylene. Especially, M is $C_{3-6}$alkylene. More especially, M is butylene.

In another embodiment of the present invention, there is provided the compound of formula (Ic):

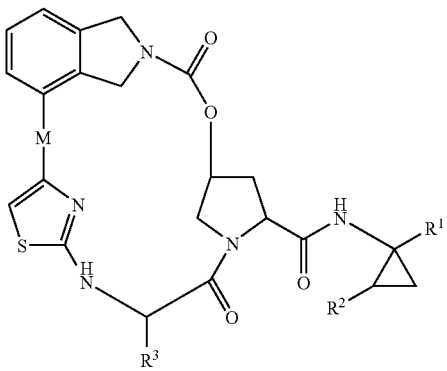

(Ic)

or a pharmaceutically acceptable salt thereof,
wherein $R^1$, $R^2$, $R^3$ and M are as defined in relation to formula (I).

Preferably, $R^1$ is $C(O)NR^5SO_2R^5$ where $R^5$ is as defined in relation to formula (I). More preferably, $R^1$ is $C(O)NHSO_2R^5$ where $R^5$ is as defined in relation to formula (I). Most preferably, $R^1$ is $C(O)NHSO_2$—$C_{3-6}$cycloalkyl. Especially, $R^1$ is $C(O)NHSO_2$-cyclopropyl.

Preferably, $R^2$ is $C_{1-4}$alkyl or $C_{2-4}$alkenyl. More preferably, $R^2$ is $C_{1-2}$alkyl or —CH=CH$_2$. Most preferably, $R^2$ is ethyl or —CH=CH$_2$.

Preferably, $R^3$ is $C_{1-6}$alkyl or $(CH_2)_{0-3}C_{3-8}$cycloalkyl. More preferably, $R^3$ is $C_{1-4}$alkyl or $C_{3-6}$cycloalkyl. Most preferably, $R^3$ is $C_{3-4}$alkyl or $C_{5-6}$cycloalkyl. Especially, $R^3$ is $^i$propyl, $^s$butyl, $^t$butyl, cyclopentyl or cyclohexyl.

Preferably, M is $C_{2-12}$alkylene or $C_{2-12}$alkenylene, optionally substituted by $C_{1-6}$alkyl, and optionally containing an O atom. More preferably, M is $C_{2-8}$alkylene or $C_{2-8}$alkenylene, optionally substituted by $C_{1-4}$alkyl, and optionally containing an O atom. Most preferably, M is $C_{3-6}$alkylene or $C_{3-6}$alkenylene, optionally substituted by $C_{1-2}$alkyl, and optionally containing an O atom. Especially, M is $C_{4-5}$alkylene or $C_{4-5}$alkenylene, optionally substituted by methyl, and optionally containing an O atom. More especially, M is pentylene,

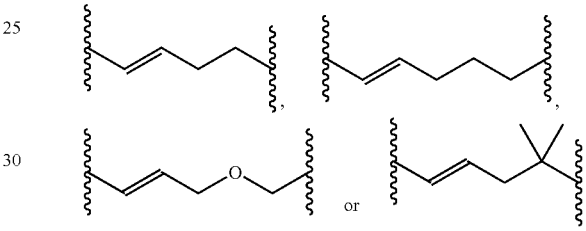

In another embodiment of the present invention, there is provided the compound of formula (Id):

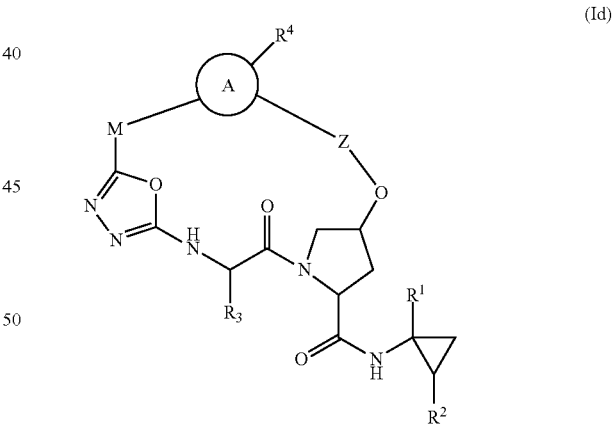

(Id)

or a pharmaceutically acceptable salt thereof,
wherein $R^1$, $R^2$, $R^3$, $R^4$, Z, M and A are as defined in relation to formula (I).

Preferably, $R^1$ is $C(O)NR^5SO_2R^5$ where $R^5$ is as defined in relation to formula (I). More preferably, $R^1$ is $C(O)NHSO_2R^5$ were $R^5$ is as defined in relation to formula (I). Most preferably, $R^1$ is $C(O)NHSO_2$—$C_{3-6}$cycloalkyl. Especially $R^1$ is $C(O)NHSO_2$-cyclopropyl.

Preferably, $R^2$ is $C_{2-6}$alkenyl. More preferably, $R^2$ is —CH=CH$_2$.

Preferably, $R^3$ is $C_{1-6}$alkyl or $(CH_2)_{0-3}C_{3-8}$cycloalkyl. More preferably, $R^3$ is $C_{1-4}$alkyl or $C_{3-6}$cycloalkyl. Most preferably, R³ is C₃₋₄alkyl or C₅₋₆cycloalkyl. Especially, R³ is ⁱpropyl, cyclopentyl or cyclohexyl.

Preferably, R⁴ is hydrogen, halo, hydroxy, C₁₋₆alkyl, C₁₋₆alkoxy, C₃₋₈cycloalkyl or aryl. More preferably, R⁴ is hydrogen, C₁₋₆alkyl or halo. Most preferably, R⁴ is hydrogen, ethyl or iodo.

When R⁴ is other than hydrogen, preferably A is pyridinyl.

Preferably, M is C₂₋₁₂alkylene or C₂₋₁₂alkenylene. More preferably, M is C₂₋₈alkylene or C₂₋₈alkenylene. Most preferably, M is C₃₋₆alkylene or C₃₋₆alkenylene. Especially, M is C₄₋₅alkylene or C₄₋₅alkenylene. More especially, M is butylene, pentylene or

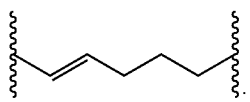

Preferably, A is a 9- or 10-membered fused heterobicyclic ring system containing 1 or 2 heteroatoms selected from N and O. More preferably, A is a 9- or 10-membered fused heterobicyclic ring system containing one N atom. Most preferably, A is quinolyl, isoquinolyl or isoindolyl.

In another embodiment of the present invention, there is provided the compound formula (Ie):

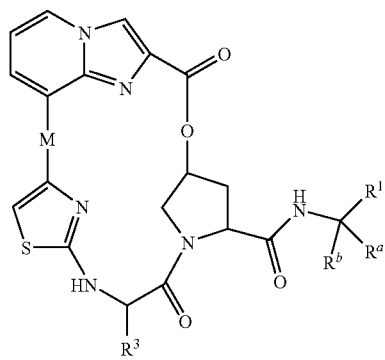

(Ie)

or a pharmaceutically acceptable salt thereof, wherein R¹, Rᵃ, Rᵇ, R³ and M are as defined in relation to formula (I).

Preferably, R¹ is C(O)NR⁵SO₂R⁵ where R⁵ is as defined in relation to formula (I). More preferably, R¹ is C(O)NHSO₂R⁵ where R⁵ is as defined in relation to formula (I). Most preferably, R¹ is C(O)NHSO₂—C₃₋₆cycloalkyl. Especially, R¹ is C(O)NHSO₂-cyclopropyl.

Preferably, Rᵃ is C₂₋₄alkylene-R² and Rᵇ is hydrogen, where R² is C₁₋₆alkyl optionally substituted by 1 to 3 halo. More preferably, Rᵃ is ethylene-R² and Rᵇ is hydrogen, where R² is C₁₋₄alkyl substituted by 1 to 3 fluoro. Examples of suitable R² groups include difluoromethyl and trifluoromethyl.

Preferably, Rᵃ and Rᵇ, together with the carbon atom to which they are attached, form a C₃₋₄cycloalkyl group, substituted by R², where R² is C₁₋₆alkyl or C₂₋₆alkenyl. More preferably, Rᵃ and Rᵇ, together with the carbon atom to which they are attached, form a cyclopropyl group, substituted by R², where R² is C₁₋₄alkyl or C₂₋₄alkenyl. Examples of suitable R² groups include methyl, ethyl and ethenyl.

In another embodiment of the present invention, there is provided the compound of formula (If):

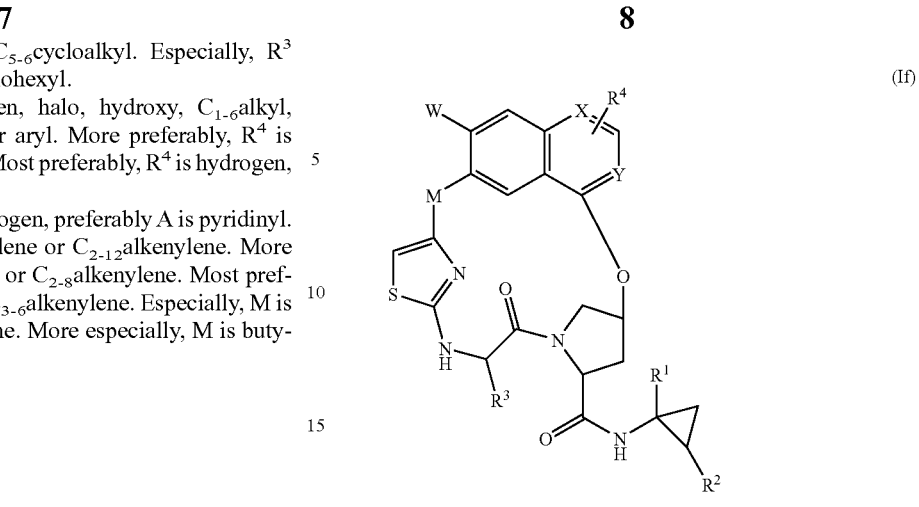

(If)

or a pharmaceutically acceptable salt thereof, wherein R¹, R², R³, R⁴, M and W are as defined in relation to formula (I);
X is N when Y is CH; and
X is CH when Y is N.

Preferably, R¹ is C(O)NR⁵SO₂R⁵ where R⁵ is as defined in relation to formula (I). More preferably, R¹ is C(O)NHSO₂R⁵ where R⁵ is as defined in relation to formula (I). Most preferably, R¹ is C(O)NHSO₂—C₃₋₆cycloalkyl. Especially, R¹ is C(O)NHSO₂-cyclopropyl.

Preferably, R² is C₂₋₆alkenyl. More preferably, R² is —CH=CH₂.

Preferably, R³ is C₁₋₆alkyl or (CH₂)₀₋₃C₃₋₈cycloalkyl. More preferably, R³ is C₁₋₄alkyl or C₃₋₆cycloalkyl. Most preferably, R³ is C₂₋₄alkyl or C₅₋₆cycloalkyl. Especially, R³ is ˢbutyl, cyclopentyl or cyclohexyl.

Preferably, R⁴ is hydrogen, halo, hydroxy, C₁₋₆alkyl, C₁₋₆alkoxy, C₃₋₈cycloalkyl or aryl. More preferably, R⁴ is hydrogen, C₁₋₆alkyl, C₁₋₆alkoxy or aryl. Most preferably, R⁴ is hydrogen, C₁₋₄alkyl, C₁₋₄alkoxy or phenyl. Especially, R⁴ is hydrogen, C₁₋₂alkyl, C₁₋₂alkoxy or phenyl. More especially, R⁴ is hydrogen, ethyl, methoxy or phenyl.

Preferably, M is C₂₋₈alkylene or C₂₋₈alkenylene, optionally substituted by C₁₋₆alkyl. More preferably, M is C₃₋₆alkylene or C₃₋₆alkenylene, optionally substituted by C₁₋₄alkyl. Most preferably, M is C₄₋₅alkylene or C₄₋₅alkenylene, optionally substituted by C₁₋₂alkyl. Especially, M is butylene,

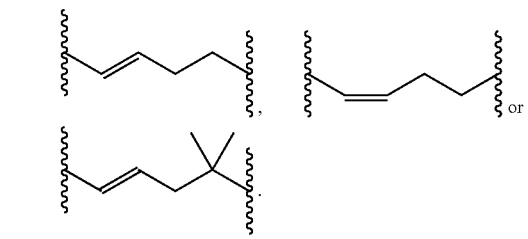

Preferably, W is halo, OR⁵, C₁₋₆alkyl, CN, NO₂, CF₃, CO₂R⁵ or CON(R⁵)₂, where R⁵ is as defined in relation to formula (I). More preferably, W is fluoro, chloro, OC₁₋₆alkyl, CN, NO₂ or CF₃. Most preferably, W is fluoro, chloro or OC₁₋₄alkyl. Especially, W is methoxy.

When any variable occurs more than one time in formula (I) or in any substituent, its definition on each occurrence is independent of its definition at every other occurrence.

As used herein, the term "alkyl" as a group or part of a group refers to any linear or branched chain alkyl group having a number of carbon atoms in the specified range. Thus, for example, "$C_{1-6}$alkyl" refers to all of the hexyl alkyl and pentyl alkyl isomers as well as n-, iso-, sec- and t-butyl, n- and iso-propyl, ethyl and methyl. As another example, "$C_{1-4}$ alkyl" refers to n-, iso-, sec- and t-butyl, n- and iso-propyl, ethyl and methyl.

The term "alkoxy" represents any linear or branched chain alkyl group having a number of carbon atoms in the specified range and attached through an oxygen bridge. Examples of suitable alkoxy groups include methoxy, ethoxy, n-propoxy, i-propoxy, n-butoxy, s-butoxy, i-butoxy and t-butoxy.

The term "alkenyl" as a group or part of a group refers to any linear or branched chain alkyl group containing at least one double bond, which may occur at any point along the chain, and having a number of carbon atoms in the specified range. E- and Z-forms are both included, where applicable. Examples of suitable alkenyl groups include vinyl, allyl, butenyl and pentenyl.

The term "cycloalkyl" refers to any cyclic alkyl ring having a number of carbon atoms in the specified range. Examples of suitable cycloalkyl groups include cyclopropyl, cyclobutyl, cyclopentyl and cyclohexyl.

The terms "alkylene" and "alkenylene" as a group or part of a group refer to the groups "alkyl" and "alkenyl" respectively, when they are divalent, i.e. attached at two atoms.

The term "halogen" or "halo" means fluorine, chlorine, bromine and iodine (alternatively referred to as fluoro, chloro, bromo and iodo, respectively).

The term "aryl" as a group or part of a group means a carbocyclic aromatic ring. Examples of suitable aryl groups include phenyl and naphthyl.

The term "Het" as a group or part of a group means a 5- to 7-membered saturated or unsaturated non-aromatic ring having 1 to 4 heteroatoms selected from N, O and S.

The term "heteroaryl" as a group or part of a group means a 5- to 10-membered heteroaromatic ring system containing 1 to 4 heteroatoms selected from N, O and S. Examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indolyl, benzothienyl, benzimidazolyl, benzofuryl, quinolyl and isoquinolyl.

Unless expressly stated to the contrary, all ranges cited herein are inclusive. For example, a heteroaryl ring described as containing from "1 to 3 heteroatoms" means the ring can contain 1, 2, or 3 heteroatoms.

Where a compound or group is described as "optionally substituted" one or more substituents may be present. Furthermore, optional substituents may be attached to the compounds or groups which they substitute in a variety of ways, either directly or through a connecting group of which the following are examples: amine, amide, ester, ether, thioether, sulfonamide, sulfamide, sulfoxide, urea, thiourea and urethane. As appropriate an optional substituent may itself be substituted by another substituent, the latter being connected directly to the former or through a connecting group such as those exemplified above.

Specific compounds within the scope of this invention include those named in the Examples and Tables hereinbelow and their pharmaceutically acceptable salts.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulfonic acid, maleic acid, succinic acid, acetic acid, citric acid, tartaric acid, carbonic acid, phosphoric acid or sulfuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulfate ester, or reduction or oxidation of a susceptible functionality.

The present invention includes within its scope solvates of the compounds of formula (I) and salts thereof, for example, hydrates.

The present invention also includes within its scope any enantiomers, diastereomers, geometric isomers and tautomers of the compounds of formula (I). It is to be understood that all such isomers and mixtures thereof are encompassed within the scope of the invention.

The preferred compounds of the present invention will have the stereochemistry as shown in formula (Ig):

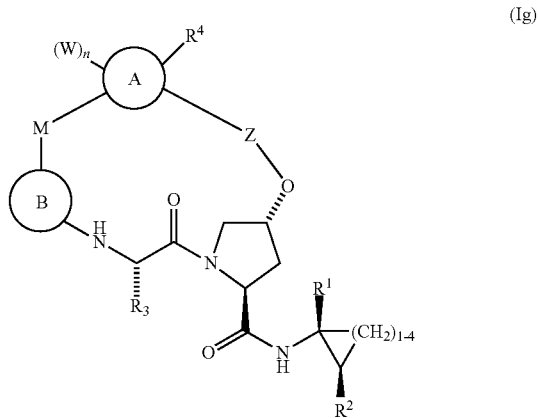

The present invention further provides a compound of formula (I) or a pharmaceutically acceptable salt thereof for use in therapy.

In another aspect, the invention provides the use of a compound of formula (I) as defined above, or a pharmaceutically acceptable salt thereof, for the manufacture of a medicament for treatment or prevention of infection by hepatitis C virus in a human or animal.

A further aspect of the invention provides a pharmaceutical composition comprising a compound of formula (I) as defined above, or a pharmaceutically acceptable salt thereof, in association with a pharmaceutically acceptable carrier. The composition may be in any suitable form, depending on the intended method of administration. It may for example be in the form of a tablet, capsule or liquid for oral administration, or of a solution or suspension for administration parenterally.

The pharmaceutical compositions optionally also include one or more other agents for the treatment of viral infections such as an antiviral agent, or an immunomodulatory agent such as α-, β- or γ-interferon.

In a further aspect, the invention provides a method of inhibiting hepatitis C virus protease and/or of treating or preventing an illness due to hepatitis C virus, the method involving administering to a human or animal (preferably mammalian) subject suffering from the condition a therapeutically or prophylactically effective amount of the pharmaceutical composition described above or of a compound of formula (I) as defined above, or a pharmaceutically acceptable salt thereof. "Effective amount" means an amount sufficient to cause a benefit to the subject or at least to cause a change in the subject's condition.

The term "subject" (alternatively referred to herein as "patient") as used herein refers to an animal, preferably a mammal, most preferably a human, who has been the object of treatment, observation or experiment.

The dosage rate at which the compound is administered will depend on a variety of factors including the activity of the specific compound employed, the metabolic stability and length of action of that compound, the age of the patient, body weight, general health, sex, diet, mode and time of administration, rate of excretion, drug combination, the severity of the particular condition and the host undergoing therapy. Suitable dosage levels may be of the order of 0.02 to 5 or 10 g per day, with oral dosages two to five times higher. For instance, administration of from 10 to 50 mg of the compound per kg of body weight from one to three times per day may be in order. Appropriate values are selectable by routine testing. The compound may be administered alone or in combination with other treatments, either simultaneously or sequentially. For instance, it may be administered in combination with effective amounts of antiviral agents, immunomodulators, anti-infectives or vaccines known to those of ordinary skill in the art. It may be administered by any suitable route, including orally, intravenously, cutaneously and subcutaneously. It may be administered directly to a suitable site or in a manner in which it targets a particular site, such as a certain type of cell. Suitable targeting methods are already known.

An additional aspect of the invention provides a method of preparation of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

As noted above, the present invention also relates to a method of inhibiting HCV NS3 protease, inhibiting HCV replication, or preventing or treating HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such therapeutic agents active against HCV include ribavirin, levovirin, viramidine, thymosin alpha-1, interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes recombinant interferon-α2a (such as ROFERON interferon available from Hoffmann-LaRoche, Nutley, N.J.), pegylated interferon-α2a (PEGASYS), interferon-α2b (such as INTRON-A interferon available from Schering Corp., Kenilworth, N.J.), pegylated interferon α2b (PEGINTRON), a recombinant consensus interferon (such as interferon alphacon-1), and a purified interferon-α product. Amgen's recombinant consensus interferon has the brand name INFERGEN. LEVOVIRIN is the L-enantiomer of ribavirin which has shown immunomodulatory activity similar to ribavirin. Viramidine represents an analog of ribavirin disclosed in WO 01/60379 (ICN Pharmaceuticals). In accordance with the method of the present invention, the individual components of the combination can be administered separately at different times during the course of therapy or concurrently in divided or single combination forms.

For the treatment of HCV infection, the compounds of the present invention may also be administered in combination with an agent that is an inhibitor of HCV NS3 serine protease. HCV NS3 protease inhibitors are disclosed in WO 98/22496, WO 98/46630, WO 99/07733, WO 99/07734, WO 99/38888, WO 99/50230, WO 99/64442, WO 00/09543, WO 00/59929, GB-2337262, WO 02/48116, WO 02/48172, and U.S. Pat. No. 6,323,180.

Ribavirin, levovirin, and viramidine may exert their anti-HCV effects by modulating intracellular pools of guanine nucleotides via inhibition of the intracellular enzyme inosine monophosphate dehydrogenase (IMPDH). Thus, inhibition of IMPDH represents another useful target for the discovery of inhibitors of HCV replication. Therefore, the compounds of the present invention may also be administered in combination with an inhibitor of IMPDH, such as VX-497, disclosed in WO 97/41211 and WO 01/00622 (Vertex); another IMPDH inhibitor, such as that disclosed in WO 00/25780 (Bristol-Myers Squibb); or mycophenolate mofetil [see A. C. Allison and E. M. Eugui, *Agents Action,* 44 (Suppl.): 165 (1993)].

For the treatment of HCV infection, the compounds of the present invention may also be administered in combination with the antiviral agent amantadine (1-aminoadamantane) [see J. Kirschbaum, *Anal. Profiles Drug Subs.* 12: 1-36 (1983)].

The compounds of the present invention may also be combined for the treatment of HCV infection with antiviral 2'-C-branched ribonucleosides disclosed in R. E. Harry-O'kuru, et al., *J. Org. Chem.* 62: 1754-1759 (1997); M. S. Wolfe, et al., *Tetrahedron Lett.,* 36: 7611-7614 (1995); U.S. Pat. No. 3,480, 613; WO 01/90121; WO 01/92282; WO 02/32920; WO 04/002999; WO 04/003000; and WO 04/002422. Such 2'-C-branched ribonucleosides include 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine, and the corresponding amino acid ester of the ribose C-2', C-3', and C-5' hydroxyls and the corresponding optionally substituted cyclic 1,3-propanediol esters of the 5'-phosphate derivatives.

The compounds of the present invention may also be combined for the treatment of HCV infection with other nucleosides having anti-HCV properties, such as those disclosed in WO 02/51425 (Mitsubishi Pharma Corp.); WO 01/79246, WO 02/32920 and WO 02/48165 (Pharmasset, Ltd.); WO 01/68663 (ICN Pharmaceuticals); WO 99/43691; WO 02/18404 (Hoffmann-LaRoche); U.S. 2002/0019363; WO 02/100415; WO 03/026589; WO 03/026675; WO 03/093290; US 2003/0236216; US 2004/0006007; WO 04/011478; WO 04/013300; US 2004/0063658; and WO 04/028481.

For the treatment of HCV infection, the compounds of the present invention may also be administered in combination with an agent that is an inhibitor of HCV NS5B polymerase. Such HCV NS5B polymerase inhibitors that may be used as combination therapy include those disclosed in WO 02/057287, U.S. Pat. No. 6,777,395, WO 02/057425, US 2004/0067901, WO 03/068244, WO 2004/000858, WO 04/003138 and WO 2004/007512. Other such HCV polymerase inhibitors include valopicitabine (NM-283; Idenix) and 2'-F-2'-beta-methylcytidine (see also WO 2005/003147, assigned to Pharmasset, Ltd.).

The compounds of the present invention may also be combined for the treatment of HCV infection with non-nucleoside inhibitors of HCV polymerase such as those disclosed in WO 01/77091 (Tularik, Inc.); WO 01/47883 (Japan Tobacco, Inc.); WO 02/04425 (Boehringer Ingelheim); WO 02/06246, WO 03/062211, WO 2004/087714, WO 2004/110442, WO 2005/034941, WO 2005/023819, WO2006/029912, WO 2006/008556 and WO 2006/027628 (all Istituto di Ricerche di Biologia Moleculare P. Angeletti S.p.A.); WO 02/20497; WO 2005/016927 (in particular JTK003), and WO 2005/080399 (Japan Tobacco, Inc.); WO 2006/020082 (Bristol-Myers Squibb Company); and HCV-796 (Viropharma Inc.).

The present invention also provides a process for the preparation of compounds of formula (I).

According to a general process (a), compounds of formula (I) may be prepared by the coupling of the ester of formula (II) with the amine of formula (III):

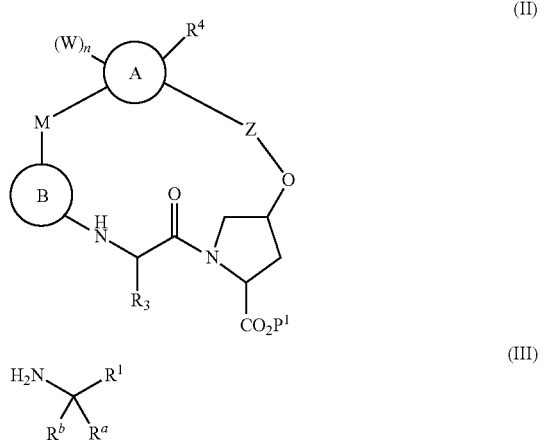

where n, $R^1$, $R^a$, $R^b$, $R^3$, $R^4$, M, W, X, Z, and rings A and B are as defined in relation to formula (I) and $P^1$ is $C_{1-6}$alkyl, such as methyl. The reaction is conveniently carried out in the presence of a coupling reagent, such as TBTU or HATU, and a base, such as diisopropylethylamine or triethylamine, in a solvent. Suitable solvents include DMF and dichloromethane.

The compound of formula (II) where M has 4 or more carbon atoms in the tether and one or more double bonds may be prepared by the internal ring closure of the diene of formula (IV):

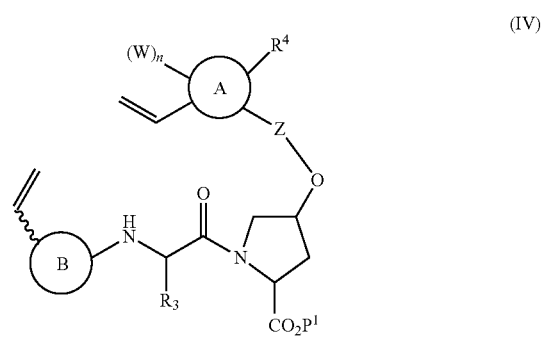

where n, $R^3$, $R^4$, W, X, Z, and rings A and B are as defined in relation to formula (I) and $P^1$ is as defined in relation to formula (II). The reaction is conveniently carried out in the presence of a metathesis catalyst, such as Zhan catalyst [dichloro(5-chloro-2-isopropoxybenzylidene)(1,3-dimethylimidazolidin-2-ylidene)ruthenium], preferably at raised temperature, in a suitable solvent such as 1,2-dichloroethane. The resultant ring double bond may be hydrogenated to give a further compound of formula (II). The hydrogenation is preferably carried out in the presence of a suitable catalyst, such as palladium on carbon, in a suitable solvent, such as methanol/ethyl acetate mixture.

Compounds of formulae (II), (III) and (IV) are either well known in the art or may be prepared by conventional methodology well known to one of ordinary skill in the art using, for instance, procedures described in the accompanying Schemes and Examples, or by alternative procedures which will be readily apparent.

Further details of suitable procedures will be found in the accompanying Schemes and Examples. For instance compounds of formula (I) can be converted into other compounds of formula (I) using synthetic methodology well known in the art.

Thus, for instance, the compound of formula (I) where M is unsaturated may be converted into the compound of formula (I) where M is saturated by hydrogenation, preferably in the presence of a suitable catalyst, such as palladium on carbon, in a suitable solvent, such as methanol/ethyl acetate mixture.

The compounds of the present inventions are useful in the inhibition of HCV protease (e.g., HCV NS3 protease) and the prevention or treatment of infection by HCV. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HCV protease, e.g., by competitive inhibition. Thus the compounds of this invention are commercial products to be sold for these purposes.

General Description of Synthesis:

The compounds of the present invention may be synthesised as outlined in the general Schemes 1, 2, 3, 4 and 5.

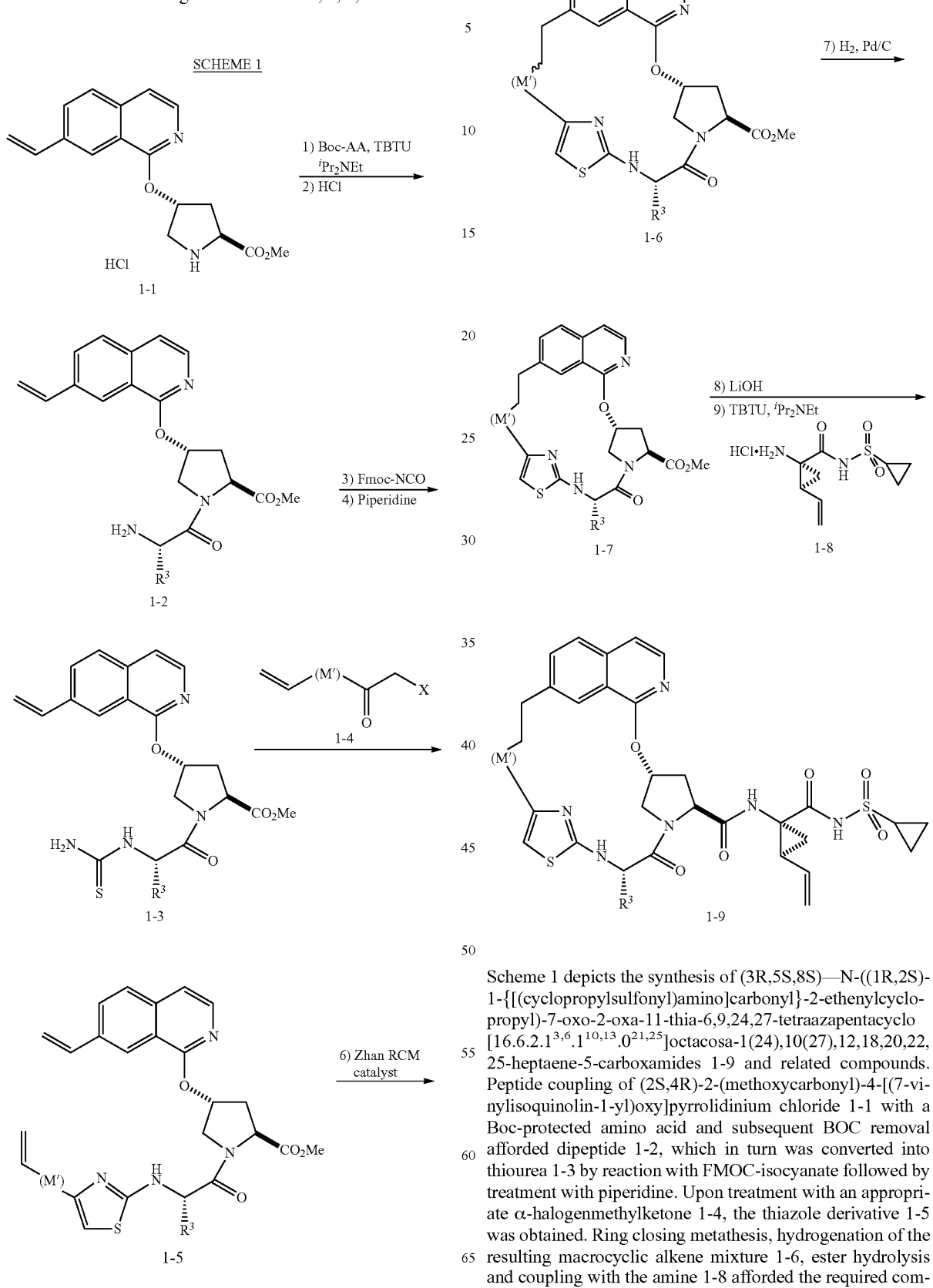

Scheme 1 depicts the synthesis of (3R,5S,8S)—N-((1R,2S)-1-{[(cyclopropylsulfonyl)amino]carbonyl}-2-ethenylcyclopropyl)-7-oxo-2-oxa-11-thia-6,9,24,27-tetraazapentacyclo[16.6.2.1$^{3,6}$.1$^{10,13}$.0$^{21,25}$]octacosa-1(24),10(27),12,18,20,22,25-heptaene-5-carboxamides 1-9 and related compounds. Peptide coupling of (2S,4R)-2-(methoxycarbonyl)-4-[(7-vinylisoquinolin-1-yl)oxy]pyrrolidinium chloride 1-1 with a Boc-protected amino acid and subsequent BOC removal afforded dipeptide 1-2, which in turn was converted into thiourea 1-3 by reaction with FMOC-isocyanate followed by treatment with piperidine. Upon treatment with an appropriate α-halogenmethylketone 1-4, the thiazole derivative 1-5 was obtained. Ring closing metathesis, hydrogenation of the resulting macrocyclic alkene mixture 1-6, ester hydrolysis and coupling with the amine 1-8 afforded the required compound 1-9.

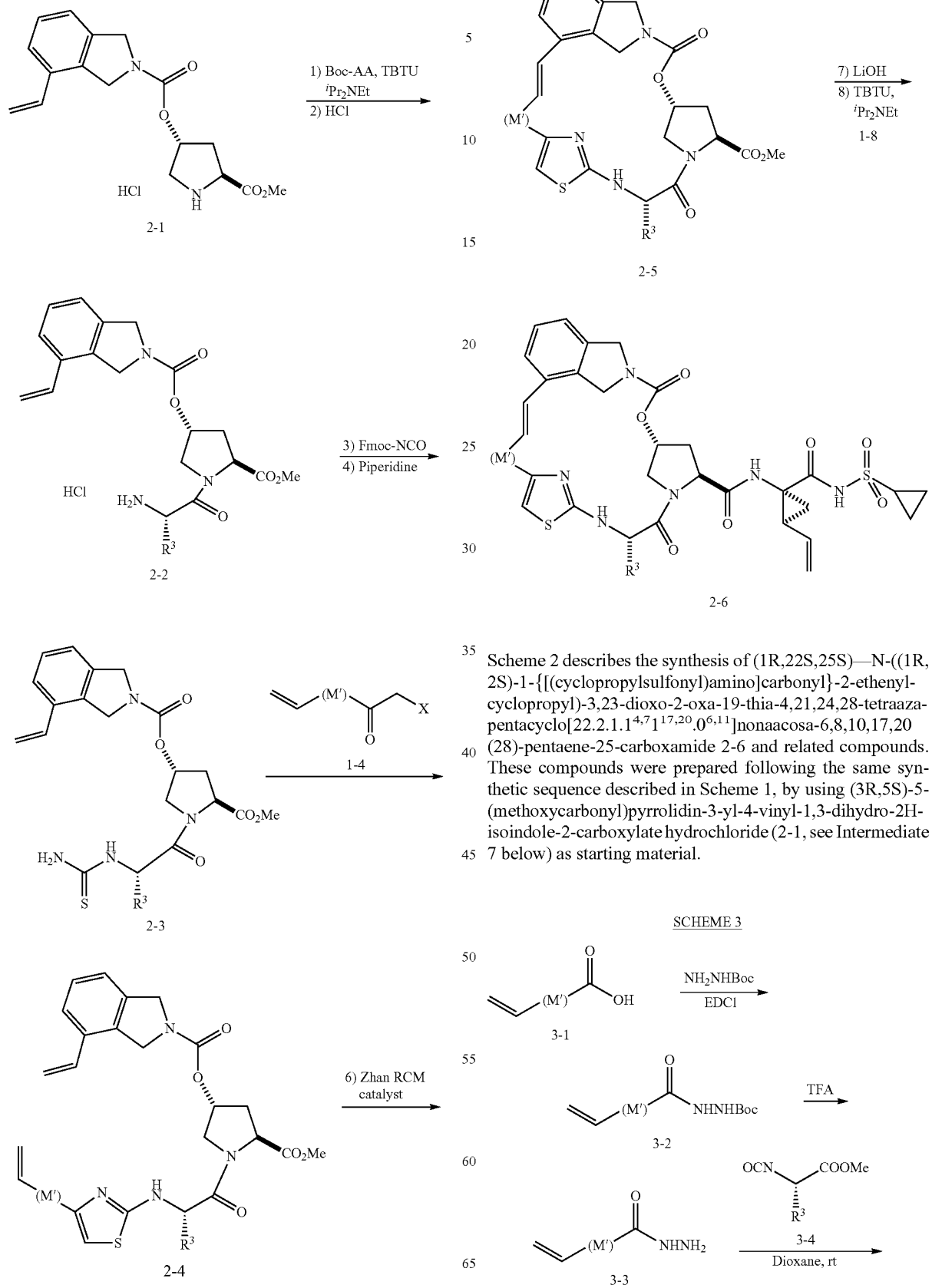

Scheme 2 describes the synthesis of (1R,22S,25S)—N-((1R, 2S)-1-{[(cyclopropylsulfonyl)amino]carbonyl}-2-ethenylcyclopropyl)-3,23-dioxo-2-oxa-19-thia-4,21,24,28-tetraazapentacyclo[22.2.1.1$^{4,7}$1$^{17,20}$.0$^{6,11}$]nonaacosa-6,8,10,17,20 (28)-pentaene-25-carboxamide 2-6 and related compounds. These compounds were prepared following the same synthetic sequence described in Scheme 1, by using (3R,5S)-5-(methoxycarbonyl)pyrrolidin-3-yl-4-vinyl-1,3-dihydro-2H-isoindole-2-carboxylate hydrochloride (2-1, see Intermediate 7 below) as starting material.

19
-continued

20
-continued

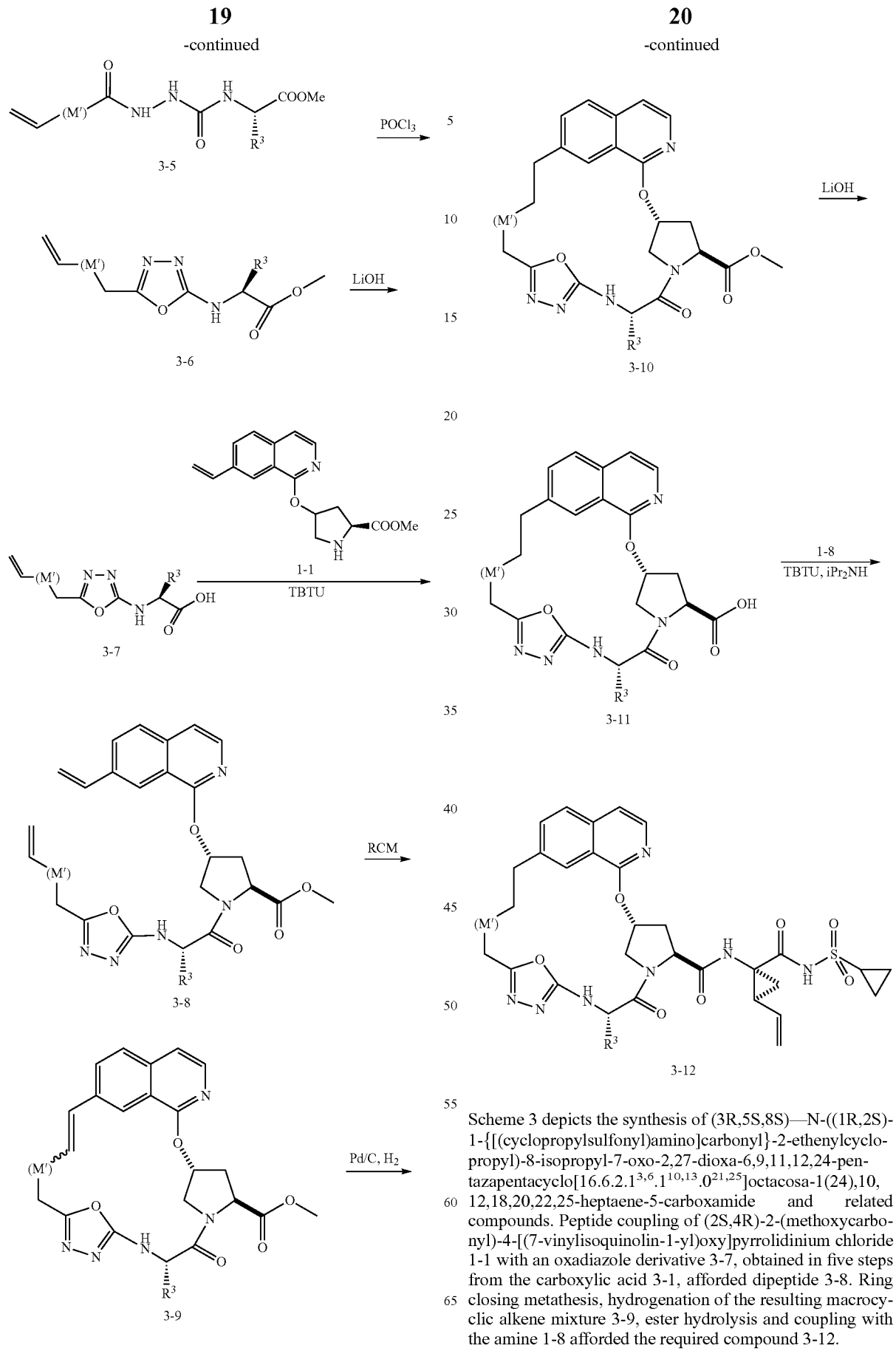

Scheme 3 depicts the synthesis of (3R,5S,8S)—N-((1R,2S)-1-{[(cyclopropylsulfonyl)amino]carbonyl}-2-ethenylcyclopropyl)-8-isopropyl-7-oxo-2,27-dioxa-6,9,11,12,24-pentazapentacyclo[16.6.2.1$^{3,6}$.1$^{10,13}$.0$^{21,25}$]octacosa-1(24),10,12,18,20,22,25-heptaene-5-carboxamide and related compounds. Peptide coupling of (2S,4R)-2-(methoxycarbonyl)-4-[(7-vinylisoquinolin-1-yl)oxy]pyrrolidinium chloride 1-1 with an oxadiazole derivative 3-7, obtained in five steps from the carboxylic acid 3-1, afforded dipeptide 3-8. Ring closing metathesis, hydrogenation of the resulting macrocyclic alkene mixture 3-9, ester hydrolysis and coupling with the amine 1-8 afforded the required compound 3-12.

SCHEME 4 (describing Entries 6-13, Table 3)
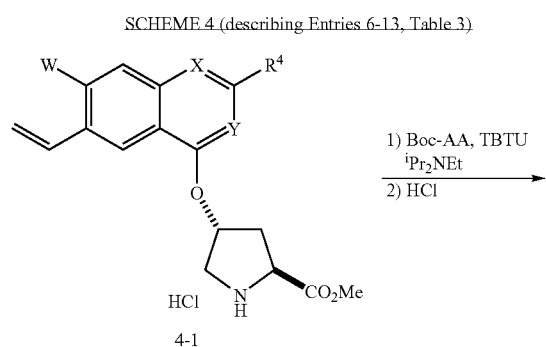
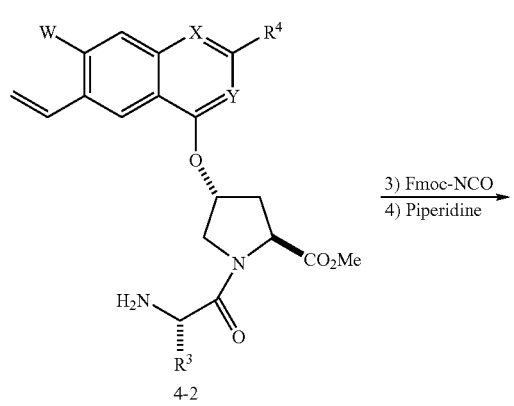
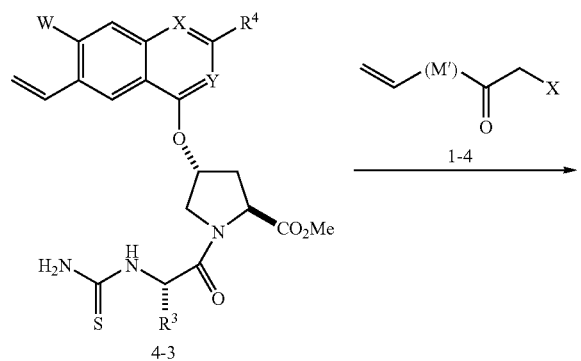
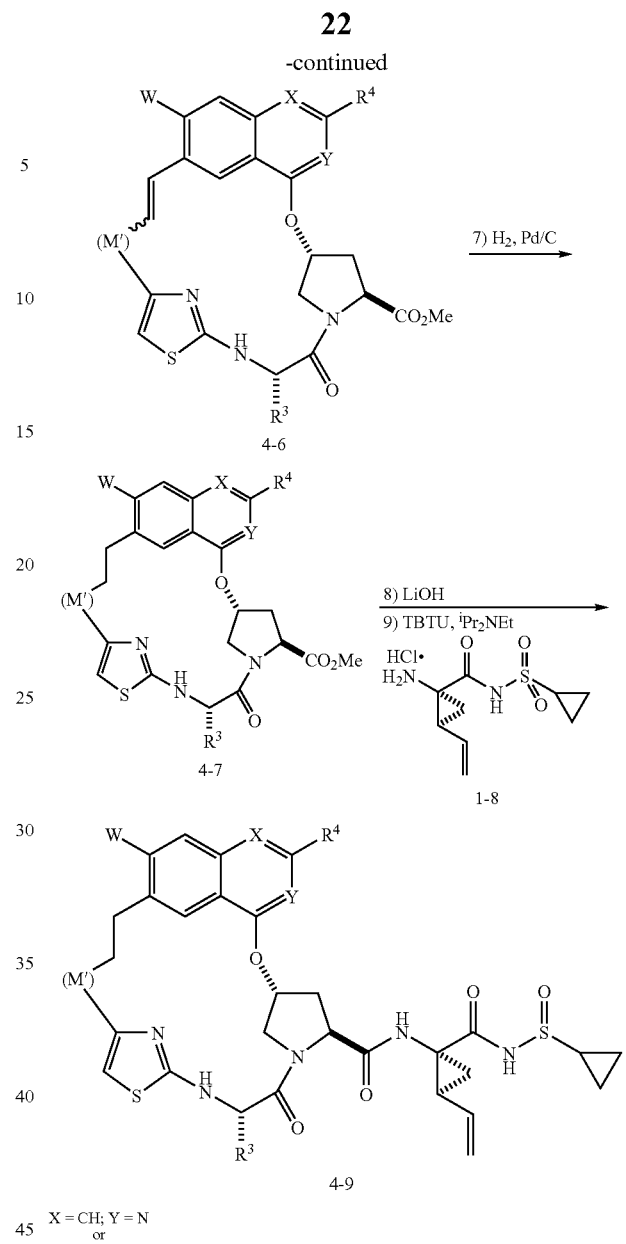
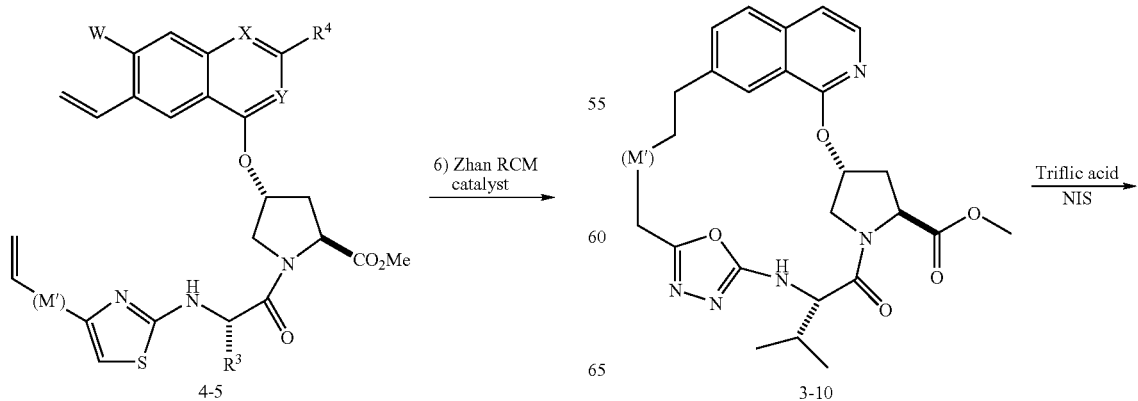
SCHEME 5 (describing Entry 16, Table 3)

-continued

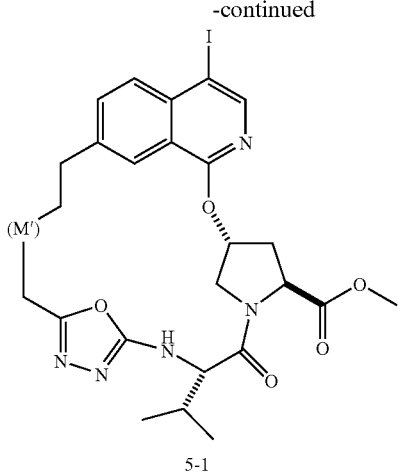

5-1

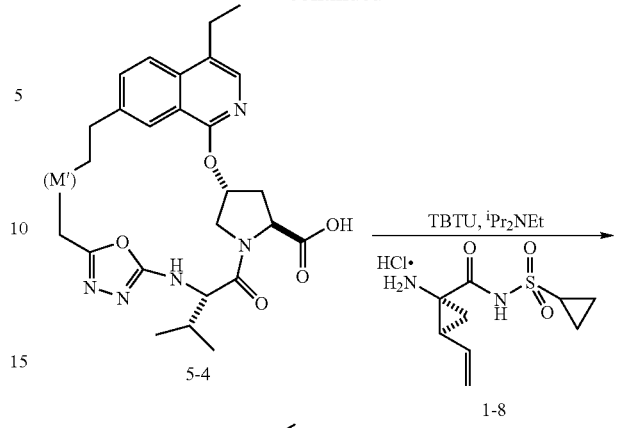

5-4

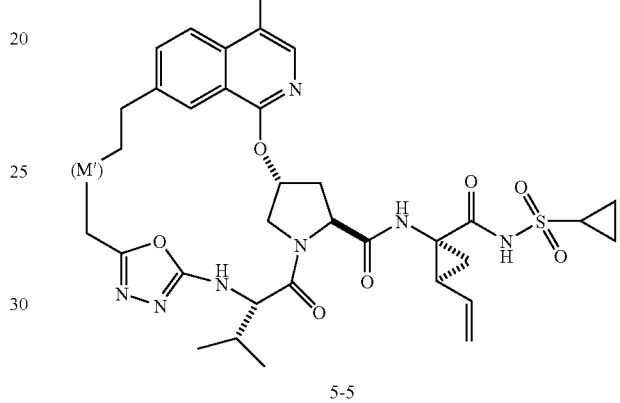

5-5

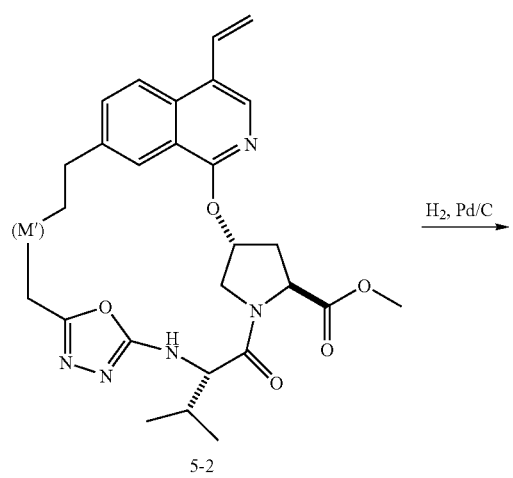

5-2

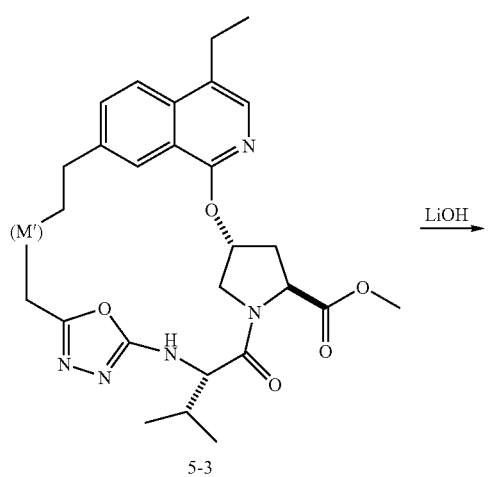

5-3

During any of the above synthetic sequences, it may be necessary and/or desirable to protect sensitive or reactive groups on any of the molecules concerned. This may be achieved by means of conventional protecting groups such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, $3^{rd}$ ed., 1999. The protecting groups may be removed at a convenient subsequent stage using methods known from the art.

The HCV NS3 protease inhibitory activity of the present compounds may be tested using assays known in the art. One such assay is HCV NS3 protease time-resolved fluorescence (TRF) assay described as follows:

HCV NS3 Protease Time-Resolved Fluorescence (TRF) Assay

The NS3 protease TRF assay was performed in a final volume of 100 µl in assay buffer containing 50 mM HEPES, pH 7.5, 150 mM NaCl, 15% glycerol, 0.15% Triton X-100, 10 mM DTT, and 0.1% PEG 8000. The NS3 protease was pre-incubated with various concentrations of inhibitors for 10-30 minutes. The peptide substrate for the assay is Ac-C(Eu)-DDMEE-Abu-[COO]-XSAK(QSY7)-NH2, where Eu is an europium-labeled group, Abu is 1-aminobutanoic acid which connects an ester linkage with 2-hydroxy propanoic acid (X). Hydrolysis of the peptide by NS3 protease activity causes in separation of the fluorophore from the quencher, resulting in an increase in fluorescence. Activity of the protease was initiated by adding the TRF peptide substrate (final concentration 50-100 nM). The reaction was quenched after 1 hour at room temperature with 100 µl of 500 mM MES, pH 5.5. Product fluorescence was detected using either a Victor V2 or FUSION fluorimeter (Perkin Elmer Life and Analytical Sciences) with excitation at 340 nm and emission at 615 nm with 50-400 us delay. Testing concentrations of different enzyme forms was selected with a signal to background ratio of 10-30. The inhibition constants were derived using a four-parameter fit.

Another suitable assay is the cellular REPLICON or rheplisa assay described as follows:

Cell Based HCV Replication Assay

Cell clones that stably maintain subgenomic HCV replicon were obtained by transfecting Huh-7 cells with an RNA replicon identical to $I_{377}$neo/NS3-37 wt described by Lohmann et al. (1999) EMBL-GENBANK No. AJ242652), followed by selection with neomycin sulfate (G418). Viral replication was monitored by measuring the expression of the NS3 protein by an ELISA assay performed directly on cells grown in 96 wells microtiter plates (Cell-ELISA) using the anti-NS3 monoclonal antibody 10E5/24 (as described in published International patent application WO 02/59321). Cells were seeded into 96 well plates at a density of $10^4$ cells per well in a final volume of 0.1 ml of DMEM/10% FCS. Two hours after plating, 50 μl of DMEM/10% FCS containing a 3× concentration of inhibitor were added, cells were incubated for 96 hours and then fixed for 10 minutes with ice-cold isopropanol. Each condition was tested in duplicate and average absorbance values were used for calculations. The cells were washed twice with PBS, blocked with 5% non-fat dry milk in PBS+0.1% TRITON X100+0.02% SDS (PBSTS) and then incubated o/n at 4° C. with the 10E5/24 mab diluted in Milk/PBSTS. After washing 5 times with PBSTS, the cells were incubated for 3 hours at room temperature with Fc specific anti-mouse IgG conjugated to alkaline phosphatase (SIGMA), diluted in Milk/PBSTS. After washing again as above, the reaction was developed with p-nitrophenyl phosphate disodium substrate (SIGMA) and the absorbance at 405/620 nm read at intervals. For calculations, we used data sets where samples incubated without inhibitors had absorbance values comprised between 1 and 1.5. The inhibitor concentration that reduced by 50% the expression of NS3 ($IC_{50}$) was calculated by fitting the data to the Hill equation, Fraction inhibition=$1-(Ai-b)/(A_0-b)=[I]^n/([I]^n+IC_{50})$ where:
  Ai=absorbance value of HBI10 cells supplemented with the indicated inhibitor concentration.
  $A_0$=absorbance value of HBI10 cells incubated without inhibitor.
  b=absorbance value of Huh-7 cells plated at the same density in the same microtiter plates and incubated without inhibitor.
  n=Hill coefficient.

The compounds of the present invention were active in the cell based HCV replication assay with activities<50 μM, and especially <5 μM.

Other examples of such assays are described in e.g., International published patent application WO2005/046712. Compounds useful as HCV NS3 protease inhibitors would have a Ki less than 50 μM, more preferably less than 10 μM, most preferably less than 1 μM, especially less than 100 nM, and more especially less than 50 nM.

The following examples serve to illustrate the invention and its practice.

$^1$H NMR spectra were recorded on BRUKER AM series spectrometers operating at (reported) frequencies between 300 and 600 MHz. Chemical shifts (δ) for signals corresponding to non-exchangeable protons (and exchangeable protons where visible) are recorded in parts per million (ppm) relative to tetramethylsilane and are measured using the residual solvent peak as reference. Signals are tabulated in the order: multiplicity (s, singlet; d, doublet; t, triplet; q, quartet; m, multiplet; b, broad, and combinations thereof); coupling constant(s) in Hertz (Hz); number of protons. Mass spectral (MS) data were obtained on a PERKIN ELMER API 100, or WATERS MICROMASS ZQ, operating in negative ($ES^{31}$) or positive ($ES^+$) ionization mode and results are reported as the ratio of mass over charge (m/z). Preparative scale HPLC separations were carried out on a WATERS MICROMASS System incorporating a 2525 pump module, a MICROMASS ZMD detector and a 2767 collection module, under FRACTION LINX software or on a SHIMADZU preparative system.

The following abbreviations are used in the examples, the schemes and the tables: AcOH: acetic acid; dioxan(e): 1,4-dioxane; DIPEA or $^iPr_2NEt_2$: diisopropylethylamine; DCE: 1,2-dichloroethane; DCM: dichloromethane; DMF: N,N-dimethylformamide; DMSO: dimethylsulfoxide; $Et_2O$: diethyl ether; EtOAc: ethyl acetate; eq.: equivalent(s); h: hour(s); HATU: O-(7-azabenzotriazol-1-yl)-N,N,N',N'-tetramethyluronium hexafluorophosphate; MeCN: acetonitrile; MeOH: methanol; min: minutes; MS: mass spectrum; PE: petroleum ether 30/60; quant.: quantitative; RP-HPLC: reversed phase high-pressure liquid chromatography; RP-MS-HPLC: mass-guided reversed phase high-pressure liquid chromatography; RT: room temperature; sat. aq.: saturated aqueous; TBTU: O-benzotriazol-1-yl-N,N,N',N'-tetramethyluronium tetrafluoroborate; THF: tetrahydrofuran.

Intermediate 1: (2S,4R)-2-(methoxycarbonyl)-4-[(7-vinylisoquinolin-1-yl)oxy]pyrrolidinium chloride Step 1: 1-tert-butyl 2-methyl (2S,4R)-4-[(7-bromoisoquinolin-1-yl)oxy]pyrrolidine-1,2-dicarboxylate To a 0.2 mM solution of trans 4-hydroxy L-BOC-proline (1 eq) in DMSO at RT was added $^tBuOK$ (3 eq) in a single portion. The reaction mixture was stirred at RT for 30 min, cooled to 10° C. and 7-bromo-1-chloroisoquinoline was added (1 eq). The resulting mixture was allowed to warm to RT and stirred overnight. The organic layer was washed with sat. aq. citric acid solution, water and brine and the aqueous phases were back extracted with EtOAc. The combined organic phases were dried ($Na_2SO_4$) and the solvent evaporated under reduced pressure to give a dark solid. The solid was dissolved in MeOH and to the stirred solution an excess (4 eq) of 2.0 M trimethylsilyldiazomethane in hexanes was added dropwise at 15° C. The resulting mixture was stirred for 15 min after gas evolution has ceased. Volatiles were removed by rotary evaporation and the residue was purified by flash chromatography ($SiO_2$, PE/EtOAc 8/2 v/v as eluent) to give title product as a solid. MS ($ES^+$) $C_{20}H_{23}BrN_2O_5$ requires 451. Found: 452 ($M+H^+$).

Step 2: 1-tert-butyl 2-methyl (2S,4R)-4-[(7-vinylisoquinolin-1-yl)oxy]pyrrolidine-1,2-dicarboxylate Aryl bromide from Step 1 was dissolved in toluene (about 0.15 mM solution) and treated with tributylvinyltin (1.5 eq) and $[Ph_3P]_4Pd(0)$ (0.05 eq). The reaction mixture was stirred at 100° C. under $N_2$ atmosphere for 2 h. After cooling to RT, the reaction mixture was poured into EtOAc and washed with brine. The organic phase was separated, dried ($Na_2SO_4$) and concentrated under reduced pressure. The residue was purified by flash chromatography ($SiO_2$, PE/EtOAc 8/2 v/v as eluent) to give the title compound as a viscous oil. MS (ES$^+$) $C_{22}H_{26}N_2O_5$ requires 398. Found: 399 (M+H$^+$).

Step 3: (2S,4R)-2-(methoxycarbonyl)-4-[(7-vinylisoquinolin-1-yl)oxy]pyrrolidinium chloride Carbamate from Step 2 was dissolved in a 4.0 M HCl solution in dioxane. The resulting mixture was stirred at RT for 0.5 h, during which time the product precipitated. The title compound was filtered off and washed with hexane/EtOAc 1/1 v/v. MS (ES$^+$) $C_{17}H_{18}N_2O_3$ requires 298. Found: 299 (M+H$^+$).

Intermediate 2: (1R,2S)-1-amino-N-(cyclopropylsulfonyl)amino-2-ethylcyclopropane carboxamide hydrochloride Step 1: tert-butyl ((1R,2R)-1-{[(cyclopropylsulfonyl)amino]carbonyl}-2-ethylcyclopropyl)carbamate A hydrogenation vessel was charged with a solution of tert-butyl ((1R,2S)-1-{[(cyclopropylsulfonyl)amino]carbonyl}-2-vinylcyclopropyl)carbamate (prepared as described in WO 03/099274) followed by Ru/C (7.5 wt %). The vessel was placed under $N_2$ (20 psig) and vented to atmospheric pressure three times to remove residual oxygen. The vessel was then placed under $H_2$ (50 psig) and the reaction was complete in <5 h based on $H_2$ consumption. After 20 h, the vessel was vented to atmospheric pressure. The reaction slurry was then transferred out of the reaction vessel, filtered and evaporated to a yellow oil which was brought to the following step without further purification. MS (ES$^+$) $C_{14}H_{24}BN_2O_5S$ requires 332. Found: 333 (M+H$^+$).

Step 2: (1R,2S)-1-amino-N-(cyclopropylsulfonyl)amino-2-ethylcyclopropane carboxamide hydrochloride A 0.33 M solution of carbamate from Step 1 in 4N HCl/dioxane was stirred at RT for 12 h. The volatiles were then removed under reduced pressure to give the title compound as a pale yellow solid that was used directly in the next step. $^1$H NMR (300 MHz, DMSO-$d_6$) δ 8.83 (bs, 2H), 3.03 (m, 1H), 1.71-1.37 (m, 5H), 1.16-1.09 (m, 4H), 0.97 (t, J 7.3, 3H).

Intermediate 3: 1-bromohex-5-en-2-one

A solution of 4-pentenoyl chloride in $Et_2O$ was added portionwise to a freshly prepared solution of diazomethane (2.5 eq) in $Et_2O$ at 0° C. The resulting reaction mixture was stirred for 30 min at 0° C. and for a further 12 h at RT in an open flask. After cooling at 0° C., HBr (48% aq., 1.3 eq) was added dropwise and the resulting reaction mixture was stirred at RT for 15 min, after which time the gas evolution had ceased. The ethereal solution was then washed with sat. aq. $NaHCO_3$, brine, dried ($Na_2SO_4$) and concentrated under reduced pressure to give the title compound as a pale yellow oil. $^1$H NMR (300 MHz, CDCl$_3$) δ 5.80 (m, 1H), 5.06 (dd, J 17.5, 1.3, 1H), 5.01 (dd, J 10.5, 1.2, 1H), 3.88 (s, 2H), 2.76 (t, J 7.3, 2H), 2.37 (m, 2H).

Intermediate 4: 1-bromo-3,3-dimethylhex-5-en-2-one

To a solution of 2,2-dimethylpent-4-enoic acid and DMF (0.1 eq) in DCM at 0° C. was added dropwise oxalylchloride (2M in DCM, 1.5 eq) and the resulting mixture was stirred at RT for 1.5 h. The volatiles were then removed under reduced pressure and the crude acyl chloride was progressed according to the same procedure described for Intermediate 3 to give the title compound as a pale yellow oil. $^1$H NMR (300 MHz, CDCl$_3$) δ 5.68 (m, 1H), 5.08 (m, 2H), 4.14 (s, 2H), 2.30 (d, J 7.3, 2H), 1.22 (s, 6H).

Intermediate 5: 1-bromohept-6-en-2-one

The title compound was prepared according to the procedure described for Intermediate 4, using 5-hexenoic acid in place of 2,2-dimethylpent-4-enoic acid. $^1$H NMR (300 MHz, CDCl$_3$) δ 5.77 (m, 1H), 5.05-4.98 (m, 2H), 3.87 (s, 2H), 2.66 (t, J 7.3, 2H), 2.89 (m, 2H), 2.09 (m, 2H).

Intermediate 6: 1-(allyloxy)-3-chloroacetone

Step 1: ethyl (allyloxy)acetate

Ethyl hydroxyacetate was added dropwise to a slurry of NaH (1.1 eq) in DMF at 0° C. and the resulting mixture was stirred at RT for 2 h. After cooling to 0° C., allylbromide (1.1 eq) was added dropwise via syringe and the reaction mixture was stirred at RT for 2 h, quenched by careful addition of sat. aq. $NH_4Cl$ and partitioned between $Et_2O$ and brine. The organic layer was dried ($Na_2SO_4$) and concentrated under reduced pressure to give the title compound as pale yellow oil. $^1$H NMR (300 MHz, CDCl$_3$) δ 5.91 (m, 1H), 5.30 (dd, J 17.2, 1.5, 1H), 5.24 (dd, J 10.6, 0.6, 1H), 4.23 (q, J 2.1, 2H), 4.10 (d, J 5.7, 2H), 4.08 (s, 2H), 1.29 (t, J 7.08, 3H).

Step 2: 1-(allyloxy)-3-chloroacetone

To a solution of $^i$Pr$_2$Net (3.1 eq) in THF at −78° C. was added dropwise BuLi (1.4 M. in hexanes, 3.1 eq). The resulting mixture was stirred at 0° C. for 15 min, cooled again to −78° C. and added via cannula to a solution of ethyl (allyloxy)acetate from Step 1(1 eq) and iodochloromethane (2.5 eq) in $Et_2O$ at −78° C. After stirring 30 min at −78° C., a solution of AcOH (25 eq.) in THF was added dropwise and the resulting mixture was stirred at RT for 15 min and partitioned between $Et_2O$ and brine. The organic layer was washed with sat. aq. $NaHCO_3$, brine, dried ($Na_2SO_4$) and concentrated under reduced pressure. The crude residue was purified by $SiO_2$ gel chromatography (hexane/$Et_2O$=9/1) to give the title compound as a colourless oil. $^1$H NMR (300 MHz, CDCl$_3$) δ 5.90 (m, 1H), 5.35-5.25 (m, 2H), 4.30 (s, 2H), 4.24 (s, 2H), 4.07 (d, J 5.5, 2H).

Intermediate 7: (3R,5S)-5-(methoxycarbonyl)pyrrolidin-3-yl-4-vinyl-1,3-dihydro-2H-isoindole-2-carboxylate hydrochloride Step 1: 1-bromo-2,3-bis(bromomethyl)benzene A suspension of 3-bromo-o-xylene (196 g, 1.06 mol), N-bromosuccinimide (377 g, 2.15 mol) and benzoyl peroxide (0.26 g, 1.0 mmol) in $CCl_4$ (1800 mL) was heated to reflux under nitrogen for 15 h. The contents of the reaction flask were cooled, filtered, and the filtrate evaporated. The crude material was distilled under high vacuum. Major fractions were distilled between 88° C. and 152° C. 108 g pure material was recovered. 182 g slightly crude material was recovered which could be used in the following reaction. $^1$H NMR (CDCl$_3$) δ (ppm) 7.56 (d, J 8.0, 1H), 7.31 (d, J 8.0, 1H), 7.26 (s, 1H), 7.16 (t, J 8.0, 1H), 4.84 (s, 2H), 4.64 (s, 2H).

Step 2: 2-benzyl-4-bromoisoindoline

Potassium bicarbonate (204 g, 2.04 mol) was suspended in MeCN (12 L) and the mixture was heated to 80° C. Solutions of 1-bromo-2,3-bis(bromomethyl)benzene (280 g, 0.82 mol in 500 mL MeCN) and benzylamine (87.5 g, 0.82 mol in 500 mL MeCN) were added concurrently via addition funnels over 1 h. The reaction mixture was stirred at 77° C. for 16 h. The contents of the reaction flask were cooled, filtered and the solvent removed by evaporation. The reaction was partitioned between 1M $K_2CO_3$ and EtOAc. The organics were washed with brine, dried with anhydrous $Na_2SO_4$, filtered, and evaporated. Flash column chromatography (gradient elution: heptane to 10% EtOAc in heptane) gave after evaporation the title compound as a pale oil. $^1H$ NMR ($CDCl_3$) δ (ppm) 7.41-7.39 (m, 2H), 7.37-7.34 (m, 2H), 7.32-7.27 (m, 2H), 7.10-7.03 (m, 2H), 4.02 (s, 2H), 3.97 (s, 2H), 3.91 (s, 2H). LRMS (ESI) m/z 289 [(M+H)$^+$; calcd for $C_{15}H_{15}BrN$: 289].

Converted to HCl salt in HCl/MeOH by adding MTBE and filtering solid to give 118 g of product as the HCl salt.

Step 3: 2-benzyl-4-vinylisoindoline

A solution of 2-benzyl-4-bromoisoindoline (16.7 g, 58.0 mmol) and tributyl(vinyl)tin (20.3 mL, 69.6 mmol) in toluene (400 mL) was degassed by bubbling nitrogen gas through the solution for 0.25 h. Tetrakis(triphenylphosphine)palladium (0) (1.30 g, 1.16 mmol) was added and the resulting solution heated in a 100° C. oil bath under nitrogen for 24 h. The contents of the reaction flask were cooled, evaporated and subjected to flash column chromatography eluting with hexane/EtOAc 95/5 to give after evaporation the title compound as a pale oil that turned pink on standing. LRMS (ESI) m/z 236 [(M+H)$^+$; calcd for $C_{17}H_{18}N$: 236].

Step 4: 4-vinylisoindoline

A solution of 2-benzyl-4-vinylisoindoline (58 mmol) in DCE (150 mL) was placed in a 1 L round bottom flask under nitrogen. To this was attached an addition funnel containing a solution of 1-chloroethyl chloroformate (7.51 mL, 69.6 mmol) in DCE. The reaction flask was cooled in an ice bath and the contents of the addition funnel were added dropwise over 20 min keeping the internal reaction temperature<5° C. After the addition was complete the reaction flask was allowed to warm to RT then heated to reflux for 45 min. The contents of the reaction flask were cooled to RT then the solvent removed by evaporation. Methanol (200 mL) was added and the contents of the reaction flask were heated to reflux for 30 min. The reaction flask was cooled and the solvent removed by evaporation. Water (200 mL) was added and the resulting mixture washed with EtOAc (2×250 mL). The aqueous layer was made basic with 2N sodium hydroxide then extracted with DCM (4×250 mL). The combined organic extracts were dried with anhydrous sodium sulfate, filtered and the filtrate evaporated. The remaining residue was subjected to flash column chromatography eluting with DCM/MeOH/ammonium hydroxide 97/3/0.3 to 95/5/0.5. Evaporation of fractions gave the title compound as a brown oil, 6.00 g (41.4 mmol, 71% yield for two steps). LRMS (ESI) m/z 146 [(M+H)$^+$; calcd for $C_{10}H_{12}N$: 146].

Step 5: 1-tert-butyl 2-methyl (2S,4R)-4-{-[(4-vinyl-1,3-dihydro-2H-isoindol-2-yl)carbonyl]oxy}pyrrolidine-1,2-dicarboxylate A solution of 1-tert-butyl 2-methyl (2S,4R)-4-hydroxypyrrolidine-1,2-dicarboxylate (10.1 g, 41.4 mmol) in DMF (90 mL) under nitrogen was cooled to 0° C. Solid 1,1'-carbonyldiimidazole (6.70 g, 41.4 mmol) was added to the reaction. The contents of the reaction flask were warmed to RT and after 2 h a solution of 4-vinylisoindoline (6.00 g, 41.4 mmol) in DMF (10 mL) was added. The reaction was heated in a 60° C. oil bath for 2 h then cooled and poured into water and 5% potassium bisulfate. The resulting mixture was extracted with EtOAc (4×250 mL). Combined organics were washed with brine, dried with anhydrous sodium sulfate, filtered and evaporated. Flash column chromatography eluting with hexane/EtOAc 70/30 gave the title compound as a white foam, 13.9 g (33.4 mmol, 81% yield). LRMS (ESI) m/z 417 [(M+H)$^+$; calcd for $C_{22}H_{29}N_2O_6$: 417].

Step 6: (3R,5S)-5-(methoxycarbonyl)pyrrolidin-3-yl 4-vinyl-1,3-dihydro-2H-isoindole-2-carboxylate hydrochloride A solution of 1-tert-butyl 2-methyl (2S,4R)-4-{[(4-vinyl-1,3-dihydro-2H-isoindol-2-yl)carbonyl]oxy}pyrrolidine-1,2-dicarboxylate (13.9 g, 33.4 mmol) in EtOAc (700 mL) was cooled in an ice bath then saturated with hydrogen chloride gas. The reaction flask was sealed and allowed to warm to RT. After 3.5 h the solvent was removed by evaporation to give the title compound as a gray solid, 11.2 g, 95% yield). $^1H$ NMR (500 MHz, ppm, $CD_3OD$) δ 7.47-7.45 (m, 1H), 7.32-7.31 (m, 1H), 7.26-7.21 (m, 1H), 6.79-6.73 (m, 1H), 5.79-5.73 (m, 1H), 5.46 (s, 1H), 5.41-5.38 (m, 1H), 4.80-4.72 (m, 4H), 3.91 (s, 3H), 3.74-3.63 (m, 2H), 2.77-2.71 (m, 1H), 2.51-2.46 (m, 1H). LRMS (ESI) m/z 317 [(M+H)$^+$; calcd for $C_{17}H_{21}N_2O_4$: 317].

Example 1

Table 1, Entry 1

(3R,5S,8S)—N-((1R,2S)-1-{[(cyclopropylsulfonyl)amino]carbonyl}-2-vinylcyclopropyl)-8-isopropyl-7-oxo-2-oxa-11-thia-6,9,24,27-tetraazapentacyclo[16.6.2.1$^{3,6}$.1$^{10,13}$.0$^{21,25}$]octacosa-1(24),10(27),12,18,20,22,25-heptaene-5-carboxamide

Step 1: Methyl N-(tert-butoxycarbonyl)-L-valyl-(4R)-4-[(7-vinylisoquinolin-1-yl)oxy]-L-prolinate To a solution of Intermediate 1 in DMF was added Boc-(L)-Val (1.05 eq), followed by $^iPr_2NEt$ (3.5 eq) and TBTU (1.05 eq). The resulting reaction mixture was stirred 12 h at RT and partitioned between EtOAc and 1N aq. HCl. The organic layer was further washed with sat. aq. $NaHCO_3$, brine, dried ($Na_2SO_4$) and concentrated under reduced pressure. The residue was purified by $SiO_2$ gel chromatography (hexane/EtOAc=7/3) to give the title compound as a colourless oil. MS (ES$^+$) $C_{27}H_{35}N_3O_6$ requires: 497. Found: 498 (M+H$^+$).

Step 2: Methyl L-valyl-(4R)-4-[(7-vinylisoquinolin-1-yl)oxy]-L-prolinate hydrochloride A 0.27 M solution of carbamate from Step 1 in 4N HCl/dioxane was stirred at RT for 2 h. The volatiles were then removed under reduced pressure to give the title compound as an off-white solid that was used directly in the next step. MS (ES$^+$) $C_{22}H_{27}N_3O_4$ requires: 397. Found: 398 (M+H$^+$).

Step 3: Methyl N-(aminocarbonothioyl)-L-valyl-(4R)-4-[(7-vinylisoquinolin-1-yl)oxy]-L-prolinate $^iPr_2NEt$ (2 eq) was added to a suspension of hydrochloride from Step 2 in DCM at 0° C., and the resulting clear solution was immediately added to a solution of FMOC-isothiocyanate (1.1 eq) in DCM at 0° C. The resulting mixture was stirred at RT for 30 min and then treated with a 20% solution of piperidine in MeOH. After 3 h, the volatiles were removed under reduced pressure and the residue was purified by $SiO_2$ gel chromatography (gradient elution, hexane/EtOAc=8/2 to DCM/MeOH=95/5) to give the title compound as a pale yellow foam. MS (ES$^+$) $C_{23}H_{28}N_4O_4S$ requires: 456. Found: 457 (M+H$^+$).

Step 4: Methyl N-(4-but-3-en-1-yl-1,3-thiazol-2-yl)-L-valyl-(4R)-4-[(7-vinylisoquinolin-1-yl)oxy]-L-prolinate A solution of thiourea from Step 3 and Intermediate 3 (1.5 eq) in dioxane was stirred at 65° C. for 1 h. The volatiles were then removed under reduced pressure and the residue was purified by $SiO_2$ gel chromatography (DCM/MeOH=98/2) to give the title compound as a pale brown oil. MS (ES$^+$) $C_{29}H_{34}N_4O_4S$ requires: 534. Found: 535 (M+H$^+$).

Step 5: Methyl (3R,5S,8S,16E or Z)-8-isopropyl-7-oxo-2-oxa-11-thia-6,9,24,27-tetraazapentacyclo[16.6.2.1$^{3,6}$.1$^{10,13}$.0$^{21,25}$]octacosa-1(24),10(27),12,18,20,22,25-heptaene-5-carboxylate To a 0.05 M solution of olefin from Step 4 in DCE at 85° C. was added dichloro(5-chloro-2-isopropoxybenzylidene)(1,3-dimethylimidazolidin-2-ylidene)ruthenium (Zhan ruthenium metathesis catalyst RC-301, 0.15 eq) and the resulting reaction mixture was stirred at 85° C. for 2 h. The volatiles were then removed under reduced pressure and the residue was purified by $SiO_2$ gel chromatography (PE/EtOAc=1/1) to give the title compound as a mixture of E- and Z-olefins as a pale brown glass. MS (ES$^+$) $C_{27}H_{30}N_4O_4S$ requires: 506. Found: 507 (M+H$^+$).

Step 6: Methyl (3R,5S,8S)-8-isopropyl-7-oxo-2-oxa-11-thia-6,9,24,27-tetraazapentacyclo[16.6.2.1$^{3,6}$.1$^{10,13}$.0$^{21,25}$]octacosa-1(24),10(27),12,18,20,22,25-heptaene-5-carboxylate To a solution of olefin from Step 5 in MeOH/EtOAc (1/1 v/v) was added 10% Pd/C (10% w/w) and the resulting reaction mixture was stirred at RT under an atmosphere of $H_2$ for 2 h. The catalyst was filtered off, replaced with a fresh aliquot (10 mg) and the reaction mixture was stirred in the above conditions for a further period of time. The process was repeated as previously described until complete conversion to product was observed (typically 36 h, 3 fresh aliquots of catalyst). After filtering off the catalyst, the volatiles were removed under reduced pressure to give the title compound as a pale brown oil. MS (ES$^+$) $C_{27}H_{32}N_4O_4S$ requires: 508. Found: 509 (M+H$^+$).

Step 7: (3R,5S,8S)—N-((1R,2S)-1-{[(cyclopropylsulfonyl)amino]carbonyl}-2-vinylcyclopropyl)-8-isopropyl-7-oxo-2-oxa-11-thia-6,9,24,27-tetraazapentacyclo[16.6.2.1$^{3,6}$.1$^{10,13}$.0$^{21,25}$]octacosa-1(24),10(27),12,18,20,22,25-heptaene-5-carboxamide To a solution of ester from Step 6 in THF/$H_2O$ (1/1 v/v) was added LiOH (10 eq). The resulting reaction mixture was stirred at RT for 2 h and then treated with 1N aq. HCl until pH=2 was reached. The volatiles were removed under reduced pressure, the residue was azeotroped with toluene several times to give the desired acid as intermediate [MS (ES$^+$) $C_{26}H_{30}N_4O_4S$ requires: 494. Found: 495 (M+H$^+$)]. The crude acid was then dissolved in DMF and to this solution was added (1R,2R)-1-amino-N-(cyclopropylsulfonyl)-2-vinylcyclopropanecarboxamide hydrochloride (prepared as described in WO 03/099274, 1.09 eq) followed by $^i$Pr$_2$NEt (3.5 eq) and TBTU (1.09 eq). The resulting reaction mixture was stirred for 12 h at RT and purified directly by reverse phase HPLC to give the title compound as an off white solid.
$^1$H NMR (300 MHz, DMSO-d$_6$) δ 10.69 (s, 1H), 8.85 (s, 1H), 8.01 (d, J 6.0, 1H), 7.95 (bs, 1H), 7.87 (d, J 8.4, 1H), 7.65 (d, J 8.4, 1H), 7.43 (d, J 5.7, 1H), 6.53 (bs, 1H), 6.01 (bs, 1H), 5.62 (m, 1H), 5.25 (d, J 18.3, 1H), 5.13 (d, J 11.7, 1H), 4.87 (m, 1H), 4.46 (m, 1H), 4.30 (m, 1H), 3.99 (dd, J 11.4, 3.0, 1H), 2.99-2.89 (m, 2H), 2.75-2.45 (m, 4H), 2.39-2.12 (m, 3H), 1.77-1.56 (m, 5H), 1.33 (dd, J 9.3, 5.3, 1H), 1.14-1.07 (m, 7H), 0.98 (d, J 6.9, 3H); MS (ES$^+$) $C_{35}H_{43}N_6O_6S_2$ requires: 706. Found: 707 (M+H$^+$).

Example 2

Table 1, Entry 17

(3R,5S,8S,16E)-N-((1R,2S)-1-{[(cyclopropylsulfonyl)amino]carbonyl}-2-vinylcyclopropyl)-8-isopropyl-14,14-dimethyl-7-oxo-2-oxa-11-thia-6,9,24,27-tetraazapentacyclo[16.6.2.1$^{3,6}$.1$^{10,13}$.0$^{21,25}$]octacosa-1(24),10(27),12,16,18,20,22,25-octaene-5-carboxamide Step 1: Methyl N-[4-(1,1-dimethylbut-3-en-1-yl)-1,3-thiazol-2-yl]-L-valyl-(4R)-4-[(7-vinylisoquinolin-1-yl)oxy]-L-prolinate The title compound was prepared according to the procedure described for Example 1, Step 4, using Intermediate 4 in place of Intermediate 3. MS (ES$^+$) $C_{31}H_{38}N_4O_4S$ requires: 562. Found: 563 (M+H).

Step 2: Methyl (3R,5S,8S,16E)-8-isopropyl-14,14-dimethyl-7-oxo-2-oxa-11-thia-6,9,24,27-tetraazapentacyclo[16.6.2.1$^{3,6}$.1$^{10,13}$.0$^{21,25}$]octacosa-1(24),10(27),12,16,18,20,22,25-octaene-5-carboxylate The title compound was prepared using olefin from Step 1, according to the procedure described for Example 1, Step 5. The crude product was purified by $SiO_2$ gel chromatography (gradient elution, PE/EtOAc=1/1 to DCM/MeOH=95/5). MS (ES$^+$) $C_{29}H_{34}N_4O_4S$ requires: 534. Found: 535 (M+H$^+$).

Step 3: (3R,5S,8S,16E)-N-((1R,2S)-1-{[(cyclopropylsulfonyl)amino]carbonyl}-2-vinylcyclopropyl)-8-isopropyl-14,14-dimethyl-7-oxo-2-oxa-11-thia-6,9,24,27-tetraazapentacyclo[16.6.2.1$^{3,6}$.1$^{10,13}$.0$^{21,25}$]octacosa-1(24),10(27),12,16,18,20,22,25-octaene-5-carboxamide The title compound was prepared using ester from Step 2, according to the procedure described for Example 1, Step 7.
$^1$H NMR (400 MHz, DMSO-d$_6$) δ 10.51 (s, 1H), 8.96 (s, 1H), 7.97 (d, J 6.1, 1H), 7.89 (bs, 1H), 7.84 (d, J 8.3, 1H), 7.64 (d, J 8.6, 1H), 7.39 (d, J 5.8, 1H), 6.46 (d, J 16.0, 1H), 6.34 (bs, 1H), 5.81-5.73 (m, 2H), 5.62 (m, 1H), 5.23 (d, J 17.9, 1H), 5.11 (d, J 10.4, 1H), 4.41 (d, J 11.1, 1H), 4.32 (dd, J 10.4, 7.3, 1H), 4.10-4.01 (m, 2H), 2.99 (m, 1H), 2.67-2.58 (m, 2H), 2.21-2.09 (m, 3H), 1.74 (dd, J 7.6, 5.3, 1H), 1.38 (s, 3H), 1.33-1.05 (m, 16H); MS (ES$^+$) $C_{37}H_{44}N_6O_7S_2$ requires: 732. Found: 733 (M+H$^+$).

Example 3

Table 1, Entry 20

(3R,5S,8S)—N-((1R,2S)-1-{[(cyclopropylsulfonyl)amino]carbonyl}-2-vinylcyclopropyl)-8-isopropyl-14,14-dimethyl-7-oxo-2-oxa-11-thia-6,9,24,27-tetraazapentacyclo[16.6.2.1$^{3,6}$.1$^{10,13}$.0$^{21,25}$]octacosa-1(24),10(27),12,18,20,22,25-heptaene-5-carboxamide Step 1: Methyl (3R,5S,8S)-8-isopropyl-14,14-dimethyl-7-oxo-2-oxa-11-thia-6,9,24,27-tetraazapentacyclo[16.6.2.1$^{3,6}$.1$^{10,13}$.0$^{21,25}$]octacosa-1(24),10(27),12,18,20,22,25-heptaene-5-carboxylate The title compound was prepared using ester from Example 2, Step 2 according to the procedure described for Example 1, Step 6. MS (ES$^+$) $C_{25}H_{33}N_3O_5S$ requires: 536. Found: 537 (M+H$^+$).

Step 2: (3R,5S,8S)—N-((1R,2S)-1-{[(cyclopropylsulfonyl)amino]carbonyl}-2-vinylcyclopropyl)-8-isopropyl-14,14-dimethyl-7-oxo-2-oxa-11-thia-6,9,24,27-tetraazapentacyclo[16.6.2.1$^{3,6}$.1$^{10,13}$.0$^{21,25}$]octacosa-1(24),10(27) 12,18,20,22,25-heptaene-5-carboxamide The title compound was prepared using ester from Step 1, according to the procedure described for Example 1, Step 7. $^1$H NMR (400 MHz, DMSO-d$_6$) δ 10.67 (s, 1H), 8.92 (s, 1H), 7.99 (d, J 5.8, 1H), 7.83 (d, J 8.3, 1H), 7.61 (d, J 8.3, 1H), 7.42 (d, J 5.86, 1H), 6.26 (bs, 1H), 5.93 (bs, 1H), 5.63 (m, 1H), 5.26 (d, J 16.9, 1H), 5.13 (d, J 10.1, 1H), 4.43 (m, 1H), 4.20 (d, J 11.9, 1H), 4.01 (d, J 9.8, 1H), 2.97 (m, 1H), 2.75 (m, 2H), 2.62 (m, 1H), 2.27-2.12 (m, 4H), 1.76 (m, 2H), 1.54 (m, 1H), 1.42-1.35 (m, 3H), 1.26 (s, 3H), 1.14-1.02 (m, 12H), 0.97 (d, J 6.6, 3H); MS (ES$^+$) $C_{37}H_{46}N_6O_6S_2$ requires: 734. Found: 735 (M+H$^+$).

Example 4

Table 1, Entry 11

(1R,12E,22S,25S)-22-cyclohexyl-N-((1R,2S)-1-{[(cyclopropylsulfonyl)amino]carbonyl}-2-vinylcyclopropyl)-3,23-dioxo-2-oxa-19-thia-4,21,24,28-tetraazapentacyclo[22.2.1.1$^{4,7}$.1$^{17,20}$.0$^{6,11}$]nonacosa-6,8,10,12,17,20(28)-hexaene-25-carboxamide Step 1: (3R,5S)-1-{(2S)-2-[(tert-butoxycarbonyl)amino]-2-cyclohexylacetyl}-5-(methoxycarbonyl)pyrrolidin-3-yl-4-vinyl-1,3-dihydro-2H-isoindole-2-carboxylate The title compound was prepared according to the procedure described for Step 1, Example 1, using Intermediate 7 in place of Intermediate 1 and Boc-Chg in place of Boc-Val. MS (ES$^+$) $C_{30}H_{41}N_3O_7$ requires: 555. Found: 556 (M+H$^+$).

Step 2: (3R,5S)-1-{(2S)-2-amino-2-cyclohexylacetyl}-5-(methoxycarbonyl)pyrrolidin-3-yl-4-vinyl-1,3-dihydro-2H-isoindole-2-carboxylate hydrochloride The title compound was prepared using carbamate from Step 1, according to the procedure described for Example 1, Step 2. MS (ES$^+$) $C_{25}H_{33}N_3O_5S$ requires: 455. Found: 456 (M+H$^+$).

Step 3: (3R,5S)-1-{(2S)-2-[(aminocarbonothioyl)amino]-2-cyclohexylacetyl}-5-(methoxycarbonyl)pyrrolidin-3-yl-4-vinyl-1,3-dihydro-2H-isoindole-2-carboxylate The title compound was prepared using hydrochloride from Step 2, according to the procedure described for Example 1, Step 3. MS (ES$^+$) $C_{26}H_{34}N_4O_5S$ requires: 514. Found: 515 (M+H$^+$).

Step 4: (3R,5S)-1-{(2S)-2-cyclohexyl-2-[(4-pent-4-en-1-yl-1,3-thiazol-2-yl)amino]acetyl}-5-(methoxycarbonyl)pyrrolidin-3-yl-4-vinyl-1,3-dihydro-2H-isoindole-2-carboxylate The title compound was prepared using thiourea from Step 3 and Intermediate 5 in place of Intermediate 3, according to the procedure described for Example 1, Step 4. MS (ES$^+$) $C_{33}H_{42}N_4O_5S$ requires: 606. Found: 607 (M+H$^+$).

Step 5: methyl (1R,12E,22S,25S)-22-cyclohexyl-3,23-dioxo-2-oxa-19-thia-4,21,24,28-tetraazapentacyclo[22.2.1.1$^{4,7}$.1$^{17,20}$.0$^{6,11}$]nonacosa-6,8,10,12,17,20(28)-hexaene-25-carboxylate The title compound was prepared using olefin from Step 4, according to the procedure described for Example 1, Step 5. MS (ES$^+$) $C_{31}H_{38}N_4O_5S$ requires: 578. Found: 579 (M+H$^+$).

Step 6: (1R,12E,22S,25S)-22-cyclohexyl-N-((1R,2S)-1-{[(cyclopropylsulfonyl)amino]carbonyl}-2-vinylcyclopropyl)-3,23-dioxo-2-oxa-19-thia-4,21,24,28-tetraazapentacyclo[22.2.1.1$^{4,7}$.1$^{17,20}$.0$^{6,11}$]nonacosa-6,8,10,12,17,20(28)-hexaene-25-carboxamide The title compound was prepared using ester from Step 5, according to the procedure described for Example 1, Step 7. $^1$H NMR (400 MHz, DMSO-d$_6$) δ 10.64 (s, 1H), 8.80 (s, 1H), 7.32-7.20 (m, 3H), 6.40 (bs, 1H), 6.36 (d, J 16.2, 1H), 6.05 (m, 1H), 5.6 (m, 1H), 5.3 (bs, 1H), 5.23 (d, J 16.9, 1H), 5.11 (d, J 11.1, 1H), 4.79 (d, J 14.6, 1H), 4.65 (m, 4H), 4.29 (t, J 8.6, 1H), 4.16 (m, 1H), 3.97 (m, 1H), 2.9 (m, 1H), 2.66-2.36 (m, 4H), 2.35-2.09 (m, 9H), 1.90-1.59 (m, 7H) 1.34-0.99 (m, 7H); MS (ES$^+$) $C_{39}H_{48}N_6O_7S_2$ requires: 776. Found: 777.0 (M+H$^+$).

Example 5

Table 1, Entry 12

(1R,22S,25S)-22-cyclohexyl-N-((1R,2S)-1-{[(cyclopropylsulfonyl)amino]carbonyl}-2-vinylcyclopropyl)-3,23-dioxo-2-oxa-19-thia-4,21,24,28-tetraazapentacyclo[22.2.1.1$^{4,7}$.1$^{17,20}$.0$^{6,11}$]nonacosa-6,8,10,17,20(28)-pentaene-25-carboxamide Step 1: methyl (1R,22S,25S)-22-cyclohexyl-3,23-dioxo-2-oxa-19-thia-4,21,24,28-tetraazapentacyclo[22.2.1.1$^{4,7}$.1$^{17,20}$.0$^{6,11}$]nonacosa-6,8,10,17,20(28)-pentaene-25-carboxylate The title compound was prepared using ester from Example 4, Step 5 according to the procedure described for Example 1, Step 6. MS (ES$^+$) $C_{31}H_{40}N_4O_5S$ requires: 497. Found: 581 (M+H$^+$).

Step 2: (1R,22S,25S)-22-cyclohexyl-N-((1R,2S)-1-{[(cyclopropylsulfonyl)amino]carbonyl}-2-vinylcyclopropyl)-3,23-dioxo-2-oxa-19-thia-4,21,24,28-tetraazapentacyclo[22.2.1.1$^{4,7}$.1$^{17,20}$.0$^{6,11}$]nonacosa-6,8,10,17,20(28)-pentaene-25-carboxamide The title compound was prepared using ester from Step 1, according to the procedure described for Example 1, Step 7. MS (ES$^+$) C$_{39}$H$_{50}$N$_6$O$_7$S$_2$ requires: 778. Found: 779 (M+H$^+$). $^1$H NMR (400 MHz, CDCl$_3$) δ 10.55 (bs, 1H), 7.23 (d, J 7.6, 1H), 7.11 (d, J 7.3, 1H), 7.05 (d, J 7.3, 1H), 5.88 (bs, 1H), 5.77 (bs, 1H), 5.57 (s, 1H), 5.26 (d, J 16.9, 1H), 5.13 (d, J 10.9, 1H), 4.74 (m, 2H), 4.46 (m, 3H), 4.22 (bs, 1H), 3.88, (d, J 10.1, 1H), 2.91 (m, 1H), 2.58-2.03 (m, 10H), 1.83-1.58 (m, 9H), 1.44-1.03 (m, 14H); MS (ES$^+$) C$_{39}$H$_{50}$N$_6$O$_7$S$_2$ requires: 778. Found: 779 (M+H$^+$).

Example 6

Table 1, Entry 16

(1R,12E,22S,25S)-22-cyclohexyl-N-((1R,2S)-1-{[(cyclopropylsulfonyl)amino]carbonyl}-2-ethylcyclopropyl)-3,23-dioxo-2-oxa-19-thia-4,21,24,28-tetraazapentacyclo[22.2.1.1$^{4,7}$.1$^{17,20}$.0$^{6,11}$]nonacosa-6,8,10,12,17,20(28)-hexaene-25-carboxamide The title compound was prepared according to the procedure described for Example 4, Step 6, using Intermediate 2 in place of (1R,2R)-1-amino-N-(cyclopropylsulfonyl)-2-vinylcyclopropanecarboxamide hydrochloride. $^1$H NMR (400 MHz, DMSO-d$_6$) δ 10.60 (s, 1H), 8.76 (s, 1H), 7.34-7.25 (m, 3H), 6.43-6.39 (m, 2H), 6.07 (m, 1H), 5.33 (bs, 1H), 4.84-4.62 (m, 5H), 4.32 (bt, J 8.3, 1H), 4.18 (d, J 11.4, 1H), 4.02 (dd, J 11.0, 3.7, 1H), 2.99 (m, 1H), 2.67-2.15 (m, 7H), 1.87-1.67 (m, 8H), 1.55 (m, 1H), 1.44-1.07 (m, 13H), 0.93 (t, J 7.1, 3H); MS (ES$^+$) C$_{39}$H$_{50}$N$_6$O$_7$ requires: 778. Found: 779 (M+H$^+$).

Example 7

Table 1, Entry 14

(1R,12E,22S,25S)—N-((1R,2S)-1-{[(cyclopropylsulfonyl)amino]carbonyl}-2-ethenylcyclopropyl)-22-[(1S)-1-methylpropyl]-3,23-dioxo-2-oxa-19-thia-4,21,24,28-tetraazapentacyclo[22.2.1.1$^{4,7}$.1$^{17,20}$.0$^{6,11}$]nonaacosa-6,8,10,12,17,20(28)-hexaene-25-carboxamide Step 1: methyl N-(tert-butoxycarbonyl)-L-isoleucyl-(4R)-4-{[(4-vinyl-1,3-dihydro-2H-isoindol-2-yl)carbonyl]oxy}-L-prolinate The title compound was prepared according to the procedure described for Step 1, Example 4, using Boc-Ile in place of Boc-Chg. MS (ES$^+$) C$_{28}$H$_{39}$N$_3$O$_7$ requires: 529. Found: 530 (M+H$^+$).

Step 2: methyl L-isoleucyl-(4R)-4-{[(4-vinyl-1,3-dihydro-2H-isoindol-2-yl)carbonyl]oxy}-L-prolinate hydrochloride The title compound was prepared using carbamate from Step 1, according to the procedure described for Example 1, Step 2. MS (ES$^+$) C$_{23}$H$_{31}$N$_3$O$_5$ requires: 429. Found: 430 (M+H$^+$).

Step 3: N-(aminocarbonothioyl)-L-isoleucyl-(4R)-4-{[(4-vinyl-1,3-dihydro-2H-isoindol-2-yl)carbonyl]oxy}-L-prolinate The title compound was prepared using hydrochloride from Step 2, according to the procedure described for Example 1, Step 3. MS (ES$^+$) C$_{24}$H$_{32}$N$_4$O$_5$S requires: 488. Found: 489 (M+H$^+$).

Step 4: methyl N-(4-pent-4-en-1,3-thiazol-2-yl)-L-isoleucyl-(4R)-4-{[(4-vinyl-1,3-dihydro-2H-isoindol-2-yl)carbonyl]oxy}-L-prolinate The title compound was prepared using thiourea from Step 3 and Intermediate 5 in place of Intermediate 3, according to the procedure described for Example 1, Step 4. MS (ES$^+$) C$_{31}$H$_{40}$N$_4$O$_5$S requires: 580. Found: 581 (M+H$^+$).

Step 5: methyl (1R,12E,22S,25S)-22-sec-butyl-3,23-dioxo-2-oxa-19-thia-4,21,24,28-tetraazapentacyclo[22.2.1.1$^{4,7}$.1$^{17,20}$.0$^{6,11}$]nonacosa-6,8,10,12,17,20(28)-hexaene-25-carboxylate The title compound was prepared using olefin from Step 4, according to the procedure described for Example 1, Step 5. MS (ES$^+$) C$_{29}$H$_{36}$N$_4$O$_5$S requires: 552. Found: 553 (M+H$^+$).

Step 6: (1R,12E,22S,25S)—N-((1R,2S)-1-{[(cyclopropylsulfonyl)amino]carbonyl}-2-ethenylcyclopropyl)-22-[(1S)-1-methylpropyl]-3,23-dioxo-2-oxa-19-thia-4,21,24,28-tetraazapentacyclo[22.2.1.1$^{4,7}$.1$^{17,20}$.0$^{6,11}$]nonaacosa-6,8,10,12,17,20(28)-hexaene-25-carboxamide The title compound was prepared using ester from Step 5, according to the procedure described for Example 1, Step 7. $^1$H NMR (400 MHz, DMSO-d$_6$) δ 10.63 (s, 1H), 8.86 (s, 1H), 7.34-7.25 (m, 3H), 6.43-6.39 (m, 2H), 6.07 (m, 1H), 5.64 (m, 1H), 5.32 (bs, 1H), 5.27 (d, J 16.9, 1H), 5.14 (d, J 11.4, 1H), 4.83 (bd, J 14.6, 1H), 4.75-4.62 (m, 4H), 4.33 (t, J 8.3, 1H), 4.20 (d, J 11.1, 1H), 4.02 (bd, J 8.1, 1H), 2.97 (m, 1H), 2.66-2.15 (m, 9H), 1.96-1.74 (m, 4H), 1.53 (m, 1H), 1.35 (dd, J 9.2, 4.9, 1H), 1.22 (m, 1H), 1.13-1.03 (m, 7H), 0.90 (t, J 7.33, 3H); MS (ES$^+$) C$_{37}$H$_{46}$N$_6$O$_7$S$_2$ requires: 750. Found: 751 (M+H$^+$).

Example 8

Table 2, Entry 1

(3R,5S,8S)—N-((1R,2S)-1-{[(cyclopropylsulfonyl)amino]carbonyl}-2-vinylcyclopropyl)-8-isopropyl-7-oxo-2,27-dioxa-6,9,11,12,24-pentzapentacyclo[16.6.2.1$^{3,6}$.1$^{10,13}$.0$^{21,25}$]octacosa-1(24),10,12,18,20,22,25-heptaene-5-carboxamide Step 1: tert-butyl 2-pent-4-enoylhydrazinecarboxylate To a solution of pent-4-enoic acid 0.1 M in DCM, tert-butyl carbazate (2 eq) was added followed by 1-(3-dimethylaminopropyl)-3-ethylcarbodiimide hydrochloride (1.02 eq) and the mixture was allowed to stir at RT overnight. DCM was added and the organic solution was washed sequentially with saturated aq. NaHCO$_3$ followed by saturated aq. NaCl and then dried over Na$_2$SO$_4$. Removal of the solvent in vacuo yielded the title compound as colorless oil. This material was used in the next step without further purification. $^1$H NMR (300 MHz, DMSO-d$_6$) δ: 7.33 (bs, 1H), 6.51 (bs, 1H), 5.88-5.75 (m, 1H), 5.10-4.99 (m, 2H), 2.43-2.38 (m, 2H), 2.32 (t, J 6.8, 2H), 2.03 (s, 9H).

Step 2: pent-4-enohydrazide tert-Butyl 2-pent-4-enoylhydrazinecarboxylate (from Step 1) was cooled to 0° C. and trifluoroacetic acid was added through a dropping funnel. The mixture was allowed to warm to RT over 1 h. NaHCO$_3$ was added to the mixture until it reached pH 7. The product was extracted with DCM, the organic layer was dried over Na$_2$SO$_4$, and the solvent removed in vacuo yielding title compound as a pale yellow oil. $^1$H NMR (400 MHz, DMSO-d$_6$) δ: 8.95 (bs, 1H), 5.84-5.74 (m, 1H), 5.04 (dd, J 17, 1.6, 1H), 4.97 (d, J 10, 1H), 4.26 (bs, 2H), 2.45-2.23 (m, 2H), 2.12-2.08 (m, 2H).

Step 3: methyl N-[(2-pent-4-enoylhydrazino)carbonyl]-L-valinate

To a 1.6 M solution of pent-4-enohydrazide (from Step 2) in dioxane, 1 eq. of methyl N-(oxomethylene)-L-valinate, (prepared as described in J. Het. Chem. 1990, 739) was added. After sting at RT for 3 h, volatiles were removed in vacuo, to obtain the title compound. $^1$H NMR (400 MHz, DMSO-d$_6$) δ: 9.55 (d, J 2.1, 1H), 7.86 (d, J 2.2, 1H), 6.48 (d, J 8.1, 1H), 5.86-5.76 (m, 1H), 5.04 (dd, J 17.2, 1.5, 1H), 4.96 (d, J 18.2, 10.3, 1H), 4.09 (dd, J 8.7, 5.7, 1H), 3.64 (s, 3H), 2.32-2.24 (m, 2H), 2.22-2.15 (m, 2H), 2.08-1.90 (m, 1H), 0.94 (d, J 3.9, 3H), 0.92 (d, J 3.9, 3H). MS (ES$^+$) C$_{12}$H$_{21}$N$_3$O$_4$ requires: 271 found: 272 (M+H$^+$).

Step 4: methyl N-(5-but-3-en-1-yl-1,3,4-oxadiazol-2-yl)-L-valinate

Methyl N-[(2-pent-4-enoylhydrazino)carbonyl]-L-valinate (from Step 3) was heated at 80° C. for 2 h in POCl$_3$ (0.1 M solution). The mixture was cooled at 0° C. and water was carefully added. Solid NaHCO$_3$ was added until the mixture reached pH 7, then the mixture was extracted with EtOAc and the organic layer dried over Na$_2$SO$_4$ to obtain a pale yellow oil. $^1$H NMR (400 MHz, DMSO-d$_6$) δ: 8.42 (d, J 15.7, 1H), 5.88-5.78 (m, 1H), 5.08 (d, J 17.2, 1H), 5.01 (d, J 10.3, 1H), 4.04 (dd, J 7.1, 14.2, 1H), 3.64 (s, 3H), 2.75 (t, J 7.3, 2H), 2.39 (m, 2H), 2.13-2.06 (m, 1H), 0.94 (d, J 3.9, 3H), 0.92 (d, J 3.9, 3H). MS (ES$^+$) C$_{12}$H$_{19}$N$_3$O$_3$ requires: 253 found: 254 (M+H$^+$).

Step 5: N-(5-but-3-en-1-yl-1,3,4-oxadiazol-2-yl)-L-valine

To a 0.18 M solution of methyl N-(5-but-3-en-1-yl-1,3,4-oxadiazol-2-yl)-L-valinate (from Step 4) in H$_2$O/THF (1/1 v/v), LiOH (2 eq.) was added at RT. The resulting reaction mixture was stirred for 1 h at RT and then treated with HCl 1N until pH=2 was reached. The aqueous phase was extracted with EtOAc and the organic layer dried over Na$_2$SO$_4$ to obtain a pale yellow solid. MS (ES$^+$) C$_{11}$H$_{17}$N$_3$O$_3$ requires: 239 found: 240 (M+H$^+$).

Step 6: methyl N-(5-but-3-en-1-yl-1,3,4-oxadiazol-2-yl)-L-valyl-4-[(7-vinylisoquinolin-1-yl)oxy]-L-prolinate To a solution of intermediate 1 in DMF was added N-(5-but-3-en-1-yl-1,3,4-oxadiazol-2-yl)-L-valine (from Step 5, 1.05 eq), followed by $^i$Pr$_2$NEt (3.5 eq) and TBTU (1.05 eq). The resulting reaction mixture was stirred for 12 h at RT and partitioned between EtOAc and brine. The organic layer was dried (Na$_2$SO$_4$) and concentrated under reduced pressure. The residue was purified by SiO$_2$ gel chromatography (Hex/EtOAc=1/1) to give the title compound as a colourless oil. MS (ES$^+$) C$_{28}$H$_{33}$N$_5$O$_5$ requires: 519. Found: 520 (M+H$^+$).

Step 7: methyl (3R,5S,8S,16E or Z)-8-isopropyl-7-oxo-2,27-dioxa-6,9,11,12,24-pentaazapentacyclo[16.6.2.1$^{3,6}$.1$^{10,13}$.0$^{21,25}$]octacosa-1(24),10,12,16,18,20,22,25-octaene-5-carboxylate To a 0.01 M solution of olefin methyl N-(5-but-3-en-1-yl-1,3,4-oxadiazol-2-yl)-L-valyl-4-[(7-vinylisoquinolin-1-yl)oxy]-L-prolinate (from Step 6) in DCE at 85° C. was added dichloro(5-chloro-2-isopropoxybenzylidene)(1,3-dimethylimidazolidin-2-ylidene)ruthenium (Zhan ruthenium metathesis catalyst RC-301, 0.15 eq) and the resulting reaction mixture was stirred at 85° C. for 2 h. The volatiles were then removed under reduced pressure and the residue was purified by SiO$_2$ gel chromatography (PE/EtOAc=3/7) to give the title compound as a mixture of E- and Z-isomers as a pale yellow oil. MS (ES$^+$) C$_{26}$H$_{29}$N$_5$O$_5$ requires: 491. Found: 492 (M+H$^+$).

Step 8: methyl (3R,5S,8S)-8-isopropyl-7-oxo-2,27-dioxa-11-thia-6,9,11,12,24-pentaazapentacyclo[16.6.2.1$^{3,6}$.1$^{10,13}$.0$^{21,25}$]octacosa-1(24),10,12,18,20,22,25-heptaene-5-carboxylate To a solution of methyl (3R,5S,8S,16E or Z)-8-isopropyl-7-oxo-2,27-dioxa-6,9,11,12,24-pentaazapentacyclo[16.6.2.1$^{3,6}$.1$^{10,13}$.0$^{21,25}$]octacosa-1(24),10,12,16,18,20,22,25-octaene-5-carboxylate (from Step 7) in ETOH was added 10% Pd/C (10% w/w) and the resulting reaction mixture was stirred at RT under an atmosphere of H$_2$ for 2 h. The catalyst was filtered off and volatiles were removed under reduced pressure to give the title compound as a colorless oil. MS (ES$^+$) C$_{26}$H$_{31}$N$_5$O$_5$ requires: 493. Found: 494 (M+H$^+$).

Step 9: (3R,5S,8S)-8-isopropyl-7-oxo-2,27-dioxa-6,9,11,12,24-pentaazapentacyclo[16.6.2.1$^{3,6}$.1$^{10,13}$.0$^{21,25}$]octacosa-1(24),10,12,18,20,22,25-heptaene-5-carboxylic acid To a solution of methyl (3R,5S,8S)-8-isopropyl-7-oxo-2,27-dioxa-11-thia-6,9,11,12,24-pentaazapentacyclo[16.6.2.1$^{3,6}$.1$^{10,13}$.0$^{21,25}$]octacosa-1(24), 10,12,18,20,22,25-heptaene-5-carboxylate (from Step 8) in THF/H$_2$O (1/1 v/v) was added LiOH (4 eq). The resulting reaction mixture was stirred at RT for 2 h and then treated with 1N aq. HCl until pH=2 was reached. Aqueous phase extracted with EtOAc and the organic layer dried over Na$_2$SO$_4$ to obtain a white solid. MS (ES$^+$) C$_{25}$H$_{29}$N$_5$O$_5$ requires: 479. Found: 480 (M+H$^+$).

Step 10: (3R,5S,8S)—N-((1R,2S)-1-{[(cyclopropylsulfonyl)amino]carbonyl}-2-vinylcyclopropyl)-8-isopropyl-7-oxo-2,27-dioxa-6,9,11,12,24-pentzapentacyclo[16.6.2.1$^{3,6}$.1$^{10,13}$.0$^{21,25}$]octacosa-1(24),10,12,18,20,22,25-heptaene-5-carboxamide (3R,5S,8S)-8-isopropyl-7-oxo-2,27-dioxa-6,9,11,12,24-pentaazapentacyclo[16.6.2.1$^{3,6}$.1$^{10,13}$.0$^{21,25}$]octacosa-1(24), 10,12,18,20,22,25-heptaene-5-carboxylic acid (from Step 9) was dissolved in DMF and to this solution was added (1R, 2R)-1-amino-N-(cyclopropylsulfonyl)-2-vinylcyclopropanecarboxamide hydrochloride (prepared as described in WO 03/09927, 1.09 eq) followed by $^iPr_2NEt$ (3.5 eq) and TBTU (1.09 eq). The resulting reaction mixture was stirred for 12 h at RT and purified directly by reverse phase HPLC to give the title compound as an off white solid. $^1H$ NMR (400 MHz, DMSO-$d_6$) δ 10.34 (s, 1H), 8.93 (s, 1H), 7.97-7.92 (m, 2H), 7.78 (d, J 8.3, 1H), 7.68 (s, 1H), 7.60 (d, J 8.3, 1H), 7.36 (d, J 5.7, 1H), 5.76 (bs, 1H), 5.62-5.56 (m, 1H), 5.21 (d, J 17.1, 1H), 5.08 (d, J 10.7, 1H), 4.90 (d, J 11.3, 1H), 4.25-4.16 (m, 2H), 3.97 (d, J 8.6, 1H), 2.96-2.89 (m, 4H), 2.86-2.58 (m, 2H), 2.19-2.07 (m, 3H), 1.75-1.62 (m, 5H), 1.42-1.40 (m, 1H), 1.29 (m, 1H), 1.10-1.05 (m, 3H), 1.01 (d, J 6.6, 3H), 0.96 (d, J 6.6, 3H). MS (ES$^+$) $C_{34}H_{41}N_7O_7S$ requires: 691. Found: 692 (M+H$^+$).

Example 9

Table 1, Entry 3

(3R,5S,8S)—N-((1R,2S)-1-{[(cyclopropylsulfonyl) amino]carbonyl}-2-ethenylcyclopropyl)-8-(1-methylethyl)-7-oxo-23-phenyl-2-oxa-11-thia-6,9,22,27-tetraazapentacyclo[16.6.2.1$^{3,6}$.1$^{10,13}$.0$^{21,25}$]octacosa-1(24),10(27),12,18,20,22,25-heptaene-5-carboxamide The title compound was prepared as described for Example 1, using in Step 1 methyl (2S,4R)-4-[(2-phenyl-6-vinylquinolin-4-yl)oxy]pyrrolidine-2-carboxylate hydrochloride (prepared as described in WO2006/119061) instead of Intermediate 1. MS (ES$^+$) $C_{40}H_{47}N_6O_6S_2$ requires: 782. Found: 783 (M+H$^+$).

Example 10

Table 2, Entry 3

(1R,22S,25S)-22-cyclohexyl-N-((1R,2S)-1-{[cyclopropylsulfonyl)amino]carbonyl}-2-ethenylcyclopropyl)-3,23-dioxo-2,28-dioxa-4,18,19,21,24-pentaazapentacyclo[22.2.1.1$^{4,7}$.1$^{17,20}$.0$^{6,11}$]nonacosa-6,8,10,17,19-pentaene-25-carboxamide The title compound was prepared as described for Example 8, using in Step 1 hex-5-enoic acid instead of pent-4-enoic acid and in Step 6 Intermediate 7 instead of Intermediate 1. MS (ES$^+$) $C_{38}H_{49}N_7O_8S$ requires: 763. Found: 764 (M+H$^+$).

Example 11

Table 2, Entry 4

(1R,12E,22S,25S)-22-cyclohexyl-N-((1R,2S)-1-{[cyclopropylsulfonyl)amino]carbonyl}-2-ethenylcyclopropyl)-3,23-dioxo-2,28-dioxa-4,18,19,21,24-pentazapentacyclo[22.2.1.1$^{4,7}$.1$^{17,20}$.0$^{6,11}$]nonacosa-6,8,10,12,17,19-hexaene-25-carboxamide The title compound was prepared as described for Example 8, using in Step 1 hex-5-enoic acid instead of pent-4-enoic acid and in Step 6 Intermediate 7 instead of Intermediate 1; the hydrogenation Step 8 described in Example 8 was not performed. MS (ES$^+$) $C_{38}H_{47}N_7O_8S$ requires: 761. Found: 762 (M+H$^+$).

Example 12

Table 2, Entry 5

(3R,5S,8S)—N-((1R,2S)-1-{[(cyclopropylsulfonyl) amino]carbonyl}-2-ethenylcyclopropyl)-23-iodo-8-isopropyl-7-oxo-2,28-dioxa-6,9,11,12,25-pentzapentacyclo[22.2.1.1$^{4,7}$.1$^{17,20}$.0$^{6,11}$]nonacosa-1(25),10, 12,19,21,23,26-heptaene-5-carboxamide Step 1: methyl (3R,5S,8S)-8-isopropyl-7-oxo-2,28-dioxa-6,9,11,12,25-pentaazapentacyclo[17.6.2. 1$^{3,6}$.1$^{10,13}$.0$^{22,26}$]noncosa-1(25) 10,12,19,21,23,26-heptaene-5-carboxylate The title compound was prepared as described for Example 8, Steps 1-8, using in Step 1 hex-5-enoic acid instead of pent-4-enoic acid. MS (ES$^+$) $C_{27}H_{33}N_5O_5$ requires: 507. Found: 508 (M+H).

Step 2: methyl (3R,5S,8S)-23-iodo-8-isopropyl-7-oxo-2,28-dioxa-6,9,11,12,25-pentaazapentacyclo [17.6.2.1$^{3,6}$.1$^{10,13}$.0$^{22,26}$]noncosa-1(25),10,12,19,21, 23,26-heptaene-5-carboxylate To a 0.3 M solution of methyl (3R,5S,8S)-8-isopropyl-7-oxo-2,28-dioxa-6,9,11,12,25-pentaazapentacyclo[17.6.2. 1$^{3,6}$.1$^{10,13}$.0$^{22,26}$]noncosa-1(25),10,12,19,21,23,26-heptaene-5-carboxylate (from Step 1) in dry DCM was added triflic acid (2 eq) and N-iodosuccinimide (2 eq) and the mixture was stirred under $N_2$ for 16 h. An additional portion of N-iodosuccinimide (2 eq) was added and the reaction was stirred for additional 24 h. The reaction mixture was poured into saturated NaHCO$_3$ and extracted with DCM (2×). The combined organic layers were washed with brine, dried over Na$_2$SO$_4$, filtered and concentrated. The resulting crude compound was purified on silica gel (20% to 40% EtOAc in PE) to yield the compound as a yellow solid. MS (ES$^+$) $C_{27}H_{32}IN_5O_5$ requires: 633. Found: 634 (M+H$^+$).

Step 3: (3R,5S,8S)-23-iodo-8-isopropyl-7-oxo-2,28-dioxa-6,9,11,12,25-pentaazapentacyclo[17.6.2. 1$^{3,6}$.1$^{10,13}$.0$^{22,26}$]nonacosa-1(25),10,12,19,21,23,26-heptaene-5-carboxylic acid To a solution of methyl (3R,5S,8S)-23-iodo-8-isopropyl-7-oxo-2,28-dioxa-6,9,11,12,25-pentaazapentacyclo [17.6.2.1$^{3,6}$.1$^{10,13}$.0$^{22,26}$]nonacosa-1(25),10,12,19,21,23,26-heptaene-5-carboxylate (from Step 2) in THF/H$_2$O (1/1 v/v) was added LiOH (4 eq). The resulting reaction mixture was stirred at RT for 2 h and then treated with 1N aq. HCl until pH=2 was reached. Aqueous phase extracted with EtOAc and organic layer dried over Na$_2$SO$_4$ to get a white solid. MS (ES$^+$) $C_{26}H_{30}IN_5O_5$ requires: 619. Found: 620 (M+H$^+$).

Step 4: (3R,5S,8S)—N-((1R,2S)-1-{[(cyclopropyl-sulfonyl)amino]carbonyl}-2-ethenylcyclopropyl)-23-iodo-8-isopropyl-7-oxo-2,28-dioxa-6,9,11,12,25-pentzapentacyclo[17.6.2.1$^{3,6}$.1$^{10,13}$.0$^{22,26}$]nonacosa-1(25),10,12,19,21,23,26-heptaene-5-carboxamide (3R,5S,8S)-23-Iodo-8-isopropyl-7-oxo-2,28-dioxa-6,9, 11,12,25-pentaazapentacyclo[17.6.2.1$^{3,6}$.1$^{10,13}$.0$^{22,26}$]noncosa-1(25),10,12,19,21,23,26-heptaene-5-carboxylic acid (from Step 3) was dissolved in DMF and to this solution was added Intermediate 2 (1.09 eq) followed by $^i$Pr$_2$NEt (3.5 eq) and TBTU (1.09 eq). The resulting reaction mixture was stirred 12 h at RT and purified by reverse phase HPLC to give the title compound as an off-white solid. $^1$H NMR (600 MHz, DMSO-d$_6$) δ 10.364 (s, 1H), 8.96 (s, 1H), 8.36 (s, 1H), 8.00 (d, J 9.1, 1H), 7.80 (d, J 8.4, 1H), 7.74 (d, J 10.8, 1H), 7.73 (s, 1H), 5.80 (s, 1H), 5.61 (m, 1H), 5.21 (d, J 17.7, 1H), 5.08 (d, J 11.8, 1H), 4.95 (d, J 11.6, 1H), 4.24 (dd, J 11.0, 6.7, 1H), 4.05 (t, J 9.6, 1H), 4.0 (dd, J 11.6, 3.5, 1H), 2.96-2.89 (m, 2H), 2.72 (m, 1H), 2.62 (m, 1H), 2.55-2.49 (m, 2H), 2.19-2.08 (m, 3H), 1.80 (m, 1H), 1.73-1.64 (m, 3H), 1.59 (m, 1H), 1.44-1.39 (m, 2H), 1.28 (dd, J 9.4, 5.1, 1H), 1.10-1.03 (m, 4H), 1.00 (d, J 6.7, 3H), 0.96 (d, J 6.7, 3H). MS (ES$^+$) C$_{35}$H$_{42}$IN$_7$O$_7$S requires: 831. Found: 832 (M+H$^+$).

Example 13

Table 3, Entry 10

(3R,5S,8S,16E)-8-cyclohexyl-N-((1R,2S)-1-{[(cyclopropylsulfonyl)amino]carbonyl}-2-vinylcyclopropyl)-19-methoxy-14,14-dimethyl-7-oxo-23-phenyl-2-oxa-11-thia-6,9,22,27-tetraazapentacyclo [16.6.2.13,5.110,13.021,25]octacosa-1(24),10(27), 12,16,18,20,22,25-octaene-5-carboxamide The title compound was prepared as described for Example 2, employing in Step 1 methyl (2S,4R)-4-[(7-methoxy-2-phenyl-6-vinylquinolin-4-yl)oxy]-pyrrolidine-2-carboxylate hydrochloride (prepared as described in WO2006/119061) instead of Intermediate 1, and Boc-(L)-cyclohexylglycine instead of Boc-(L)-Val. $^1$H NMR (400 MHz, DMSO-d$_6$) δ 10.56 (s, 1H), 8.94 (s, 1H), 8.18 (d, J 5.8, 2H), 7.86 (s, 1H), 7.82-7.73 (m, 4H), 7.67 (s, 1H), 6.72 (d, J 16.4, 1H), 6.48 (s, 1H), 5.97 (bs, 1H), 5.84 (m, 1H), 5.61 (m, 1H), 5.23 (d, J 16.9, 1H), 5.13 (d, J 10.1, 1H), 4.54 (d, J 12.6, 1H), 4.31 (m, 1H), 4.20 (d, J 10.6, 1H), 4.06 (s, 3H), 2.98 (m, 1H), 2.74 (m, 2H), 2.62 (m, 2H), 2.39-2.26 (m, 2H), 2.14-1.58 (m, 7H), 1.40 (s, 3H), 1.35-1.00 (m, 14H); MS (ES$^+$) C$_{47}$H$_{54}$N$_6$O$_7$S$_2$ requires: 879. Found: 880 (M+H$^+$).

Example 14

Table 3, Entry 11

(3R,5S,8S,16E)-8-cyclohexyl-N-((1R,2S)-1-{[(cyclopropylsulfonyl)amino]carbonyl}-2-vinylcyclopropyl)-19-methoxy-14,14-dimethyl-7-oxo-2-oxa-11-thia-6,9,24,27-tetraazapentacyclo[16.6.2.13,5.110, 13.021,25]octacosa-1(24),10(27),12,16,18,20,22,25-octaene-5-carboxamide The title compound was prepared as described for Example 13, employing in Step 1 methyl (2S,4R)-4-[(6-methoxy-7-vinylisoquinolin-1-yl)oxy]-pyrrolidine-2-carboxylate hydrochloride (prepared as described in WO2006/119061) instead of methyl (2S,4R)-4-[(7-methoxy-2-phenyl-6-vinylquinolin-4-yl)oxy]-pyrrolidine-2-carboxylate hydrochloride. $^1$H NMR (400 MHz, DMSO-d$_6$) δ 10.50 (s, 1H), 8.93 (s, 1H), 7.91 (d, J 5.8, 1H), 7.78 (s, 1H), 7.31 (bs, 3H), 6.66 (d, J 16.4, 1H), 6.33 (s, 1H), 5.65 (m, 3H), 5.23 (d, J 17.4, 1H), 5.11 (d, J 10.6, 1H), 4.38 (d, J 12.4, 1H), 4.27 (m, 1H), 4.01 (m, 1H), 3.96 (s, 3H), 2.99 (m, 1H), 2.66 (m, 2H), 2.22-2.08 (m, 3H), 1.97-1.69 (m, 6H), 1.36 (s, 3H), 1.33-1.08 (m, 14H); MS (ES$^+$) C$_{41}$H$_{50}$N$_6$O$_7$S$_2$ requires: 803. Found: 804 (M+H).

Example 15

Table 3, Entry 13

(3R,5S,8S,16E)-8-cyclohexyl-N-((1R,2S)-1-{[(cyclopropylsulfonyl)amino]carbonyl}-2-vinylcyclopropyl)-19,23-dimethoxy-14,14-dimethyl-7-oxo-2-oxa-11-thia-6,9,22,27-tetraazapentacyclo[16.6.2.13, 5.110,13.021,25]octacosa-1(24),10(27),12,16,18,20, 22,25-octaene-5-carboxamide The title compound was prepared as described for Example 13, employing in Step 1 methyl (2S,4R)-1-[(2S)-2-amino-2-cyclohexylacetyl]-4-[(2,7-dimethoxy-6-vinyl-quinolin-4-yl) oxy]-]pyrrolidine-2-carboxylate hydrochloride (Intermediate 8, synthetic procedure described below) instead of methyl (2S,4R)-4-[(7-methoxy-2-phenyl-6-vinylquinolin-4-yl) oxy]-pyrrolidine-2-carboxylate hydrochloride. $^1$H NMR (400 MHz, DMSO-d$_6$) δ 10.52 (s, 1H), 8.91 (s, 1H), 7.59 (s, 1H), 7.11 (s, 1H), 6.66 (d, J 16.2, 1H), 6.43 (s, 1H), 6.33 (s, 1H), 5.67-5.51 (m, 2H), 5.46 (s, 1H), 5.22 (d, J 16.7, 1H), 5.11 (d, J 11.6, 1H), 4.41 (d, J 12.1, 1H), 4.21 (dd, J 10.2, 6.9, 1H), 4.03 (d, J 9.6, 1H), 3.98 (s, 3H), 3.93 (s, 3H), 2.98 (m, 1H), 2.63 (m, 2H), 2.18-2.08 (m, 3H), 1.97-1.62 (m, 6H), 1.36 (s, 3H), 1.31-1.07 (m, 14H); MS (ES$^+$) C$_{42}$H$_{52}$N$_6$O$_7$S$_2$ requires: 833. Found: 834 (M+H$^+$).

Intermediate 8: Methyl (2S,4R)-1-[(2S)-2-amino-2-cyclohexylacetyl]-4-[(2,7-dimethoxy-6-vinyl-quinolin-4-yl)oxy]-]pyrrolidine-2-carboxylate hydrochloride Step 1: Methyl (2S,4S)-4-[((4-bromophenyl)sulfonyl)oxy]pyrrolidine-2-carboxylate hydrochloride To a 0.22 M solution of 1-tert-butyl 2-methyl (2S,4S)-4-[((4-bromophenyl)sulfonyl)oxy]pyrrolidine-1,2-dicarboxylate (prepared as described in WO2006/119061) in Et$_2$O at 0° C. was added dropwise a 4M solution of HCl in dioxane (25 eq.) and the resulting mixture was stirred at RT for 16 h, after which time a solid product was formed. The suspension was filtered and the filter cake was washed with cold Et$_2$O. The solid product was dried in vacuo and the product used without further purification. MS (ES$^+$) C$_{12}$H$_{14}$BrNO$_5$S requires: 363. Found: 364, 365 (M+H$^+$).

Step 2: Methyl (2S,4S)-4-[((4-bromophenyl)sulfonyl)oxy]-1-[(2S)-2-[(tert-butoxycarbonyl)amino]-2-cyclohexylacetyl]pyrrolidine-2-carboxylate To a solution of proline derivative from Step 1 in DMF was added Boc-(L)-cyclohexylglycine (1.05 eq), followed by $^i$Pr$_2$NEt (3.5 eq) and TBTU (1.05 eq). The resulting reaction mixture was stirred 12 h at RT and partitioned between EtOAc and 1N aq. HCl. The organic layer was further washed with sat. aq. NaHCO$_3$, brine, dried (Na$_2$SO$_4$) and concentrated under reduced pressure. The residue was purified by SiO$_2$ gel chromatography (hexane/EtOAc=75/25) to give the title compound as an off-white foam. MS (ES$^+$) $C_{25}H_{35}BrN_2O_8S$ requires: 603. Found: 603,605 (M+H$^+$).

Step 3:
6-Bromo-4-hydroxy-7-methoxyquinolin-2(1H)-one

The title compound was prepared from 4-bromo-3-methoxyaniline according to the procedure reported by K. Faber, H. Steininger and T. Kappe, J. Het. Chem. 1985, 22 (4), 1081. MS (ES$^+$) $C_{10}H_8BrNO_3$ requires: 270. Found: 270, 272 (M+H$^+$).

Step 4: Methyl (2S,4R)-4-[(6-bromo-7-methoxy-2-oxo-1,2-dihydroquinolin-4-yl)oxy]-1-[(2S)-2-[(tert-butoxycarbonyl)amino]-2-cyclohexylacetyl]pyrrolidine-2-carboxylate To a 0.27 M solution of hydroxyl-quinolinone from Step 3 (1 eq.) and brosylate from Step 2 (1 eq.) in N-methyl-2-pyrrolidinone was added cesium carbonate (1.5 eq.) and the resulting mixture was heated at 60° C. for 16 h. The mixture was cooled to RT and partitioned between water and EtOAc. The organic phase was washed with brine, dried (Na$_2$SO$_4$) and the volatiles were removed under reduced pressure. The residue was purified by SiO$_2$ gel chromatography (eluting with 50% EtOAc/Hex and then 0-5% MeOH/DCM) to yield the title compound. MS (ES$^+$) $C_{29}H_{38}BrN_3O_8$ requires: 637. Found: 636, 638 (M+H$^+$).

Step 5: Methyl (2S,4R)-1-[(2S)-2-[(tert-butoxycarbonyl)amino]-2-cyclohexylacetyl]-4-[(7-methoxy-2-oxo-6-vinyl-1,2-dihydroquinolin-4-yl)oxy]-]pyrrolidine-2-carboxylate To a 0.25 M solution of arylbromide from Step 4 in EtOH was added potassium vinyl-trifluoroborate (1.1 eq.), Et$_3$N (1.5 eq.) and PdCl$_2$(dppf)-CH$_2$Cl$_2$ adduct (0.05 eq.). The resulting mixture was heated at 90° C. for 2.5 h. Two further aliquots of potassium vinyl-trifluoroborate (0.5 eq.), Et$_3$N (0.6 eq.) and the Pd catalyst (0.05 eq.) were added every 3.5 h in order to drive the reaction to completion. The mixture was cooled to RT and partitioned between water and EtOAc. The organic phase was washed with brine, dried (Na$_2$SO$_4$) and the volatiles were removed under reduced pressure. The residue was purified by SiO$_2$ gel chromatography (eluting with DCM/MeOH=95/5) to give the title compound as a pale orange foam. MS (ES$^+$) $C_{31}H_{41}N_3O_8$ requires: 583. Found: 584 (M+H$^+$).

Step 6: Methyl (2S,4R)-1-[(2S)-2-[(tert-butoxycarbonyl)amino]-2-cyclohexylacetyl]-4-[(2,7-dimethoxy-6-vinyl-quinolin-4-yl)oxy]-]pyrrolidine-2-carboxylate To a 0.04 M solution of intermediate from Step 5 in DCM was added trimethyloxonium tetrafluoborate (1.05 eq.) and the resulting mixture was stirred 16 h at RT. The mixture was partitioned between ss NaHCO$_3$ and DCM. The organic phase was washed with brine, dried (Na$_2$SO$_4$) and the volatiles were removed under reduced pressure. The residue was purified by SiO$_2$ gel chromatography (eluting with PE/AcOEt=7/3 to 6/4) to give the title compound as a colourless oil. MS (ES$^+$) $C_{32}H_{43}N_3O_8$ requires: 597. Found: 598 (M+H$^+$).

Step 7: Methyl (2S,4R)-1-[(2S)-2-amino-2-cyclohexylacetyl]-4-[(2,7-dimethoxy-6-vinyl-quinolin-4-yl)oxy]-]pyrrolidine-2-carboxylate hydrochloride Intermediate 8

A 0.09 M solution of Boc-protected intermediate from Step 6 in 4M HCl in dioxane was stirred at RT for 2 h. The volatiles were then removed under reduced pressure and the residue (white solid) was used without any further purification. MS (ES$^+$) $C_{27}H_{35}N_3O_6$ requires: 497. Found: 498 (M+H$^+$).

Example 16

Table 3, Entry 3-14

(1R,22S,25S)-22-cyclopentyl-N-((1R,2S)-1-{[cyclopropylsulfonyl)amino]carbonyl}-2-ethenylcyclopropyl)-3,23-dioxo-2,28-dioxa-4,18,19,21,24-pentaazapentacyclo[22.1.1$^{4,7}$.1$^{17,20}$.0$^{6,11}$]nonacosa-6,8,10,17,19-pentaene-25-carboxamide The title compound was prepared as described for Example 8, using in Step 1 hex-5-enoic acid instead of pent-4-enoic acid and in Step 6 Intermediate 7 instead of Intermediate 1. MS (ES$^+$) $C_{37}H_{47}N_7O_8S$ requires: 749. Found: 750 (M+H$^+$).

Example 17

Table 3, Entry 15

(1R,12E,22S,25S)-22-cyclopentyl-N-((1R,2S)-1-{[cyclopropylsulfonyl)amino]carbonyl}-2-ethenylcyclopropyl)-3,23-dioxo-2,28-dioxa-4,18,19,21,24-pentaazapentacyclo[22.1.1$^{4,7}$.1$^{17,20}$.0$^{6,11}$]nonacosa-6,8,10,12,17,19-hexaene-25-carboxamide The title compound was prepared as described for Example 8, using in Step 1 hex-5-enoic acid instead of pent-4-enoic acid and in Step 6 Intermediate 7 instead of Intermediate 1; the hydrogenation Step 8 described in Example 8 was not performed. MS (ES$^+$) $C_{37}H_{45}N_7O_8S$ requires: 747. Found: 748 (M+H$^+$).

Example 18

Table 3, Entry 16

(3R,5S,8S)—N-((1R,2S)-1-{[(cyclopropylsulfonyl)amino]carbonyl}-2-vinylcyclopropyl)-22-ethyl-8-isopropyl-7-oxo-2,27-dioxa-6,9,11,12,24-pentaazapentacyclo[16.6.2.1$^{3,6}$.1$^{10,13}$.0$^{21,25}$]octacosa-1(24),10,12,18,20,22,25-heptaene-5-carboxamide Step 1: methyl (3R,5S,8S)-8-isopropyl-7-oxo-22-vinyl-2,27-dioxa-6,9,11,12,24-pentaazapentacyclo[16.6.2.1$^{3,6}$.1$^{10,13}$.0$^{21,25}$]octacosa-1(24),10,12,18,20,22,25-heptaene-5-carboxylate To a 0.1 M solution of methyl (3R,5S,8S)-22-iodo-8-isopropyl-7-oxo-2,27-dioxa-6,9,11,12,24-pentaazapentacyclo

[16.6.2.1$^{3,6}$.1$^{10,13}$.0$^{21,25}$]octacosa-1(24), 10,12,18,20,22,25-heptaene-5-carboxylate (Example 12, Step 2) in dry toluene was added tetrakis(triphenylphosphine)palladium(0) (0.05 eq.). N$_2$ was bubbled through the reaction mixture for 5 minutes and tributylethenylstannane (1.5 eq) was added. The mixture was stirred at 100° C. for 1 h, allowed to cool to RT, diluted with EtOAc and washed with brine. The organic layer was separated, dried over Na$_2$SO$_4$, filtered and concentrated. The residue was purified on silica gel (20% to 40% EtOAc/ PE) to give the compound as a white solid. MS (ES$^+$) C$_{28}$H$_{33}$N$_5$O$_5$ requires: 519. Found: 520 (M+H$^+$).

Step 2: methyl (3R,5S,8S)-22-ethyl-8-isopropyl-7-oxo-2,27-dioxa-6,9,11,12,24-pentaazapentacyclo [16.6.2.1$^{3,6}$.1$^{10,13}$.0$^{21,25}$]octacosa-1(24),10,12,18,20,22,25-heptaene-5-carboxylate To a 9 mM solution of methyl (3R,5S,8S)-8-isopropyl-7-oxo-22-vinyl-2,27-dioxa-6,9,11,12,24-pentaazapentacyclo [16.6.2.1$^{3,6}$.1$^{10,13}$.0$^{21,25}$]octacosa-1(24),10,12,18,20,22,25-heptaene-5-carboxylate (from Step 1) in EtOH was added 10% Pd/C (0.1 eq) and the resulting reaction mixture was stirred at RT under H$_2$ atmosphere for 2 h. The catalyst was filtered off through a pad of CELITE and the volatiles were removed under reduced pressure to give the title compound as a colorless oil. MS (ES$^+$) C$_{28}$H$_{35}$N$_5$O$_5$ requires: 521. Found: 522 (M+H$^+$).

Step 3: (3R,5S,8S)-22-ethyl-8-isopropyl-7-oxo-2,27-dioxa-6,9,11,12,24-pentaazapentacyclo[16.6.2. 1$^{3,6}$.1$^{10,13}$.0$^{21,25}$]octacosa-1(24),10,12,18,20,22,25-heptaene-5-carboxylic acid To a solution of methyl (3R,5S,8S)-22-ethyl-8-isopropyl-7-oxo-2,27-dioxa-6,9,11,12,24-pentaazapentacyclo [16.6.2.1$^{3,6}$.1$^{10,13}$.0$^{21,25}$]octacosa-1(24),10,12,18,20,22,25-heptaene-5-carboxylate (from Step 2) in THF/H$_2$O (1/1 v/v) was added LiOH (4 eq). The resulting reaction mixture was stirred at RT for 2 h and then treated with 1N aq. HCl until pH=2 was reached. The aqueous phase was extracted with EtOAc, the organic layer was separated, dried over Na$_2$SO$_4$, filtered and concentrated to give a white solid. MS (ES$^+$) C$_{27}$H$_{33}$N$_5$O$_5$ requires: 507. Found: 508 (M+H$^+$).

Step 4: (3R,5S,8S)—N-((1R,2S)-1-{[(cyclopropylsulfonyl)amino]carbonyl}-2-vinylcyclopropyl)-22-ethyl-8-isopropyl-7-oxo-2,27-dioxa-6,9,11,12,24-pentaazapentacyclo[16.6.2.1$^{3,6}$.1$^{10,13}$.0$^{21,25}$] octacosa-1(24),10,12,18,20,22,25-heptaene-5-carboxamide (3R,5S,8S)-22-ethyl-8-isopropyl-7-oxo-2,27-dioxa-6,9, 11,12,24-pentaazapentacyclo[16.6.2.1$^{3,6}$.1$^{10,13}$.0$^{21,25}$]octacosa-1(24),10,12,18,20,22,25-heptaene-5-carboxylic acid (from Step 3) was dissolved in DMF and to this solution was added Intermediate 2 followed by $^i$Pr$_2$NEt (3.5 eq) and TBTU (1.09 eq). The resulting reaction mixture was stirred 12 h at RT and purified by reverse phase HPLC to give the title compound as a white solid. $^1$H NMR (600 MHz, DMSO-d$_6$) δ 10.33 (s, 1H), 8.92 (s, 1H), 7.96 (d, J 9.7, 1H), 7.87 (d, J 8.6, 1H), 7.78 (s, 1H), 7.71 (s, 1H), 7.63 (dd, J 8.6, 1.5, 1H), 5.71 (s, 1H), 5.59 (m, 1H), 5.20 (d, J 17.2, 1H), 5.08 (d, J 10.2, 1H), 4.88 (d, J 10.8, 1H), 4.20 (dd, J 11.3, 7.2, 1H), 4.17 (t, J 9.6, 1H), 3.96 (dd, J 11.4, 3.4, 1H), 2.94-2.86 (m, 4H), 2.76 (m, 1H), 2.64 (m, 1H), 2.18-2.09 (m, 3H), 1.75-1.69 (m, 3H), 1.67-1.62 (m, 2H), 1.39-1.36 (m, 2H), 1.29-1.24 (m, 4H), 1.10-1.08 (m, 2H), 1.04-1.03 (m, 2H), 1.00 (t, J 6.6, 3H), 0.96 (d, J 6.6, 3H). MS (ES$^+$) C$_{36}$H$_{45}$N$_7$O$_7$S requires: 719. Found: 720 (M+H$^+$).

The following tables list specific compounds of the present invention. The tables provide the structure and name of each compound and the mass of its molecular ion plus 1 (M+1) as determined via ES-MS. The synthetic scheme employed to prepare the compound is indicated in the last column.

TABLE 1

| Entry | Compound name | Structure | M + 1 | Preparative method |
|---|---|---|---|---|
| 1-1 | (3R,5S,8S)-N((1R,2S)-1-{[(cyclopropylsulfonyl)amino]carbonyl}-2-ethenylcyclopropyl)-8-(1-methylethyl)-7-oxo-2-oxa-11-thia-6,9,24,27-tetraazapentacyclo[16.6.2.1$^{3,6}$.1$^{10,13}$.0$^{21,25}$]octacosa-1(24),10(27),12,18,20,22,25-heptaene-5-carboxamide | 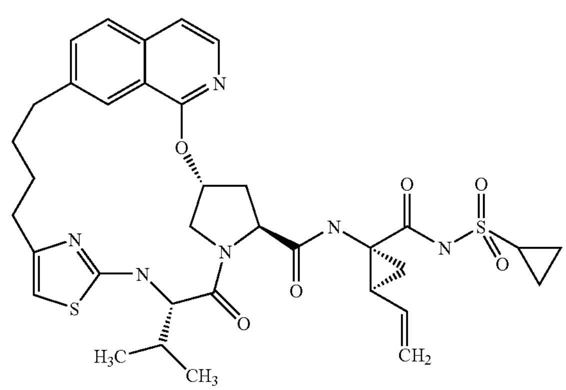 | 707 | Scheme 1 |

TABLE 1-continued

| Entry | Compound name | Structure | M + 1 | Preparative method |
|---|---|---|---|---|
| 1-2 | (3R,5S,8S)-N-((1R,2S)-1-{[(cyclopropylsulfonyl)amino]carbonyl}-2-ethenylcyclopropyl)-8-(1-methylethyl)-7-oxo-2-oxa-11-thia-6,9,25,28-tetraazapentacyclo[17.6.2.1³,⁶.1¹⁰,¹³.0²²,²⁶]nonacosa-1(25),10(28),12,19,21,23,26-heptaene-5-carboxamide | 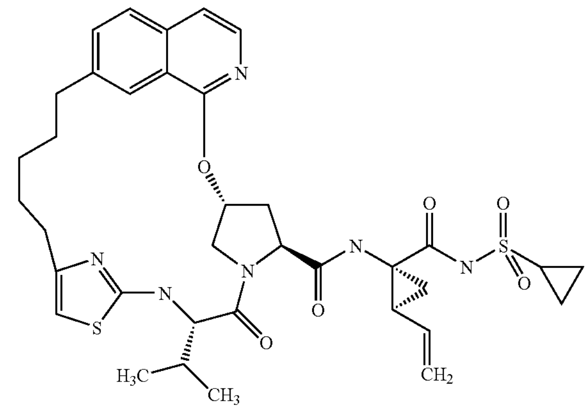 | 721 | Scheme 1 |
| 1-3 | (3R,5S,8S)-N-((1R,2S)-1-{[(cyclopropylsulfonyl)amino]carbonyl}-2-ethenylcyclopropyl)-8-(1-methylethyl)-7-oxo-23-phenyl-2-oxa-11-thia-6,9,22,27-tetraazapentacyclo[16.6.2.1³,⁶.1¹⁰,¹³.0²¹,²⁵]octacosa-1(24),10(27),12,18,20,22,25-heptaene-5-carboxamide | 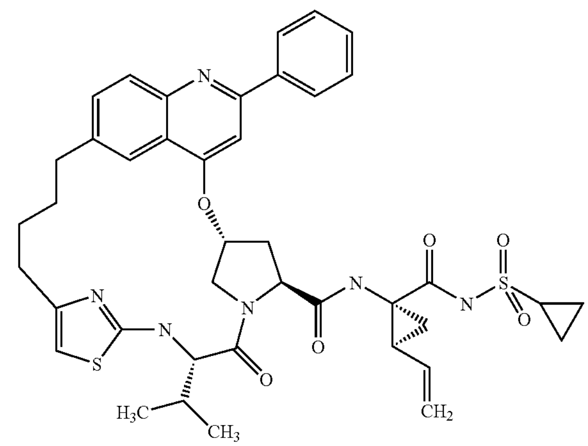 | 783 | Scheme 1 |
| 1-4 | (3R,5S,8S,16E)-N-((1R,2S)-1-{[(cyclopropylsulfonyl)amino]carbonyl}-2-ethenylcyclopropyl)-8-(1,1-dimethylethyl)-7-oxo-2-oxa-11-thia-6,9,24,27-tetraazapentacyclo[16.6.2.1³,⁶.1¹⁰,¹³.0²¹,²⁵]octacosa-1(24),10(27),12,16,18,20,22,25-octaene-5-carboxamide | 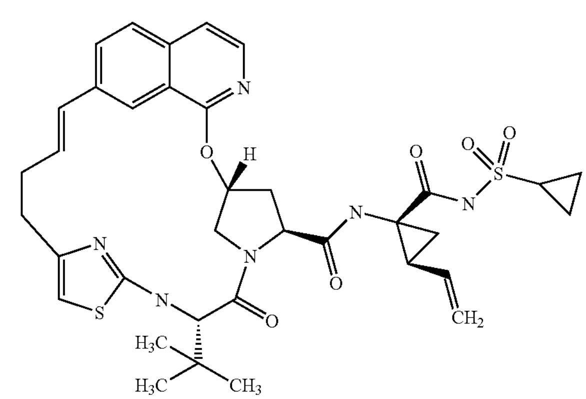 | 719 | Scheme 1 |

TABLE 1-continued

| Entry | Compound name | Structure | M + 1 | Preparative method |
|---|---|---|---|---|
| 1-5 | (3R,5S,8S,16Z)-N-((1R,2S)-1-{[cyclopropylsulfonyl)amino]carbonyl}-2-ethenylcyclopropyl)-8-(1,1-dimethylethyl)-7-oxo-2-oxa-11-thia-6,9,24,27-tetraazapentacyclo[16.6.2.1$^{3,6}$.1$^{10,13}$.0$^{21,25}$]octacosa-1(24),10(27),12,16,18,20,22,25-octaene-5-carboxamide | 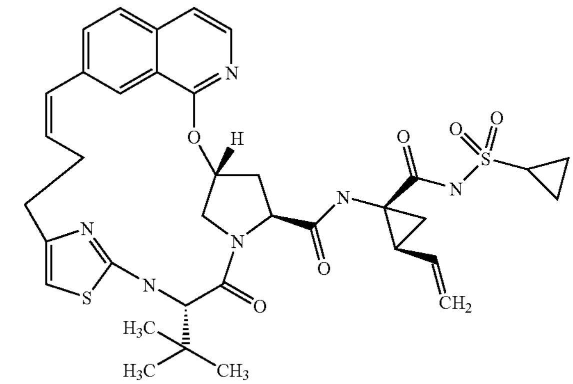 | 719 | Scheme 1 |
| 1-6 | (3R,5S,8S)-N-(1R,2S)-1-{[cyclopropylsulfonyl)amino]carbonyl}-2-ethenylcyclopropyl)-8-(1,1-dimethylethyl)-7-oxo-2-oxa-11-thia-6,9,24,27-tetraazapentacyclo[16.6.2.1$^{3,6}$.1$^{10,13}$.0$^{21,25}$]octacosa-1(24),10(27),12,16,18,20,22,25-octaene-5-carboxamide | 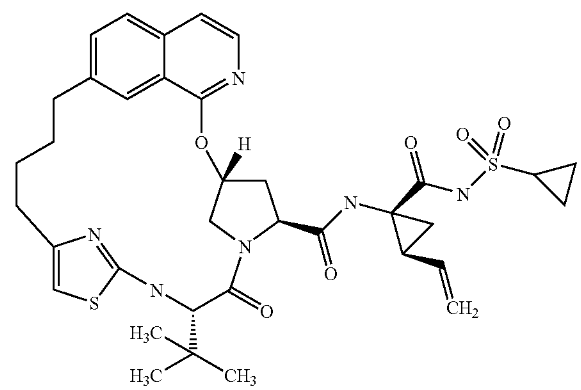 | 721 | Scheme 1 |
| 1-7 | (1R,12E,21S,24S)-N-((1R,2S)-1-{[(cyclopropylsulfonyl)amino]carbonyl}-2-ethenylcyclopropyl)-21-(1-methylethyl)-3,22-dioxo-2-oxa-18-thia-4,20,23,27-tetraazapentacyclo[21.2.1$^{4,7}$.1$^{16,19}$.0$^{6,11}$]octacosa-6,8,10,12,16,19(27)-hexaene-24-carboxamide | 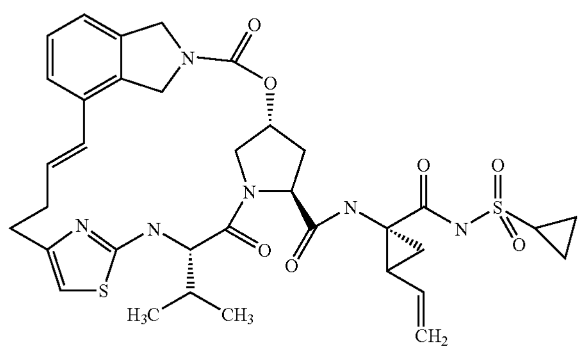 | 723 | Scheme 2 |
| 1-8 | (1R,12E,22S,25S)-N-((1R,2S)-1-{[(cyclopropylsulfonyl)amino]carbonyl}-2-ethenylcyclopropyl)-22-(1-methylethyl)-3,23-dioxo-2-oxa-19-thia-4,21,24,28-tetraazapentacyclo[22.2.1$^{4,7}$.1$^{17,20}$.0$^{6,11}$]octacosa-6,8,10,12,17,20(28)-hexaene-25-carboxamide | 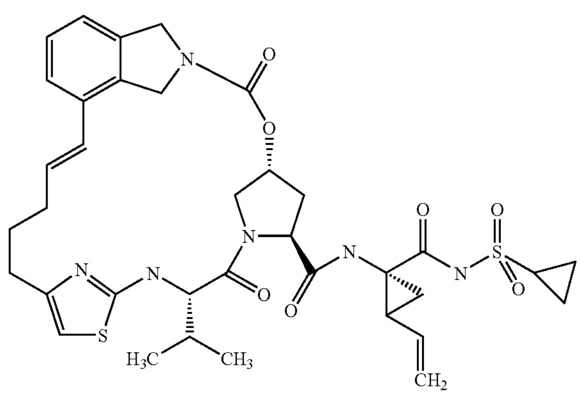 | 737 | Scheme 2 |

TABLE 1-continued

| Entry | Compound name | Structure | M + 1 | Preparative method |
|---|---|---|---|---|
| 1-9 | (1R,22S,25S)-N-((1R,2S)-1-{[(cyclopropylsulfonyl)amino]carbonyl}-2-ethenylcyclopropyl)-22-(1,1-dimethylethyl)-3,23-dioxo-2-oxa-19-thia-4,21,24,28-tetraazapentacyclo[22.2.1$^{4,7}$.1$^{17,20}$.0$^{6,11}$]nonaacosa-6,8,10,17,20(28)-pentaene-25-carboxamide | 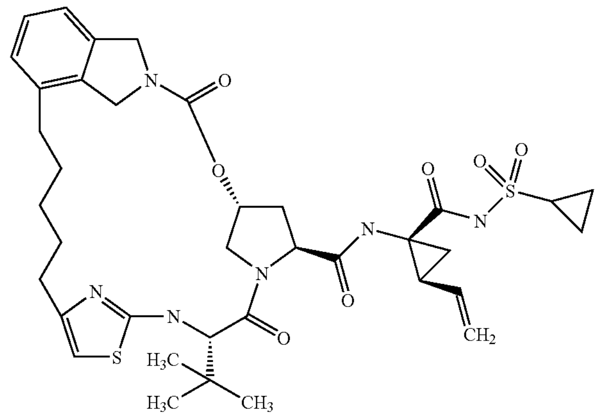 | 753 | Scheme 2 |
| 1-10 | (1R,12E,22S,25S)-N-((1R,2S)-1-{[(cyclopropylsulfonyl)amino]carbonyl}-2-ethenylcyclopropyl)-22-(1,1-dimethylethyl)-3,23-dioxo-2-oxa-19-thia-4,21,24,28-tetraazapentacyclo[22.2.1$^{4,7}$.1$^{17,20}$.0$^{6,11}$]nonaacosa-6,8,10,12,17,20(28)-hexaene-25-carboxamide | 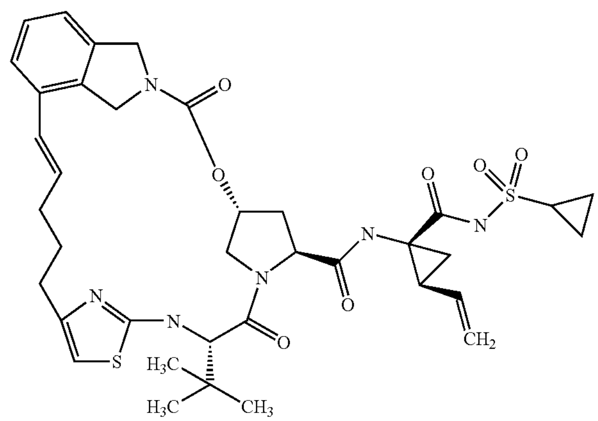 | 751 | Schem 2 |
| 1-11 | (1R,12E,22S,25S)-22-cyclohexenyl-N-((1R,2S)-1-{[(cyclopropylsulfonyl)amino]carbonyl}-2-ethenylcyclopropyl)-3,23-dioxo-2-oxa-19-thia-4,21,24,28-tetraazapentacyclo[22.2.1$^{4,6}$.1$^{17,20}$.0$^{6,11}$]nonaacosa-6,8,10,12,17,20(28)-hexaene-25-carboxamide | 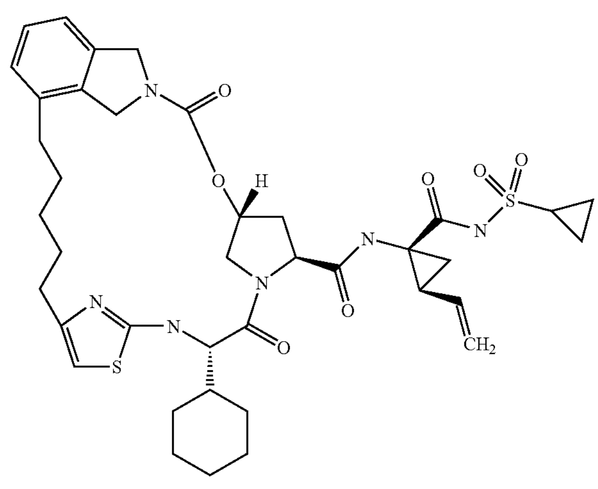 | 777 | Scheme 2 |

TABLE 1-continued

| Entry | Compound name | Structure | M + 1 | Preparative method |
|---|---|---|---|---|
| 1-12 | (1R,22S,25S)-22-cyclohexyl-N-((1R,2S)-1-{[(cyclopropylsulfonyl)amino]carbonyl}-2-ethenylcyclopropyl)-3,23-dioxo-2-oxa-19-thia-4,21,24,28-tetraazapentacyclo[22.2.1$^{4,7}$.1$^{17,20}$.0$^{6,11}$]nonaacosa-6,8,10,17,20(28)-pentaene-25-carboxamide | 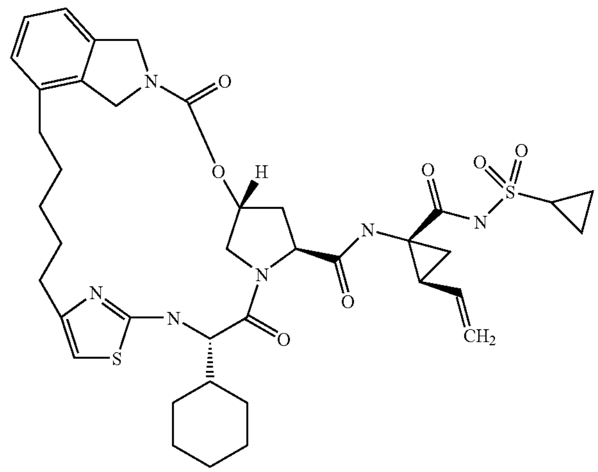 | 779 | Scheme 2 |
| 1-13 | (3R,5S,8S)-8-cyclohexyl-N-((1R,2S)-1{[(cyclopropylsulfonyl)amino]carbonyl}-2-ethenylcyclopropyl)-7-oxo-2-oxa-11-thia-6,9,24,27-tetraazapentacyclo[16.6.2.1$^{3,6}$.1$^{10,13}$.0$^{21,25}$]octacosa-1(24),10(27),12,18,20,22,25-heptaene-5-carboxamide | 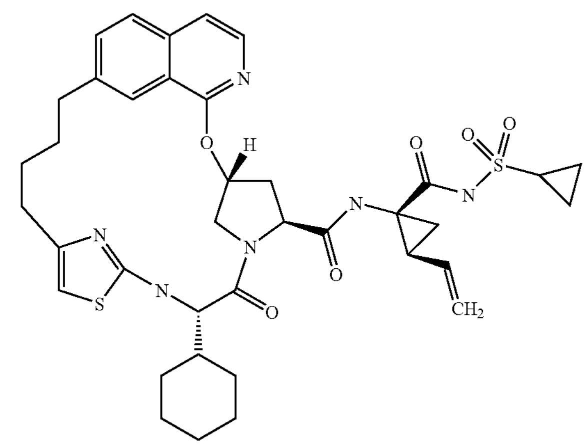 | 747 | Scheme 2 |
| 1-14 | (1R,12E,22S,25S)-N-((1R,2S)-1-{[(cyclopropylsulfonyl)amino]carbonyl}-2-ethenylcyclopropyl)-22-[(1R)-1-methylpropyl]-3,23-dioxo-2-oxa-19-thia-4,21,24,28-tetraazapentacyclo[22.2.1$^{4,7}$.1$^{17,20}$.0$^{6,11}$]nonaacosa-6,8,10,12,17,20(28)-hexaene-25-carboxamide | 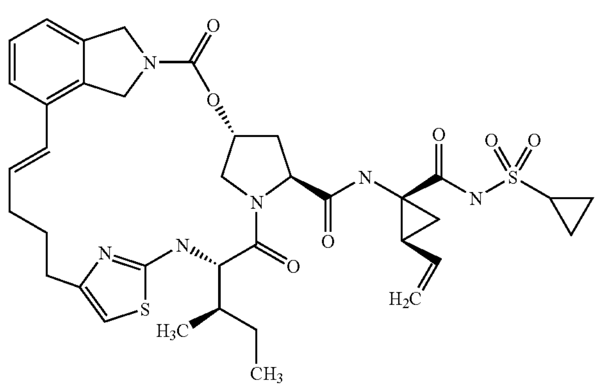 | 751 | Scheme 2 |

TABLE 1-continued

| Entry | Compound name | Structure | M + 1 | Preparative method |
|---|---|---|---|---|
| 1-14a | (1R,12E,22S,25S)-N-((1R,2S)-1-{[(cyclopropylsulfonyl)amino]carbonyl}-2-ethenylcyclopropyl)-22-[(1S)-1-methylpropyl]-3,23-dioxo-2-oxa-19-thia-4,21,24,28-tetraazapentacyclo[22.2.1⁴,⁷.1¹⁷,²⁰.0⁶,¹¹]nonaacosa-6,8,10,12,17,20(28)-hexaene-25-carboxamide | 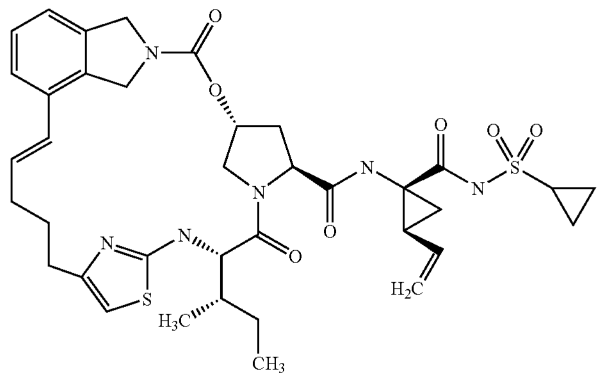 | 751 | Scheme 2 |
| 1-15 | (3R,5S,8S,16E)-N-(1R,2S)-1-{[(cyclopropylsulfonyl)amino]carbonyl}-2-ethenylcyclopropyl]-8-[(1R)-1-methylpropyl]-7-oxo-2-oxa-11-thia-6,9,24,27-tetraazapentacyclo[16.6.2.1³,⁶.1¹⁰,¹³.0²¹,²⁵]octacosa-1(24),10(27),12,16,18,20,22,25-octaene-5-carboxamide | 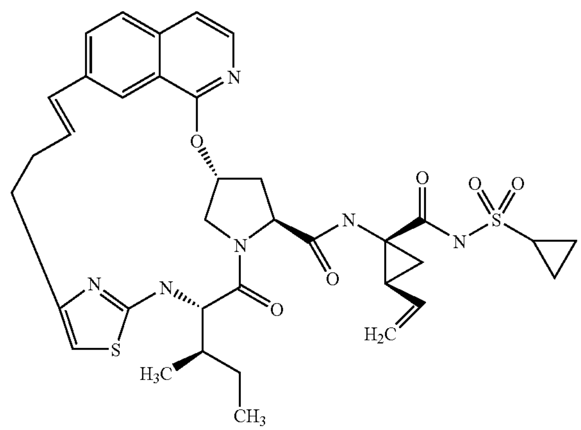 | 719 | Scheme 1 |
| 1-15a | (3R,5S,8S,16E)-N-((1R,2S)-1-{[(cyclopropylsulfonyl)amino]carbonyl}-2-ethenylcyclopropyl)-8-[(1S)-1-methylpropyl]-7-oxo-2-oxa-11-thia-6,9,24,27-tetraazapentacyclo[16.6.2.1³,⁶.1¹⁰,¹³.0²¹,²⁵]octacosa-1(24),10(27),12,16,18,20,22,25-octaene-5-carboxamide | 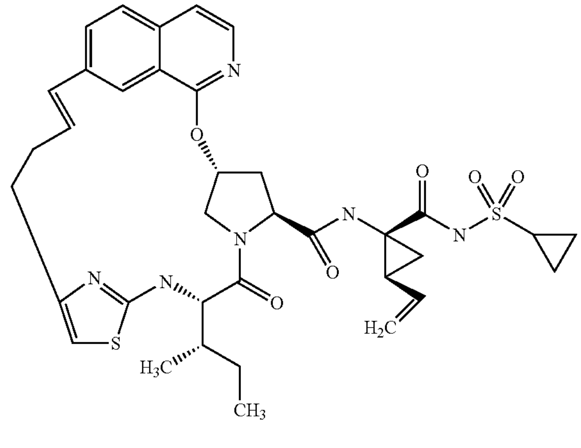 | 719 | Scheme 1 |

TABLE 1-continued

| Entry | Compound name | Structure | M + 1 | Preparative method |
|---|---|---|---|---|
| 1-16 | (1R,12E,22S,25S)-22-cyclohexyl-N-((1R,2R)-1-{[(cyclopropylsulfonyl)amino]carbonyl}-2-ethylcyclopropyl)-3,23-dioxo-2-oxa-19-thia-4,21,24,28-tetraazapentacyclo[22.2.1$^{4,7}$.1$^{17,20}$.0$^{6,11}$]nonaacosa-6,8,10,12,17,20(28)-hexaene-25-carboxamide | 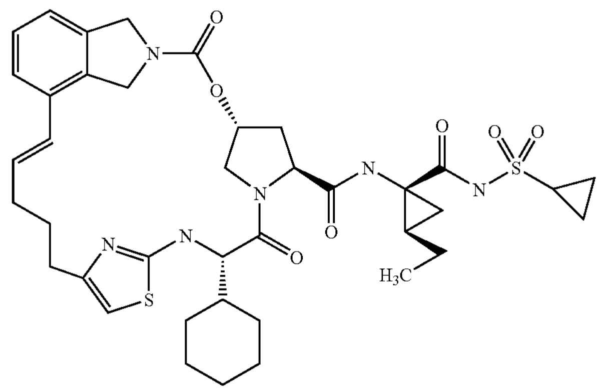 | 779 | Scheme 2 |
| 1-17 | (3R,5S,8S,16E)-N-((1R,2S)-1-{[(cyclopropylsulfonyl)amino]carbonyl}-2-ethenylcyclopropyl)-14,14-dimethyl-8-(1-methylethyl)-7-oxo-2-oxa-11-thia-6,9,24,27-tetraazapentacyclo[16.6.2.1$^{3,6}$.1$^{10,13}$.0$^{21,25}$]octacosa-1(25),10(27),12,16,18,20,21,23,25-nonaene-5-carboxamide | 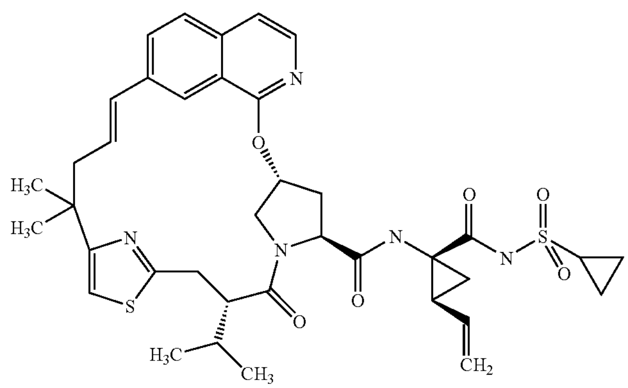 | 733 | Scheme 1 |
| 1-18 | (1R,12E,22S,25S)-22-cyclohexenyl-N-((1R,2S)-1-{[(cyclopropylsulfonyl)amino]carbonyl}-2-ethenylcyclopropyl)-3,23-dioxo-2,15-dioxa-19-thia-4,21,24,28-tetraazapentacyclo[22.2.1$^{4,7}$.1$^{17,20}$.0$^{6,11}$]nonaacosa-6,8,10,12,17,20(28)-hexaene-25-carboxamide | 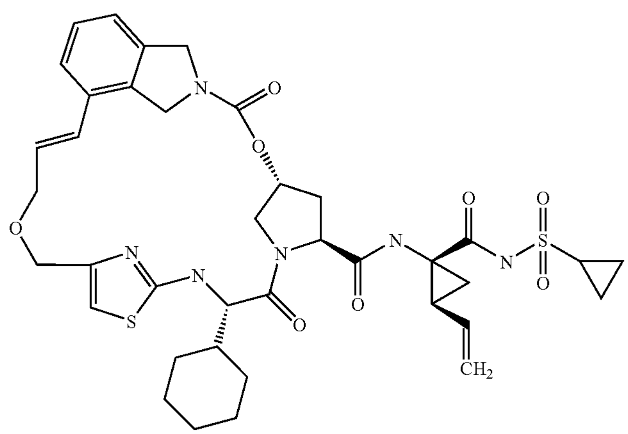 | 779 | Scheme 2 |
| 1-19 | (1R,22S,25S)-22-cyclohexenyl-N-((1R,2R)-1-{[(cyclopropylsulfonyl)amino]carbonyl}-2-ethylcyclopropyl)-3,23-dioxo-2-oxa-19-thia-4,21,24,28-tetraazapentacyclo[22.2.1$^{4,7}$.1$^{17,20}$.0$^{6,11}$]nonaacosa-6,8,10,17,20(28)-pentaene-25-carboxamide | 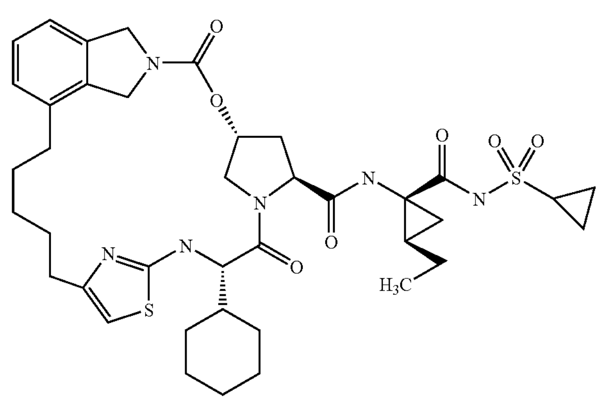 | 781 | Scheme 2 |

… TABLE 1-continued

| Entry | Compound name | Structure | M + 1 | Preparative method |
|---|---|---|---|---|
| 1-20 | (3R,5S,8S)-N-((1R,2S)-1-{[(cyclopropylsulfonyl)amino]carbonyl}-2-ethenylcyclopropyl)-14,14-dimethyl-8-(1-methylethyl)-7-oxo-2-oxa-11-tnia-6,9,24,27-tetraazapentacyclo[16.6.2.1$^{3,6}$.1$^{10,13}$.0$^{21,25}$]octacosa-1(25),10(27),12,18,20,21,23,25-octaene-5-carboxamide | 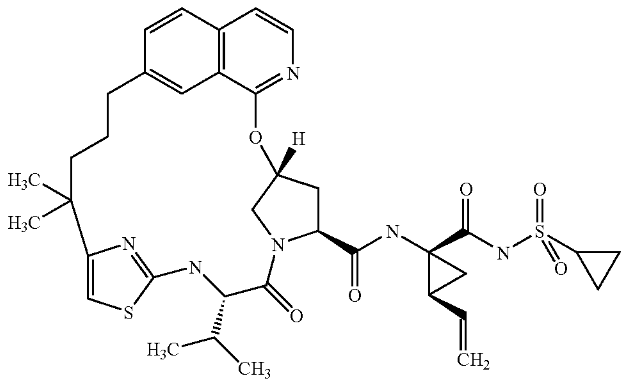 | 735 | Scheme 1 |

TABLE 2

| Entry | Compound name | Structure | M + 1 | Preparative method |
|---|---|---|---|---|
| 2-1 | (3R,5S,8S)-N-((1R,2S)-1-{[(cyclopropylsulfonyl)amino]carbonyl}-2-ethenylcyclopropyl)-8-isopropyl-7-oxo-2,27-dioxa-6,9,11,12,24-pentazapentacyclo[16.6.2.1$^{3,6}$.1$^{10,13}$.0$^{21,25}$]octacosa-1(24),10,12,18,20,22,25-heptaene-5-carboxamide | 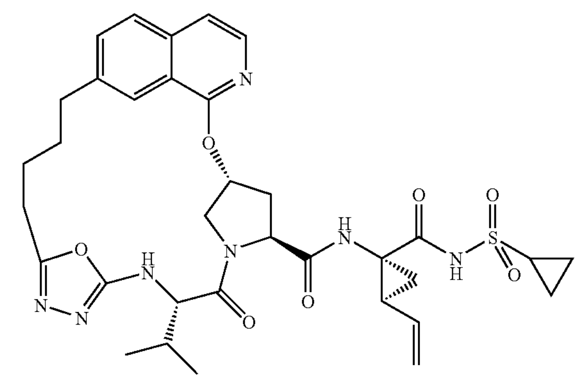 | 692 | Scheme 3 |
| 2-2 | (5S,8S)-N-((1R,2S)-2-ethenyl-1-{[(cyclopropylsulfonyl)amino]carbonyl}-2-ethenylcyclopropyl)-8-(1-methylethyl)-7-oxo-2,28-dioxa-6,9,11,12,25-pentaazapentacyclo[17.6.2.1$^{3,6}$.1$^{10,13}$.0$^{22,26}$]nonacosa-1(25),10,12,19,21,23,26-heptaene-5-carboxamide | 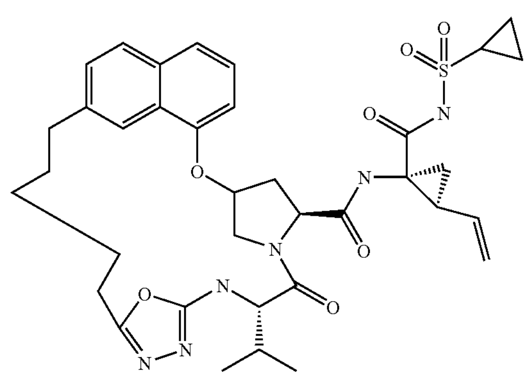 | 706 | Scheme 3 |

TABLE 2-continued

| Entry | Compound name | Structure | M + 1 | Preparative method |
|---|---|---|---|---|
| 2-3 | (1R,12E,22S,25S)-22-cyclohexyl-N-((1R,2S)-1-{[cyclopropylsulfonyl)amino]carbonyl}-2-ethenylcyclopropyl)-3,23-dioxo-2,28-dioxa-4,18,19,21,24-pentaazapentacyclo[22.1$^{4,7}$.1$^{17,20}$.0$^{6,11}$]nonacosa-6,8,10,12,17,19-hexaene-25-carboxamide | 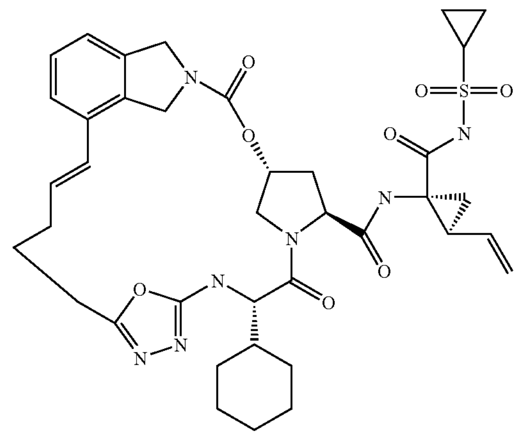 | 762 | Scheme 3 |
| 2-4 | (1R,22S,25S)-22-cyclohexyl-N-((1R,2S)-1-{[cyclopropylsulfonyl)amino]carbonyl}-2-ethenylcyclopropyl)-3,23-dioxo-2,28-dioxa-4,18,19,21,24-pentaazapentacyclo[22.1$^{4,7}$.1$^{17,20}$.0$^{6,11}$]nonacosa-6,8,10,17,19-pentaene-25-carboxamide | 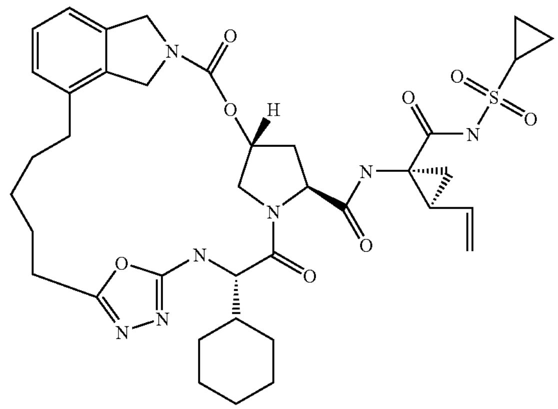 | 764 | Scheme 3 |
| 2-5 | (3R,5S,8S)-N-((1R,2S)-1-{[(cyclopropylsulfonyl)amino]carbonyl}-2-ethenylcyclopropyl)-23-iodo-8-isopropyl-7-oxo-2,28-dioxa-6,9,11,12,25-pentazapentacyclo[17.6.2.1$^{3,6}$.1$^{10,13}$.0$^{21,26}$]nonacosa-1(25),10,12,19,21,23,26-heptaene-5-carboxamide | 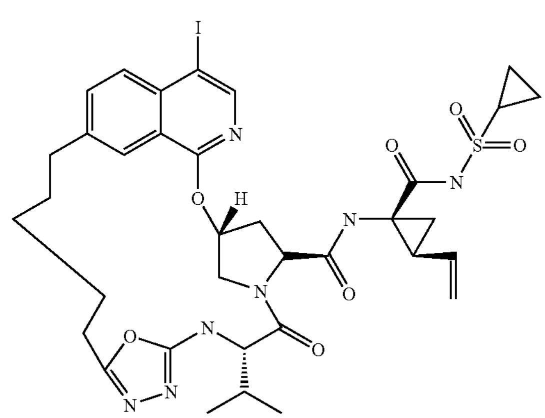 | 832 | Scheme 3 |

TABLE 3

| Entry | Compound name | Structure | M + 1 | Preparative method |
|---|---|---|---|---|
| 3-1 | (1R,12E,22S,25S)-22-cyclopentyl-N-((1R,2S)-1-{[(cyclopropylsulfonyl)amino]carbonyl}-2-vinylcyclopropyl)-3,23-dioxo-2-oxa-19-thia-4,21,24,28-tetraazapentacyclo[22.2.1.1<sup>4,7</sup>.1<sup>17,20</sup>.0<sup>6,11</sup>]nonacosa-6,8,10,12,17,20(28)-hexaene-25-carboxamide | 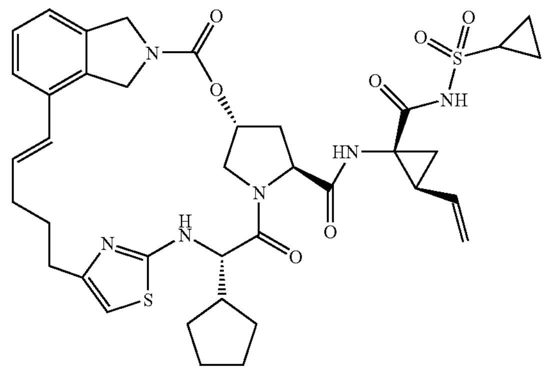 | 764 | Scheme 2 |
| 3-2 | (1R,12E,21S,24S)-21-cyclohexyl-N-((1R,2S)-1-{[(cyclopropylsulfonyl)amino]carbonyl}-2-vinylcyclopropyl)-15,15-dimethyl-3,22-dioxo-2-oxa-18-thia-4,20,23,27-tetraazapentacyclo[22.2.1.1<sup>4,7</sup>.1<sup>16,19</sup>.0<sup>6,11</sup>]octacosa-6,8,10,12,16,19(27)-hexaene-24-carboxamide | 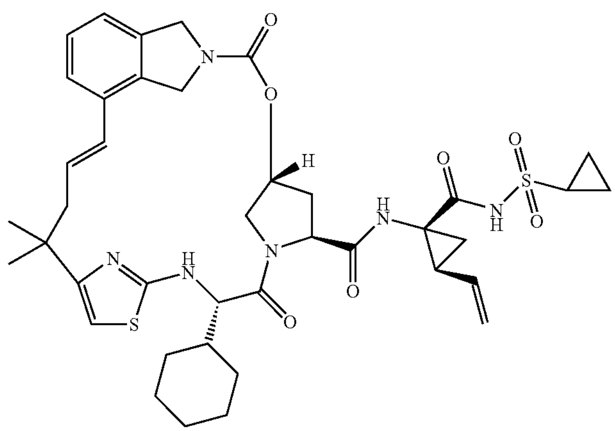 | 792 | Scheme 2 |
| 3-3 | (3R,5E,8S,16E)-8-cyclopentyl-N-((1R,2S)-1-{[(cyclopropylsulfonyl)amino]carbonyl}-2-vinylcyclopropyl)-7-oxo-2-oxa-11-thia-6,9,24,27-tetraazapentacyclo[16.6.2.1<sup>3,5</sup>.1<sup>10,13</sup>.0<sup>21,25</sup>]octacosa-1(24),10(27),12,16,18,20,22,25-octaene-5-carboxamide | 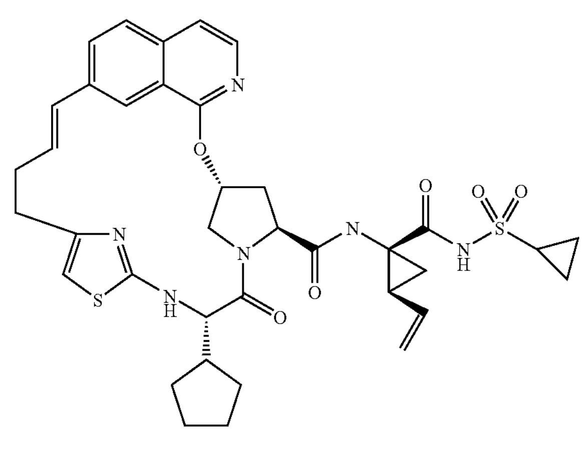 | 731 | Scheme 1 |

TABLE 3-continued

| Entry | Compound name | Structure | M + 1 | Preparative method |
|---|---|---|---|---|
| 3-4 | (1R,12E,21S,24S)-21-cyclopentyl-N-((1R,2S)-1-{[(cyclopropylsulfonyl)amino]carbonyl}-2-vinylcyclopropyl)-15,15-dimethyl-3,22-dioxo-2-oxa-18-thia-4,20,23,27-tetraazapentacyclo[22.2.1.1 4,7.1 16,19.0 6,11]octacosa-6,8,10,12,16,19(27)-hexaene-24-carboxamide | 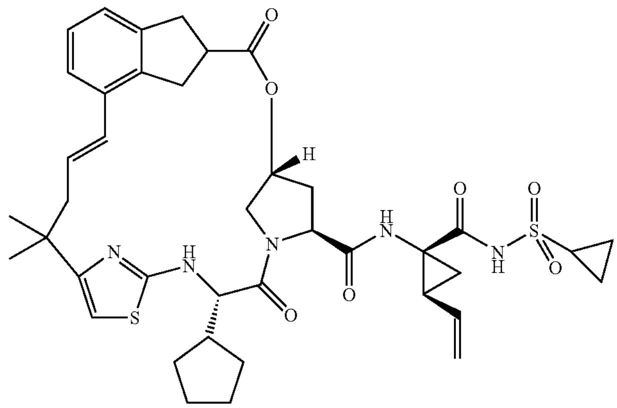 | 777 | Scheme 2 |
| 3-5 | (3R,5S,8S,16E)-N-((1R,2S)-1-{[(cyclopropylsulfonyl)amino]carbonyl}-2-vinylcyclopropyl)-8-isopropyl-7-oxo-2-oxa-11-thia-6,9,24,27-tetraazapentacyclo[16.6.2.1 3,5.1 10,13.0 21,25]octacosa-1(24),10(27),12,16,18,20,21,23,25-nonaene-5-carboxamide | 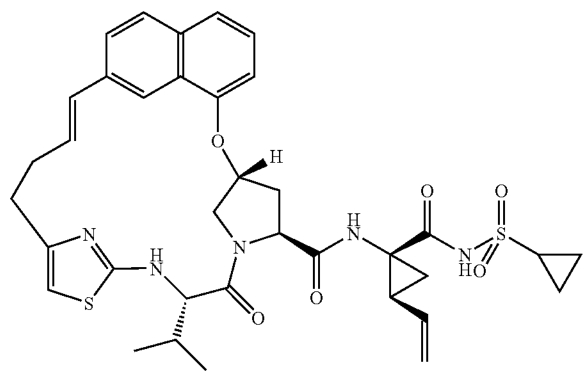 | 706 | Scheme 1 |
| 3-6 | (3R,5S,8S,16E)-8-cyclopentyl-N-((1R,2S)-1-{[(cyclopropylsulfonyl)amino]carbonyl}-2-vinylcyclopropyl)-19-methoxy-14,14-dimethyl-7-oxo-23-phenyl-2-oxa-11-thia-6,9,22,27-tetraazapentacyclo[16.6.2.1 3,5.1 10,13.0 21,25]octacosa-1(24),10(27),12,16,18,20,22,25-octaene-5-carboxamide | 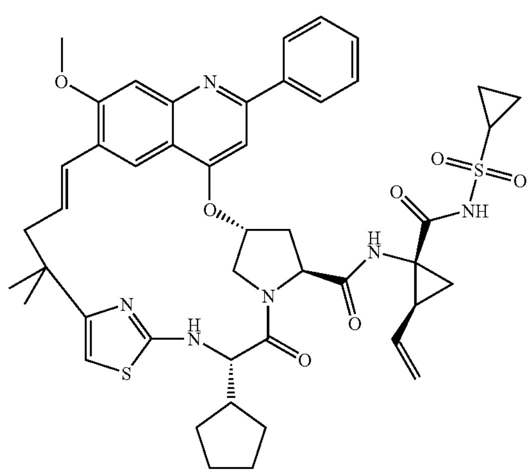 | 866 | Scheme 4 |

TABLE 3-continued

| Entry | Compound name | Structure | M + 1 | Preparative method |
|---|---|---|---|---|
| 3-7 | (3R,5S,8S,16E)-8-[(1S-)-1-methylpropyl]-N-((1R,2S)-1-{[(cyclopropylsulfonyl)amino]carbonyl}-2-vinylcyclopropyl)-19-methoxy-14,14-dimethyl-7-oxo-23-phenyl-2-oxa-11-thia-6,9,22,27-tetraazapentacyclo[16.6.2.13,5.110,13.021,25]octacosa-1(24),10(27),12,16,18,20,22,25-octaene-5-carboxamide | 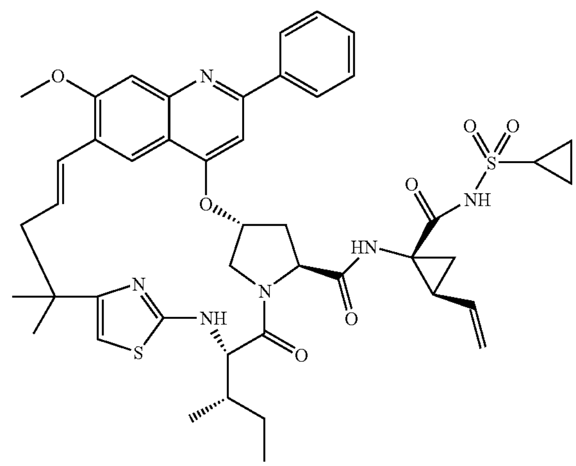 | 853 | Scheme 4 |
| 3-8 | (3R,5S,8S,16E)-8-cyclopentyl N-((1R,2S)-1-{[(cyclopropylsulfonyl)amino]carbonyl}-2-vinylcyclopropyl)-19-methoxy-7-oxo-23-phenyl-2-oxa-11-thia-6,9,22,27-tetraazapentacyclo[16.6.2.13,5.110,13.021,25]octacosa-1(24),10(27),12,16,18,20,22,25-octaene-5-carboxamide | 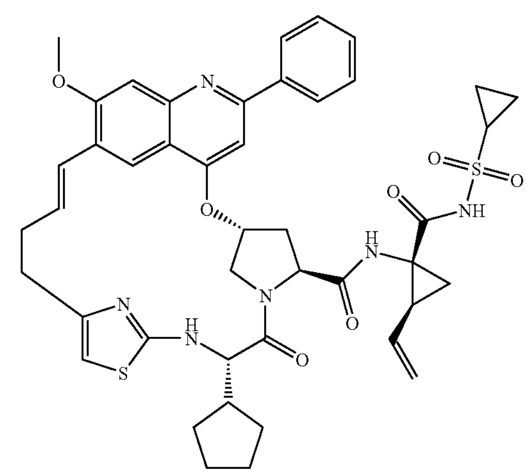 | 838 | Scheme 4 |
| 3-9 | (3R,5S,8S,16Z)-8-cyclopentyl N-((1R,2S)-1-{[(cyclopropylsulfonyl)amino]carbonyl}-2-vinylcyclopropyl)-19-methoxy-7-oxo-23-phenyl-2-oxa-11-thia-6,9,22,27-tetraazapentacyclo[16.6.2.13,5.110,13.021,25]octacosa-1(24),10(27),12,16,18,20,22,25-octaene-5-carboxamide | 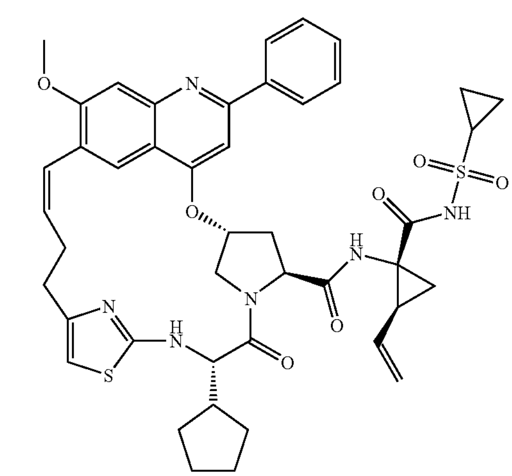 | 838 | Scheme 4 |

TABLE 3-continued

| Entry | Compound name | Structure | M + 1 | Preparative method |
|---|---|---|---|---|
| 3-10 | (3R,5S,8S,16E)-8-cyclohexyl-N-((1R,2S)-1-{[(cyclopropylsulfonyl)amino]carbonyl}-2-vinylcyclopropyl)-19-methoxy-14,14-dimethyl-7-oxo-23-phenyl-2-oxa-11-thia-6,9,22,27-tetraazapentacyclo[16.6.2.13,5.110,13.021,25]octacosa-1(24),10(27),12,16,18,20,22,25-octaene-5-carboxamide | 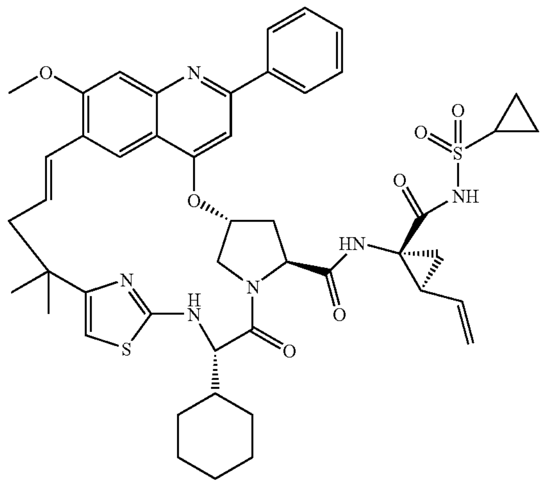 | 880 | Scheme 4 |
| 3-11 | (3R,5S,8S,16E)-8-cyclohexyl-N-((1R,2S)-1-{[(cyclopropylsulfonyl)amino]carbonyl}-2-vinylcyclopropyl)-19-methoxy-14,14-dimethyl-7-oxo-2-oxa-11-thia-6,9,24,27-tetraazapentacyclo[16.6.2.13,5.110,13.021,25]octacosa-1(24),10(27),12,16,18,20,22,25-octaene-5-carboxamide | 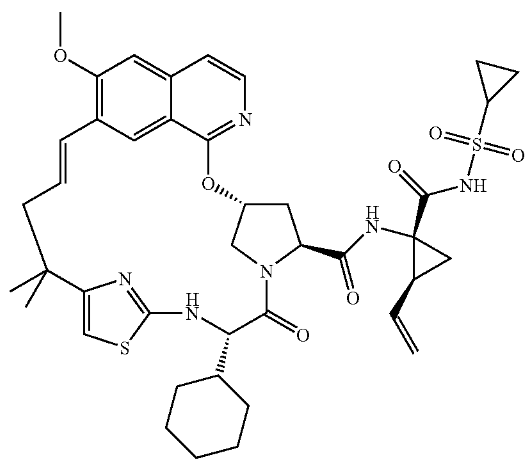 | 804 | Scheme 4 |
| 3-12 | (3R,5S,8S,16E)-8-cyclohexyl-N-((1R,2S)-1-{[(cyclopropylsulfonyl)amino]carbonyl}-2-vinylcyclopropyl)-19-methoxy-7-oxo-2-oxa-11-thia-6,9,24,27-tetraazapentacyclo[16.6.2.13,5.110,13.021,25]octacosa-1(24),10(27),12,16,18,20,22,25-octaene-5-carboxamide | 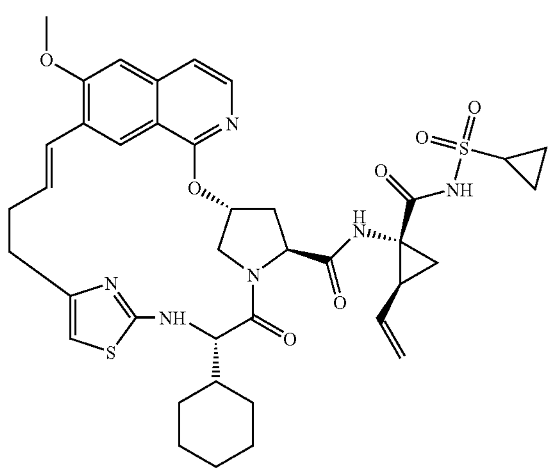 | 776 | Scheme 4 |

TABLE 3-continued

| Entry | Compound name | Structure | M + 1 | Preparative method |
|---|---|---|---|---|
| 3-13 | (3R,5S,8S,16E)-8-cyclohexyl-N-((1R,2S)-1-{[(cyclopropylsulfonyl)amino]carbonyl}-2-vinylcyclopropyl)-19,23-dimethoxy-14,14-dimethyl-7-oxo-2-oxa-11-thia-6,9,22,27-tetraazapentacyclo[16.6.2.1³,⁵.1¹⁰,¹³.0²¹,²⁵]octacosa-1(24),10(27),12,16,18,20,22,25-octaene-5-carboxamide | 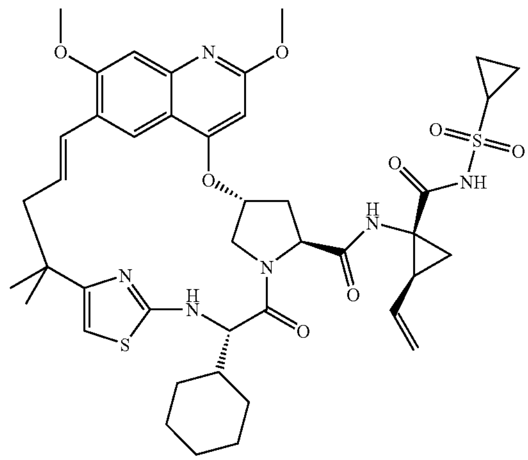 | 834 | Scheme 4 |
| 3-14 | (1R,22S,25S)-22-cyclopentyl-N-((1R,2S)-1-{[cyclopropylsulfonyl)amino]carbonyl}-2-ethenylcyclopropyl)-3,23-dioxo-2,28-dioxa-4,18,19,21,24-pentaazapentacyclo[22.1⁴,⁷.1¹⁷,²⁰.0⁶,¹¹]nonacosa-6,8,10,17,19-pentaene-25-carboxamide | 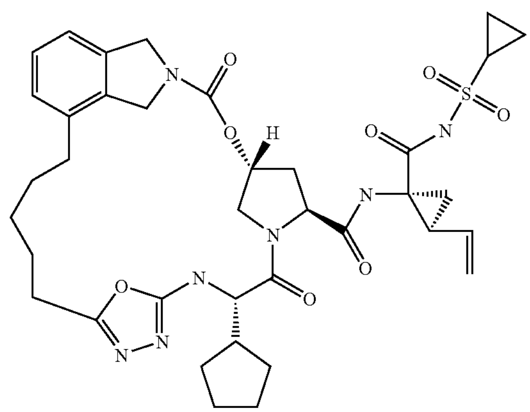 | 750 | Scheme 3 |
| 3-15 | (1R,12E,22S,25S)-22-cyclopentyl-N-((1R,2S)-1-{[cyclopropylsulfonyl)amino]carbonyl}-2-ethenylcyclopropyl)-3,23-dioxo-2,28-dioxa-4,18,19,21,24-pentaazapentacyclo[22.1⁴,⁷.1¹⁷,²⁰.0⁶,¹¹]nonacosa-6,8,10,12,17,19-hexaene-25-carboxamide | 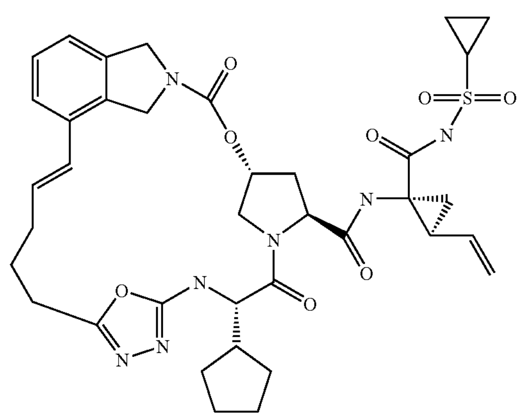 | 748 | Scheme 3 |

TABLE 3-continued

| Entry | Compound name | Structure | M + 1 | Preparative method |
|---|---|---|---|---|
| 3-16 | (3R,5S,8S)-N-((1R,2S)-1-{[(cyclopropylsulfonyl)amino]carbonyl}-2-vinylcyclopropyl)-22-ethyl-8-isopropyl-7-oxo-2,27-dioxa-6,9,11,12,24-pentaazapentacyclo[16.6.2.1$^{3,6}$.1$^{10,13}$.0$^{21,25}$]octacosa-1(24),10,12,18,20,22,25-heptaene-5-carboxamide | 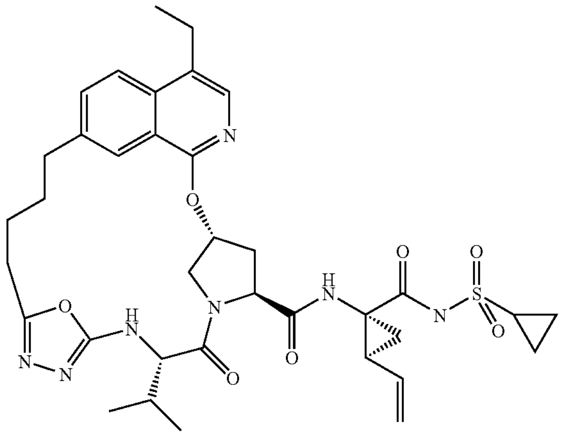 | 720 | Scheme 5 |

The invention claimed is:

1. A compound of formula (I):

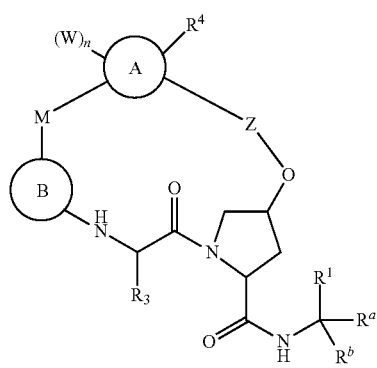

(I)

or a pharmaceutically acceptable salt thereof,
wherein:
  n is 0, 1 or 2;
  $R^1$ is $CO_2R^5$, $CONR^5SO_2R^5$, $CONR^5SO_2N(R^5)_2$ or tetrazolyl;
  $R^a$ and $R^b$, together with the carbon atom to which they are attached, form a $C_{3-6}$cycloalkyl group, optionally substituted by $R^2$;
  $R^2$ is $C_{1-6}$alkyl or $C_{2-6}$alkenyl, wherein said alkyl or alkenyl is optionally substituted with 1 to 3 halo;
  $R^3$ is $C_{1-6}$alkyl, $(CH_2)_{0-3}C_{3-8}$cycloalkyl, $(CH_2)_{0-3}$aryl or $(CH_2)_{0-3}$Het, optionally substituted by halo, $OR^5$, $SR^5$, $N(R^5)_2$, $C_{1-6}$alkyl, $NO_2$, CN, $CF_3$, $NR^5SO_2R^5$, $SO_2N(R^5)_2$, $NHCO_2R^5$, $NHCOR^5$, $NHCONHR^5$, $CO_2R^5$, $C(O)R^5$ or $CON(R^5)_2$;
  $R^4$ is hydrogen, halo, hydroxy, $C_{1-6}$alkyl, $C_{1-6}$alkoxy, CN, $NO_2$, $C_{3-8}$cycloalkyl, $N(R^5)_2$, aryl or heteroaryl, optionally substituted by 1 to 8 halo or $C_{1-4}$-alkyl;
  each $R^5$ is independently hydrogen, $C_{1-6}$alkyl or $C_{3-8}$cycloalkyl;
  each W is independently halo, $OR^5$, $C_{1-6}$alkyl, CN, $NO_2$, $CF_3$, $CO_2R^5$, $CON(R^5)_2$, $COR^5$, $NR^5C(O)R^5$, aryl or heteroaryl;
  Z is a bond or C=O;
  M is $C_{2-12}$alkylene or $C_{2-12}$alkenylene, optionally substituted by $C_{1-6}$alkyl, $(CH_2)_{0-3}C_{3-8}$cycloalkyl or $(CH_2)_{0-3}$aryl, and optionally containing one O or S atom;
  ring A is a 8- to 10-membered fused heterobicyclic ring system containing 1 to 4 heteroatoms selected from N, O and S; and
  ring B is a C-linked 5- or 6-membered heteroaromatic ring containing 1 to 4 heteroatoms selected from N, O and S.

2. The compound as claimed in claim 1, wherein n is 0 or 1.

3. The compound as claimed in claim 1, wherein $R^1$ is $CONR^5SO_2R^5$ or $CONR^5SO_2N(R^5)_2$ where $R^5$ is as defined in claim 1.

4. The compound as claimed in claim 1, wherein $R^a$ and $R^b$, together with the carbon atom to which they are attached, form a $C_{3-5}$cycloalkyl group, optionally substituted by $R^2$, where $R^2$ is $C_{1-6}$alkyl or $C_{2-6}$alkenyl.

5. The compound as claimed in claim 1, wherein $R^3$ is $C_{1-6}$alkyl or $(CH_2)_{0-3}C_{3-8}$cycloalkyl, optionally substituted by halo, $OR^5$ or $C_{1-6}$alkyl.

6. The compound as claimed in claim 1, wherein $R^4$ is hydrogen, halo, hydroxy, $C_{1-6}$alkyl, $C_{1-6}$alkoxy, $C_{3-8}$cycloalkyl or aryl.

7. The compound as claimed in claim 1, wherein each W is independently halo, $OR^5$, $C_{1-6}$alkyl, CN, $NO_2$, $CF_3$, $CO_2R^5$ or $CON(R^5)_2$.

8. The compound as claimed claim 1, wherein M is $C_{2-8}$alkylene or $C_{2-8}$alkenylene, optionally substituted by $C_{1-4}$alkyl or $C_{3-6}$cycloalkyl, and optionally containing one O atom.

9. The compound as claimed in claim 1, wherein A is a 9- or 10-membered fused heterobicyclic ring system containing 1 to 3 heteroatoms selected from N and O.

10. The compound as claimed claim 1, wherein B is a C-linked 5-membered heteroaromatic ring containing 2 or 3 heteroatoms selected from N, O and S.

11. The compound as claimed in claim 1, the compound is a compound of formula (Ia):

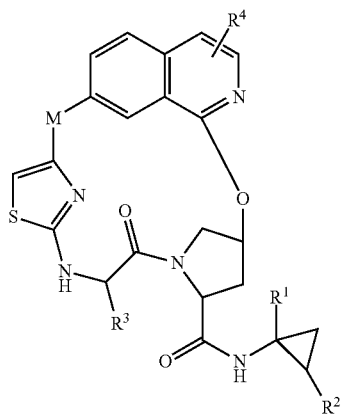

(Ia)

or a pharmaceutically acceptable salt thereof,
wherein $R^1$, $R^2$, $R^3$, $R^4$ and M are as defined in claim 1.

12. The compound as claimed in claim 1, the compound is a compound of formula (Ib):

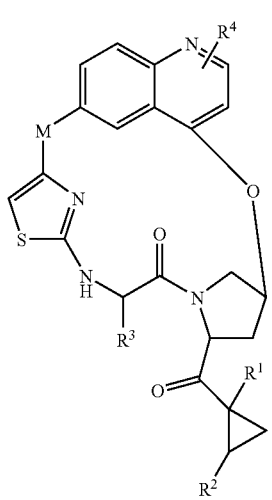

(Ib)

or a pharmaceutically acceptable salt thereof,
wherein $R^1$, $R^2$, $R^3$, $R^4$ and M are as defined in claim 1.

13. The compound as claimed in claim 1, the compound is a compound of formula (Ic):

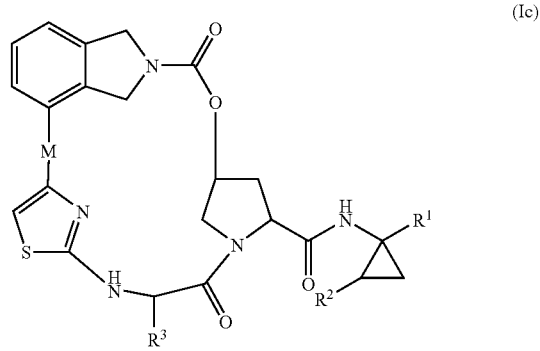

(Ic)

or a pharmaceutically acceptable salt thereof,
wherein $R^1$, $R^2$, $R^3$ and M are as defined in relation to formula (I).

14. The compound as claimed in claim 1, the compound is a compound of formula (Id):

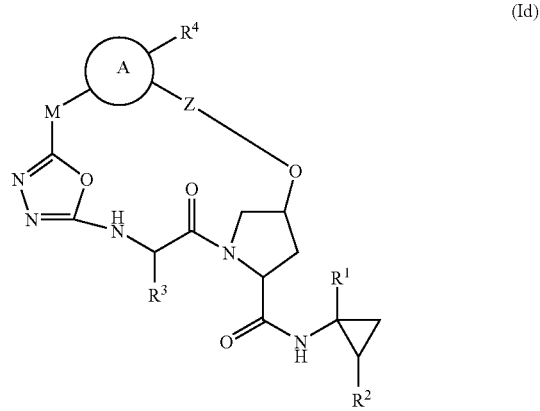

(Id)

or a pharmaceutically acceptable salt thereof,
wherein $R^1$, $R^2$, $R^3$, $R^4$, Z, M and A are as defined in claim 1.

15. The compound as claimed in claim 1, the compound is a compound formula (Ie):

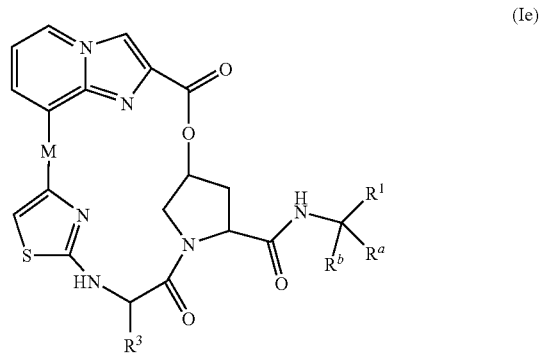

(Ie)

or a pharmaceutically acceptable salt thereof, wherein $R^1$, $R^a$, $R^b$, $R^3$ and M are as defined in relation to formula (I).

16. The compound as claimed in claim 1, the compound is a compound of formula (If):

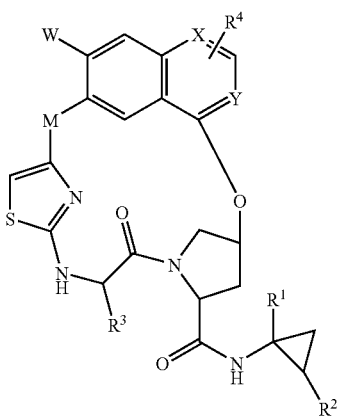

(If)

or a pharmaceutically acceptable salt thereof, wherein $R^1$, $R^2$, $R^3$, $R^4$, M and W are as defined in claim 1;
X is N when Y is CH; and
X is CH when Y is N.

17. The compound as claimed in claim 1 selected from:
(3R,5S,8S)—N-((1R,2S)-1-{[(cyclopropylsulfonyl) amino]carbonyl}-2-ethenylcyclopropyl)-8-(1-methylethyl)-7-oxo-2-oxa-11-thia-6,9,24,27-tetraazapentacyclo[16.6.2.1$^{3,6}$.1$^{10,13}$.0$^{21,25}$]octacosa-1(24),10(27),12, 18,20,22,25-heptaene-5-carboxamide, (3R,5S,8S)—N-((1R,2S)-1-{[(cyclopropylsulfonyl) amino]carbonyl}-2-ethenylcyclopropyl)-8-(1-methylethyl)-7-oxo-2-oxa-11-thia-6,9,25,28-tetraazapentacyclo[17.6.2.1$^{3,6}$.1$^{10,13}$.0$^{22,26}$]nonacosa-1(25),10(28),12, 19,21,23,26-heptaene-5-carboxamide, (3R,5S,8S)—N-((1R,2S)-1-{[(cyclopropylsulfonyl) amino]carbonyl}-2-ethenylcyclopropyl)-8-(1-methylethyl)-7-oxo-23-phenyl-2-oxa-11-thia-6,9,22,27-tetraazapentacyclo[16.6.2.1$^{3,6}$.1$^{10,13}$.0$^{21,25}$]octacosa-1 (24),10(27),12,18,20,22,25-heptaene-5-carboxamide, (3R,5S,8S,16E)-N-((1R,2S)-1-{[(cyclopropylsulfonyl) amino]carbonyl}-2-ethenylcyclopropyl)-8-(1,1-dimethylethyl)-7-oxo-2-oxa-11-thia-6,9,24,27-tetraazapentacyclo[16.6.2.1$^{3,6}$.1$^{10,13}$.0$^{21,25}$]octacosa-1(24),10 (27),12,16,18,20,22,25-octaene-5-carboxamide, (3R,5S,8S,16Z)—N-((1R,2S)-1-{[(cyclopropylsulfonyl) amino]carbonyl}-2-ethenylcyclopropyl)-8-(1,1-dimethylethyl)-7-oxo-2-oxa-11-thia-6,9,24,27-tetraazapentacyclo[16.6.2.1$^{3,6}$.1$^{10,13}$.0$^{21,25}$]octacosa-1(24),10 (27),12,16,18,20,22,25-octaene-5-carboxamide, (3R,5S,8S)—N-((1R,2S)-1-{[(cyclopropylsulfonyl) amino]carbonyl}-2-ethenylcyclopropyl)-8-(1,1-dimethylethyl)-7-oxo-2-oxa-11-thia-6,9,24,27-tetraazapentacyclo[16.6.2.1$^{3,6}$.1$^{10,13}$.0$^{21,25}$]octacosa-1(24),10 (27),12,16,18,20,22,25-octaene-5-carboxamide, (1R,12E,21S,24S)—N-((1R,2S)-1-{[(cyclopropylsulfonyl)amino]carbonyl}-2-ethenylcyclopropyl)-21-(1-methylethyl)-3,22-dioxo-2-oxa-18-thia-4,20,23,27-tetraazapentacyclo[21.2.1.1$^{4,7}$.1$^{16,19}$.0$^{6,11}$]octacosa-6,8, 10,12,16,19(27)-hexaene-24-carboxamide, (1R,12E,22S,25S)—N-((1R,2S)-1-{[(cyclopropylsulfonyl)amino]carbonyl}-2-ethenylcyclopropyl)-22-(1-methylethyl)-3,23-dioxo-2-oxa-19-thia-4,21,24,28-tetraazapentacyclo[22.2.1.1$^{4,7}$.1$^{17,20}$.0$^{6,11}$]octacosa-6,8, 10,12,17,20(28)-hexaene-25-carboxamide, (1R,22S,25S)—N-((1R,2S)-1-{[(cyclopropylsulfonyl) amino]carbonyl}-2-ethenylcyclopropyl)-22-(1,1-dimethylethyl)-3,23-dioxo-2-oxa-19-thia-4,21,24,28-tetraazapentacyclo[22.2.1.1$^{4,7}$.1$^{17,20}$.0$^{6,11}$]nonaacosa-6,8, 10,17,20(28)-pentaene-25-carboxamide, (1R,12E,22S,25S)—N-((1R,2S)-1-{[(cyclopropylsulfonyl)amino]carbonyl}-2-ethenylcyclopropyl)-22-(1,1-dimethylethyl)-3,23-dioxo-2-oxa-19-thia-4,21,24,28-tetraazapentacyclo[22.2.1.1$^{4,7}$.1$^{17,20}$.0$^{6,11}$]nonaacosa-6,8,10,12,17,20(28)-hexaene-25-carboxamide, 1R,12E,22S,25S)-22-cyclohexenyl-N-((1R,2S)-1-{[(cyclopropylsulfonyl)amino]carbonyl}-2-ethenylcyclopropyl)-3,23-dioxo-2-oxa-19thia-4,21,24,28-tetraazapentacyclo[22.2.1.1$^{4,7}$.1 $^{17,20}$.0$^{6,11}$]nonaacosa-6,8,10,12, 17,20(28)-hexaene-25-carboxamide, (1R,22S,25S)-22-cyclohexyl-N-((1R,2S)-1-{[(cyclopropylsulfonyl)amino]carbonyl}-2-ethenylcyclopropyl)-3, 23-dioxo-2-oxa-19-thia-4,21,24,28-tetraazapentacyclo [22.2.1.1$^{4,7}$.1$^{17,20}$.0$^{6,11}$]nonaacosa-6,8,10,17,20(28)-pentaene-25-carboxamide, (3R,5S,8S)-8-cyclohexyl-N-((1R,2S)-1-{[(cyclopropylsulfonyl)amino]carbonyl}-2-ethenylcyclopropyl)-7-oxo-2-oxa-11-thia-6,9,24,27-tetraazapentacyclo [16.6.2.1$^{3,6}$.1$^{10,13}$.0$^{21,25}$]octacosa-1(24),10(27),12,18, 20,22,25-heptaene-5-carboxamide, (1R,12E,22S,25S)—N-((1R,2S)-1-{[(cyclopropylsulfonyl)amino]carbonyl}-2-ethenylcyclopropyl)-22-[(1R)-1-methylpropyl]-3,23-dioxo-2-oxa-19-thia-4,21,24,28-tetraazapentacyclo[22.2.1.1$^{4,7}$.1$^{17,20}$.0$^{6,11}$]nonaacosa-6,8,10,12,17,20(28)-hexaene-25-carboxamide, (1R,12E,22S,25S)—N-((1R,2S)-1-{[(cyclopropylsulfonyl)amino]carbonyl}-2-ethenylcyclopropyl)-22-[(1S)-1-methylpropyl]-3,23-dioxo-2-oxa-19-thia-4,21,24,28-tetraazapentacyclo[22.2.1.1$^{4,7}$.1$^{17,20}$.0$^{6,11}$]nonaacosa-6,8,10,12,17,20(28)-hexaene-25-carboxamide, (3R,5S,8S,16E)-N-((1R,2S)-1-{[(cyclopropylsulfonyl) amino]carbonyl}-2-ethenylcyclopropyl)-8-[(1R)-1-methylpropyl]-7-oxo-2-oxa-11-thia-6,9,24,27-tetraazapentacyclo[16.6.2.1$^{3,6}$.1$^{10,13}$.0$^{21,25}$]octacosa-1 (24),10(27),12,16,18,20,22,25-octaene-5-carboxamide, (3R,5S,8S,16E)-N-((1R,2S)-1-{[(cyclopropylsulfonyl) amino]carbonyl}-2-ethenylcyclopropyl)-8-[(1S)-1-methylpropyl]-7-oxo-2-oxa-11-thia-6,9,24,27-tetraazapentacyclo[16.6.2.1$^{3,6}$.1$^{10,13}$.0$^{21,25}$]octacosa-1(24),10 (27),12,16,18,20,22,25-octaene-5-carboxamide, (1R,12E,22S,25S)-22-cyclohexyl-N-((1R,2R)-1-{[(cyclopropylsulfonyl)amino]carbonyl}-2-ethylcyclopropyl)-3,23-dioxo-2-oxa-19-thia-4,21,24,28-tetraazapentacyclo[22.2.1.1$^{4,7}$.1$^{17,20}$.0$^{6,11}$]nonaacosa-6,8,10,12, 17,20(28)-hexaene-25-carboxamide, (3R,5S,8S,16E)-N-((1R,2S)-1-{[(cyclopropylsulfonyl) amino]carbonyl}-2-ethenylcyclopropyl)-14,14-dimethyl-8-(1-methylethyl)-7-oxo-2-oxa-11-thia-6,9,24, 27-tetraazapentacyclo[16.6.2.1$^{3,6}$.1$^{10,13}$.0$^{21,25}$] octacosa-1(25),10(27),12,16,18,20,21,23,25-nonaene-5-carboxamide, (1R,12E,22S,25S)-22-cyclohexenyl-N-((1R,2S)-1-{[(cyclopropylsulfonyl)amino]carbonyl}-2-ethenylcyclopropyl)-3,23-dioxo-2,15-dioxa-19-thia-4,21,24,28-tetraazapentacyclo[22.2.1.1$^{4,7}$.1$^{17,20}$.0$^{6,11}$]nonaacosa-6,8, 10,12,17,20(28)-hexaene-25-carboxamide, (1R,22S,25S)-22-cyclohexenyl-N-((1R,2R)-1-{[(cyclopropylsulfonyl)amino]carbonyl}-2-ethylcyclopropyl)-3,23-dioxo-2-oxa-19-thia-4,21,24,28-tetraazapentacyclo[22.2.1.1$^{4,7}$.1$^{17,20}$.0$^{6,11}$]nonaacosa-6,8,10,17,20 (28)-pentaene-25-carboxamide, (3R,5S,8S)—N-((1R,2S)-1-{[(cyclopropylsulfonyl)amino]carbonyl}-2-ethenylcyclopropyl)-14,14-dimethyl-8-(1-methylethyl)-7-oxo-2-oxa-11-thia-6,9,24,27-tetraazapentacyclo[16.6.2.1$^{3,6}$.1$^{10,13}$.0$^{21,25}$]octacosa-1(25),10(27),12,18,20,21,23,25-octaene-5-carboxamide, (3R,5S,8S)—N-((1R,2S)-1-{[(cyclopropylsulfonyl)amino]carbonyl}-2-ethenylcyclopropyl)-8-isopropyl-7-oxo-2,27-dioxa-6,9,11,12,24-pentazapentacyclo[16.6.2.1$^{3,6}$.1$^{10,13}$.0$^{21,25}$]octacosa-1(24),10,12,18,20,22,25-heptaene-5-carboxamide, (5S,8S)—N-((1R,2S)-2-ethenyl-1-{[cyclopropylsulfonyl)amino]carbonyl}-2-ethenylcyclopropyl)-8-(1-methylethyl)-7-oxo-2,28-dioxa-6,9,11,12,25-pentaazapentacyclo[17.6.2.1$^{3,6}$.1$^{10,13}$.0$^{22,26}$]nonacosa-1(25),10,12,19,21,23,26-heptaene-5-carboxamide, (1R,12E,22S,25S)-22-cyclohexyl-N-((1R,2S)-1-{[cyclopropylsulfonyl)amino]carbonyl}-2-ethenylcyclopropyl)-3,23-dioxo-2,28-dioxa-4,18,19,21,24-pentaazapentacyclo[22.1.1$^{4,7}$.1$^{17,20}$.0$^{6,11}$]nonacosa-6,8,10,12,17,19-hexaene-25-carboxamide, (1R,22S,25S)-22-cyclohexyl-N-((1R,2S)-1-{[cyclopropylsulfonyl)amino]carbonyl}-2-ethenylcyclopropyl)-3,23-dioxo-2,28-dioxa-4,18,19,21,24pentaazapentacyclo[22.1.1$^{4,7}$.1$^{17,20}$.0$^{6,11}$]nonacosa-6,8,10,17,19-pentaene-25-carboxamide, (3R,5S,8S)—N-((1R,2S)-1-{[(cyclopropylsulfonyl)amino]carbonyl}-2-ethenylcyclopropyl)-23-iodo-8-isopropyl-7-oxo-2,28-dioxa-6,9,11,12,25-pentazapentacyclo[17.6.2.1$^{3,6}$.1$^{10,13}$.0$^{21,26}$]nonacosa-1(25),10,12,19,21,23,26-heptaene-5-carboxamide, (1R,12E,22S,25S)-22-cyclopentyl-N-((1R,2S)-1-{[(cyclopropylsulfonyl)amino]carbonyl}-2-vinylcyclopropyl)-3,23-dioxo-2-oxa-19-thia-4,21,24,28-tetraazapentacyclo[22.2.1.14,7.117,20.06,11]nonacosa-6,8,10,12,17,20(28)-hexaene-25-carboxamide, (1R,12E,21S,24S)-21-cyclohexyl-N-((1R,2S)-1-{[(cyclopropylsulfonyl)amino]carbonyl}-2-vinylcyclopropyl)-15,15-dimethyl-3,22-dioxo-2-oxa-18-thia-4,20,23,27-tetraazapentacyclo[22.2.1.14, 7.116,19.06,11]octacosa-6,8,10,12,16,19(27)-hexaene-24-carboxamide, (3R,5S,8S,16E)-8-cyclopentyl-N-((1R,2S)-1-{[(cyclopropylsulfonyl)amino]carbonyl}-2-vinylcyclopropyl)-7-oxo-2-oxa-11-thia-6,9,24,27-tetraazapentacyclo[16.6.2.13, 5.110,13.021,25]octacosa-1(24),10(27),12,16,18,20,22,25-octaene-5-carboxamide, (1R,12E,21S,24S)-21-cyclopentyl-N-((1R,2S)-1-{[(cyclopropylsulfonyl)amino]carbonyl}-2-vinylcyclopropyl)-15,15-dimethyl-3,22-dioxo-2-oxa-18-thia-4,20,23,27-tetraazapentacyclo[22.2.1.14, 7.116,19.06,11]octacosa-6,8,10,12,16,19(27)-hexaene-24-carboxamide, (3R,5S,8S,16E)-N-((1R,2S)-1-{[(cyclopropylsulfonyl)amino]carbonyl}-2-vinylcyclopropyl)-8-isopropyl-7-oxo-2-oxa-11-thia-6,9,24,27-tetraazapentacyclo[16.6.2.13, 5.110,13.021,25]octacosa-1(24),10(27),12,16,18,20,21,23,25-nonaene-5-carboxamide, (3R,5S,8S,16E)-8-cyclopentyl-N-((1R,2S)-1-{[(cyclopropylsulfonyl)amino]carbonyl}-2-vinylcyclopropyl)-19-methoxy-14,14-dimethyl-7-oxo-23-phenyl-2-oxa-11-thia-6,9,22,27tetraazapentacyclo[16.6.2.13,5.110,13.021,25]octacosa-1(24),10(27),12,16,18,20,22,25-octaene-5-carboxamide, (3R,5S,8S,16E)-8-[(1S)-1-methylpropyl]-N-((1R,2S)-1-{[(cyclopropylsulfonyl)amino]carbonyl}-2-vinylcyclopropyl)-19-methoxy-14,14-dimethyl-7-oxo-23-phenyl-2-oxa-11-thia-6,9,22,27-tetraazapentacyclo[16.6.2.13, 5.110,13.021,25]octacosa-1(24),10(27),12,16,18,20,22,25-octaene-5-carboxamide, (3R,5S,8S,16E)-8-cyclopentyl N-((1R,2S)-1-{[(cyclopropylsulfonyl)amino]carbonyl}-2-vinylcyclopropyl)-19-methoxy-7-oxo-23-phenyl-2-oxa-11-thia-6,9,22,27-tetraazapentacyclo[16.6.2.13, 5.110,13.021,25]octacosa-1(24),10(27),12,16,18,20,22,25-octaene-5-carboxamide, (3R,5S,8S,16Z)-8-cyclopentyl N-((1R,2S)-1-{[(cyclopropylsulfonyl)amino]carbonyl}-2-vinylcyclopropyl)-19-methoxy-7-oxo-23-phenyl-2-oxa-11-thia-6,9,22,27-tetraazapentacyclo[16.6.2.13, 5.110,13.021,25]octacosa-1(24),10(27),12,16,18,20,22,25-octaene-5-carboxamide, (3R,5S,8S,16E)-8-cyclohexyl-N-((1R,2S)-1-{[(cyclopropylsulfonyl)amino]carbonyl}-2-vinylcyclopropyl)-19-methoxy-14,14-dimethyl-7-oxo-23-phenyl-2-oxa-11-thia-6,9,22,27-tetraazapentacyclo[16.6.2.13,5.110,13.021,25]octacosa-1(24),10(27),12,16,18,20,22,25-octaene-5-carboxamide, (3R,5S,8S,16E)-8-cyclohexyl-N-((1R,2S)-1-{[(cyclopropylsulfonyl)amino]carbonyl}-2-vinylcyclopropyl)-19-methoxy-14,14-dimethyl-7-oxo-2-oxa-11-thia-6,9,24,27-tetraazapentacyclo[16.6.2.13,5.110,13.021,25]octacosa-1(24),10(27),12,16,18,20,22,25-octaene-5-carboxamide, (3R,5S,8S,16E)-8-cyclohexyl-N-((1R,2S)-1-{[(cyclopropylsulfonyl)amino]carbonyl}-2-vinylcyclopropyl)-19-methoxy-7-oxo-2-oxa-11-thia-6,9,24,27-tetraazapentacyclo[16.6.2.13, 5.110,13.021,25]octacosa-1(24),10(27),12,16,18,20,22,25-octaene-5-carboxamide, (3R,5S,8S,16E)-8-cyclohexyl-N-((1R,2S)-1-{[(cyclopropylsulfonyl)amino]carbonyl}-2-vinylcyclopropyl)-19,23-dimethoxy-14,14-dimethyl-7-oxo-2-oxa-11-thia-6,9,22,27-tetraazapentacyclo[16.6.2.13,5.110,13.021,25]octacosa-1(24),10(27),12,16,18,20,22,25-octaene-5-carboxamide, (1R,22S,25S)-22-cyclopentyl-N-((1R,2S)-1-{[cyclopropylsulfonyl)amino]carbonyl}-2-ethenylcyclopropyl)-3,23-dioxo-2,28-dioxa-4,18,19,21,24-pentaazapentacyclo[22.1.1$^{4,7}$.1$^{17,20}$.0$^{6,11}$]nonacosa-6,8,10,17,19-pentaene-25-carboxamide, (1R,12E,22S,25S)-22-cyclopentyl-N-((1R,2S)-1-{[cyclopropylsulfonyl)amino]carbonyl}-2-ethenylcyclopropyl)-3,23-dioxo-2,28-dioxa-4,18,19,21,24-pentaazapentacyclo[22.1.1$^{4,7}$.1$^{17,20}$.0$^{6,11}$]nonacosa-6,8,10,12,17,19-hexaene-25-carboxamide, (3R,5S,8S)—N-((1R,2S)-1-{[(cyclopropylsulfonyl)amino]carbonyl}-2-vinylcyclopropyl)-22-ethyl-8-isopropyl-7-oxo-2,27-dioxa-6,9,11,12,24-pentaazapentacyclo[16.6.2.1$^{3,6}$.1$^{10,13}$.0$^{21,25}$]octacosa-1(24),10,12,18,20,22,25-heptaene-5-carboxamide, or a pharmaceutically acceptable salt thereof.

18. A pharmaceutical composition comprising a compound of formula (I) in association with a pharmaceutically acceptable carrier, wherein said compound of formula (I):

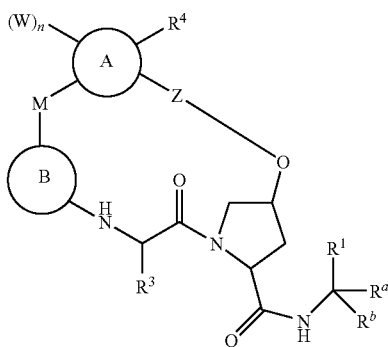

or a pharmaceutically acceptable salt thereof,
wherein:
n is 0, 1 or 2;
$R^1$ is $CO_2R^5$, $CONR^5SO_2R^5$, $CONR^5SO_2N(R^5)_2$ or tetrazolyl;
$R^a$ and $R^b$, together with the carbon atom to which they are attached, form a $C_{3-6}$cycloalkyl group, optionally substituted by $R^2$;
$R^2$ is $C_{1-6}$alkyl or $C_{2-6}$alkenyl, wherein said alkyl or alkenyl is optionally substituted with 1 to 3 halo;
$R^3$ is $C_{1-6}$alkyl, $(CH_2)_{0-3}C_{3-8}$cycloalkyl, $(CH_2)_{0-3}$aryl or $(CH_2)_{0-3}$Het, optionally substituted by halo, $OR^5$, $SR^5$, $N(R^5)_2$, $C_{1-6}$alkyl, $NO_2$, CN, $CF_3$, $NR^5SO_2R^5$, $SO_2N(R^5)_2$, $NHCO_2R^5$, $NHCOR^5$, $NHCONHR^5$, $CO_2R^5$, $C(O)R^5$ or $CON(R^5)_2$;
$R^4$ is hydrogen, halo, hydroxy, $C_{1-6}$alkyl, $C_{1-6}$alkoxy, CN, $NO_2$, $C_{3-8}$cycloalkyl, $N(R^5)_2$, aryl or heteroaryl, optionally substituted by 1 to 8 halo or $C_{1-4}$-alkyl;
each $R^5$ is independently hydrogen, $C_{1-6}$alkyl or $C_{3-8}$cycloalkyl;
each W is independently halo, $OR^5$, $C_{1-6}$alkyl, CN, $NO_2$, $CF_3$, $CO_2R^5$, $CON(R^5)_2$, $COR^5$, $NR^5C(O)R^5$, aryl or heteroaryl;
Z is a bond or C=O;
M is $C_{2-12}$alkylene or $C_{2-12}$alkenylene, optionally substituted by $C_{1-6}$alkyl, $(CH_2)_{0-3}C_{3-8}$cycloalkyl or $(CH_2)_{0-3}$aryl, and optionally containing one O or S atom;
ring A is a 8- to 10-membered fused heterobicyclic ring system containing 1 to 4 heteroatoms selected from N, O and S; and
ring B is a C-linked 5- or 6-membered heteroaromatic ring containing 1 to 4 heteroatoms selected from N, O and S.

19. The pharmaceutical composition as claimed in claim 18, further comprising one or more other agents for the treatment of viral infections or an immunomodulatory agent.

20. A method of inhibiting hepatitis C virus protease and/or of treating or preventing an illness due to hepatitis C virus, the method involving administering to a human or animal subject suffering from the condition a therapeutically or prophylactically effective amount of a compound of formula (I):

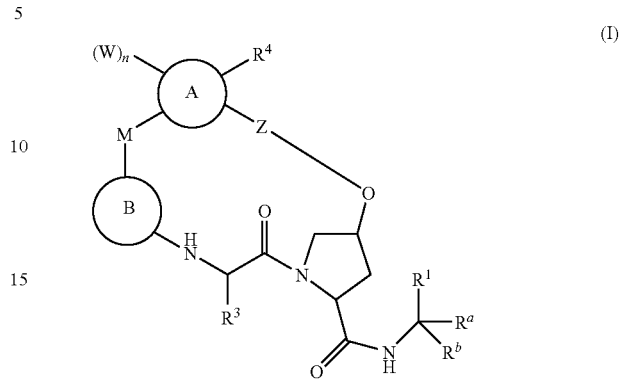

or a pharmaceutically acceptable salt thereof,
wherein:
n is 0, 1 or 2;
$R^1$ is $CO_2R^5$, $CONR^5SO_2R^5$, $CONR^5SO_2N(R^5)_2$ or tetrazolyl;
$R^a$ and $R^b$, together with the carbon atom to which they are attached, form a $C_{3-6}$cycloalkyl group, optionally substituted by $R^2$;
$R^2$ is $C_{1-6}$alkyl or $C_{2-6}$alkenyl, wherein said alkyl or alkenyl is optionally substituted with 1 to 3 halo;
$R^3$ is $C_{1-6}$alkyl, $(CH_2)_{0-3}C_{3-8}$cycloalkyl, $(CH_2)_{0-3}$aryl or $(CH_2)_{0-3}$Het, optionally substituted by halo, $OR^5$, $SR^5$, $N(R^5)_2$, $C_{1-6}$alkyl, $NO_2$, CN, $CF_3$, $NR^5SO_2R^5$, $SO_2N(R^5)_2$, $NHCO_2R^5$, $NHCOR^5$, $NHCONHR^5$, $CO_2R^5$, $C(O)R^5$ or $CON(R^5)_2$;
$R^4$ is hydrogen, halo, hydroxy, $C_{1-6}$alkyl, $C_{1-6}$alkoxy, CN, $NO_2$, $C_{3-8}$cycloalkyl, $N(R^5)_2$, aryl or heteroaryl, optionally substituted by 1 to 8 halo or $C_{1-4}$-alkyl;
each $R^5$ is independently hydrogen, $C_{1-6}$alkyl or $C_{3-8}$cycloalkyl;
each W is independently halo, $OR^5$, $C_{1-6}$alkyl, CN, $NO_2$, $CF_3$, $CO_2R^5$, $CON(R^5)_2$, $COR^5$, $NR^5C(O)R^5$, aryl or heteroaryl;
Z is a bond or C=O;
M is $C_{2-12}$alkylene or $C_{2-12}$alkenylene, optionally substituted by $C_{1-6}$alkyl, $(CH_2)_{0-3}C_{3-8}$cycloalkyl or $(CH_2)_{0-3}$aryl, and optionally containing one O or S atom;
ring A is a 8- to 10-membered fused heterobicyclic ring system containing 1 to 4 heteroatoms selected from N, O and S; and
ring B is a C-linked 5- or 6-membered heteroaromatic ring containing 1 to 4 heteroatoms selected from N, O and S.

* * * * *